United States Patent [19]
Willoughby

[11] Patent Number: 5,873,721
[45] Date of Patent: Feb. 23, 1999

[54] IMPLANT ABUTMENT SYSTEMS, DEVICES, AND TECHNIQUES

[75] Inventor: Andrew J. M. Willoughby, Nassau, Bahamas

[73] Assignee: ADT Advanced Dental Technologies, Ltd., Cyprus

[21] Appl. No.: 662,069

[22] Filed: Jun. 12, 1996

Related U.S. Application Data

[62] Division of Ser. No. 176,011, Dec. 23, 1993, Pat. No. 5,527,182.

[51] Int. Cl.[6] .................................................. A61C 8/00
[52] U.S. Cl. ............................................ 433/173; 433/172
[58] Field of Search ................................... 433/172, 173, 433/174, 175, 176

[56] References Cited

U.S. PATENT DOCUMENTS

| | | | |
|---|---|---|---|
| 3,866,321 | 2/1975 | Valen | 433/176 |
| 4,318,696 | 3/1982 | Kasama et al. | 433/173 |
| 4,631,031 | 12/1986 | Richter | 433/173 |
| 4,687,443 | 8/1987 | Driskell | 433/173 |
| 4,713,003 | 12/1987 | Symington et al. | 433/173 |
| 4,744,756 | 5/1988 | Ross | 433/173 |
| 4,756,689 | 7/1988 | Lundgren et al. | 433/173 |
| 4,780,080 | 10/1988 | Haris | 433/173 |
| 4,793,808 | 12/1988 | Kirsch | 433/173 |
| 4,850,870 | 7/1989 | Lazzara et al. | 433/174 |
| 4,854,872 | 8/1989 | Detsch | 433/173 |

(List continued on next page.)

FOREIGN PATENT DOCUMENTS

| | | | |
|---|---|---|---|
| 2408341 | 7/1979 | France | 433/173 |

OTHER PUBLICATIONS

Straumann Dental Product Catalogue (ITI® Dental Implant System, 1995)*.
Straumann Dental Techno Info, "The use of the Octasystem® milling cylinder" (ITI® Dental Implant System) (undated)*.
Straumann Dental Techno Info, "Transversal screw–retained single crowns with the Octasystem®" (ITI® Dental Implant System) (undated)*.
Bonefit® Original ITI–Dental Implants, Octa Techno Info No. 2, "Operator–removable bridges and single crowns," (Institut Straumann Dental) (undated)*.

(List continued on next page.)

*Primary Examiner*—Cary E. O'Connor
*Attorney, Agent, or Firm*—James L. Ewing, IV; Kilpatrick Stockton LLP

[57] ABSTRACT

Dental implant abutment systems, related devices, and implantology processes and techniques. The abutment systems include a base that is adapted to mount in nonrotating fashion on any desired dental implant, root form or blade, from any supplier, together with a fixation screw which secures the base to the implant. A core, to which an abutment is cast in customized shape and form as desired is attached to the base preferably in threaded fashion and secured with an appropriate antirotational mechanism. Alternatively, the core and abutment may be formed using CAM processes. Such abutment systems, unlike prevalent conventional systems, do not require a central access bore in the core or abutment components, and they occupy significantly less volume than conventional abutments. Accordingly, abutment systems according to the present invention more flexibly accommodate a wide range of axial inclinations between implant and the overlying crown or prosthesis, preclude loosening of fixation screws, allow precision attachments to be included in the abutments for providing virtually completely passively fitting patient removable prostheses, and save considerable time, effort and expense because of the added simplicity and lower parts inventory required. Also disclosed are tapered gingivectomy procedures for replicating natural tooth emergence which is enhanced by abutments according to the present invention, together with precision attachments, impression copings and analogs, and other peripheral components useful with systems and techniques of the present invention.

34 Claims, 24 Drawing Sheets

U.S. PATENT DOCUMENTS

| | | | |
|---|---|---|---|
| 4,856,994 | 8/1989 | Lazzara et al. | 433/173 |
| 4,955,811 | 9/1990 | Lazzara et al. | 433/173 |
| 4,988,298 | 1/1991 | Lazzara et al. | 433/173 |
| 5,015,186 | 5/1991 | Detsch | 433/173 |
| 5,033,962 | 7/1991 | Scatena | 433/173 |
| 5,035,619 | 7/1991 | Daftary | 433/173 |
| 5,073,111 | 12/1991 | Daftary | 433/173 |
| 5,104,318 | 4/1992 | Piche et al. | 433/173 |
| 5,106,299 | 4/1992 | Ghalili | 433/172 |
| 5,116,225 | 5/1992 | Riera | 433/173 |
| 5,125,839 | 6/1992 | Ingber et al. | 433/169 |
| 5,145,372 | 9/1992 | Daftary et al. | 433/173 |
| 5,152,687 | 10/1992 | Amino | 433/174 |
| 5,178,539 | 1/1993 | Peltier et al. | 433/176 |
| 5,180,303 | 1/1993 | Hornburg et al. | 433/173 |
| 5,199,873 | 4/1993 | Schulte et al. | 433/173 |
| 5,417,568 | 5/1995 | Giglio | 433/173 |
| 5,427,906 | 6/1995 | Hansen | 433/173 |
| 5,527,182 | 6/1996 | Willoughby | 433/169 |

OTHER PUBLICATIONS

A. Fenton "The Role of Dental Implants in the Future" 123 *J.A.D.A.* pp. 37–42 (Jan. 1992).

A. Jaggers, A.M. Simons, S.E. Badr, "Abutment Selection For Anterior Single Tooth Replacement: A Clinical Report", 69 *J. Prosthetic Dentisry*, pp. 133–135 (No. 2, Feb. 1993).

B. Langer, D.Y. Sullivan, "Osseointegration: Its Impact on the Interrelationship of Periodontics and Restorative Dentistry; Part II"; 9 *Int'l J. of Periodontics and Restorative Dentistry*, pp. 165–183 (No. 3, 1989).

B. Langer "Dental Implants Used for Periodontal Patients" 121 *J.A.D.A.* pp. 505–508 (Oct. 1990).

B. Nicolucci, "Dental Implants: The Blade Implant," 83 Oral Health, pp. 55–60 (No. 9, 1993).

B. Svensson, R. Adell, B. Swarte, "Correction of Implant Malalignment by Segmental Osteotomy: A Case Report," 8 Int'l *J. of Oral and Maxillofacial Implants*, pp. 459–463 (No. 4, 1993).

B.D. Monteith, "Minimizing Biomechanical Overload in Implant Prostheses: A Computerized Aid To Design," 69 *J. of Prosthetic Denistry*, pp. 495–502, (No. 5, 1993).

C.E. English, "The Critical A–P Spread," 1 *The Implant Society*, pp. 2–3 (No. 1 1990).

C.E. Misch, H. Zaki, and B. Marshak, "The Use of Intra Coronal Attachments in Removable Prostheses," 8 *Int'l J. of Oral Implantology*, pp. 81–84, (No. 2, 1991).

C.E. Rieder, "Copings on Tooth and Implant Abutments for Superstructure Prostheses," 10 *Int'l J. of Periodontics and Restorative Dentistry*, pp. 437–451 (No. 6, 1990).

C.M. Tan–Bruggenkate, F. Sutter, H.S. Oosterbeek and A. Schroeder, "Indications for Angled Implants," 67 *J. Prosthetic Denistry*, pp. 85–93 (No. 1, Jan. 1992).

D.C. Holmes, W.R. Grigsby, V.K. Geol, J.C. Keller, "Comparison of Stress Transmission in the IMZ Implant System with Polyoxymethylene or Titanium Intramobile Element: A Finite Element Stress Analysis," 7 *Int'l J. Oral Maxillofacial Implants*, pp. 450–458 (No. 4, 1992).

D.E. Tolman, W.R. Laney, "Tissue–Integrated Prosthesis Complications," 7 *Int'l J. of Oral and Maxillofacial Implants*, pp. 477–478 (No. 4, 1992).

E.A. McGlumphy, W.V. Campagni, L.J. Peterson, "A Comparison of the Stress Transfer Characteristics of a Dental Implant with a Rigid or a Resilient Internal Element," 62 *J. of Prosthetic Dentistry*, pp. 586–593 (No. 5, 1989).

F. Duret, "The Practical Dental CAD/CAM in 1993," 59 *CDA J.*, pp. 445–452 (No. 5, May, 1993).

G. Zarb, et al., "Osseointegration: A Reguiem for the Perodontal Ligament?" 11 *Int'l J. of Periodontics and Restorative Dentistry*, pp. 88–91 (No. 2, 1991).

G.J. Chiche, A. Pinault, "Consideration for Fabrication of Implant Supported Posterior Restorations," 4 *Int'l J. of Prosthodontic* pp. 37–44 (No. 1, 1991).

G.J. Chiche, et al., "Adapting Fixed Prosthodontics Principles to Screw–Retained Restorations," 2 *Int'l J. of Prosthodontics*, pp. 317–322 (No. 4, 1989).

G.J. Chiche, et al, "Auxillary Substructure for Screw–Retained Prosthesis," 2 *Int'l. J. of Prosthodontics*, pp. 407–412 (No. 5, 1989).

H. Falk, L. Laurell, D. Lundgren, "Occlusal Force Pattern in Dentitions with Mandibular Implant–Supported Fixed Cantilever Prostheses Occluded with Complete Dentures," 4 *Int'l J. Oral Maxillofacial Implants* pp. 55–62 (No. 1, 1989).

H.B. Kay, "Free Standing Versus Implant–Tooth Interconnected Restoration: Understanding the Prosthodontic Perspective," 13 *Int'l J. of Periodontics and Restorative Dentistry*, pp. 46–69, (No. 1, 1993).

I. Ericsson, U. Lekholm, P. Branemark, J. Lindhe, P. Glantz, S. Nyman, "A Clinical Evaluation of Fixed Bridge Restorations Supported by the Combination of Teeth and Osseointegrated Titanium Implants," 13 *J. Clin. Periodontal*, pp. 307–312 (No. 4, 1986).

Ibbott, Kovach and Carlson–Mann, "Surgical Correction for Esthetic Problems Associated with Dental Implants," 58 *C.D.A.J.*, pp. 561–562 (No. 7, Jul. 1992).

Implant Support Systems Product Catalog, pp. 19–22, (1993).

J. Beumer III and S.G. Lewis, "The Branemark Implant System: Clinical and Laboratory Procedures," Ch. 5 figs. 149A and B. 150, 151), pp. 228–229 (Ishiyaku Euro–America 1989).

J.E. Bentley, "Surgical Dental Implants," *J.A.D.A.*, (17 pages) (Monograph, Aug. 1993).

K.B. Tan, J.E. Rubenstien, J.I. Nicholls, R.A. Yuodelis, "Three–Dimensional Analysis of the Casting Accuracy of One Piece, Osseointegrated Implant–Retained Prostheses," 6 *Int'l J. of Prosthodontics*, pp. 346–363 (No. 4, 1993).

L. Hongchen, Z. Gilin and L. Ning, "Edentulous Position of the Temporomandibular Joint," 67 *J. Prosthetic Dentistry*, pp. 401–404 (No. 3, Mar. 1992).

Lewis, Llamas and Avera, "The UCLA Abutment: A Four Year Review," 67 *J. Prosthetic Dentistry*, pp. 509–515 (No. 4, Apr. 1992).

M.L. Perel, "Interview With H.I. Bader: How To Motivate, Inform Dental Implant Patients On Home Care," 4 *Dental Implantology Update*, pp. 57–60 (No. 7, Jul. 1993).

M. Perel, "An Interview with Charles E. English: The Mandibular Overdenture," 4 *Dental Implantology Update*, pp. 9–14 No. 2 Feb. 1993).

M. Perel, "Interview with Y.M. Ismail: Occlusion and Biomechanics in Implant Dentistry," 4 Dental Implantology Update, pp. 6–8 (No. 1, Jan. 1993).

M. Perel, "Retrievability and Screw–Hole Access," 4 *Dental Implantology Update*, p. 55 (fig. 9), p. 60 (figs, 5–10) (No. 8, Aug. 1993).

M.L. Perel, "Interview With Dr. H.J. Gulbransen: Combining Implants and Natural Teeth Within the Same Arch," 4 *Dental Implantology Update*, pp. 74–76; (No. 9, Sep. 1993).

Mathys Product Catalog lArticles in the Mathys Product Catalog and Scientific Research Papers, including Dr. G. Graber, ZWR 100. Jahr g. 1992, Nr. 2 70–76; Dr. Ledermann, "Neue Chirurgische, Konstruktive und Zahntechnishce Aspekte in der Enlossalen Implantologie," *Quintessenz Heft*, 1 Jan. 1992 pp. 43, 7–22 (1992) (61 pages total).

P.E. Dawson, "Evaluation, Diagnosis and Treatment of Occlusal Problems" Ch. 16 excerpts, pp. 274, 291 (C.V. Mosby Co. 2d ed. 1989).

P–R Liu, B.P. Isenberg and K.F. Leinfelder,"Evaluating CAD–CAM Generated Ceramic Veneers," 124 *J.A.D.A.*, pp. 59–63 (Apr. 1993).

P.W. Cowan, "Surgical Templates for the Placement of *Osseointegrated Implants,*" 21 Quintessence International, pp. 391–396, (No. 5, 1990).

R.B. Johns, et al., "A Multicenter Study of Overdentures Supported by Branemark Implants", 7 *Int'l J. Oral & Maxillofacial Implants*, pp. 513–521 (No. 4, 1992).

R.C. Hertel, W. Kalk, "Influence of the Dimension of Implant Superstructure on Peri–Implant Bone Loss," 6 *Int'l J. of Prosthodontics*, pp. 18–24, (No. 1, 1993).

R.C. Olarn, W.R. Lacefield, "The Passive Fitting Implant Prosthesis," 4 *The Implant Society*, pp. 8–15 (No. 2, 1993).

R.J. Lazzara, "Managing The Soft Tissue Margin: The Key To Implant Aesthetics," 5 *Practical Periodontics and Aesthetic Dentistryt*, pp. 1–7 (No. 5, Jun./Jul. 1993).

R.K.K. Ow, K.H. Ho, "Retrieval of the Resilient Element in an Osseointegrated Implant System," 68 *J. Prosthetic Dentistry*, pp. 93–95 (Jul. 1992).

R.M. Meffert, "What is Peri–Implantitis and How Do We Prevent and Treat It?," 4 *J. Michigan Dental Assoc.*, pp. 32–33, 36–39 (No. 4, Apr./May 1992).

R.M. Watson, D.M. Davis, G.H. Forman, T. Coward, "Considerations in Design and Fabrication of Maxillary Implant Supported Prostheses," 4 *Int'l J. of Prosthodontics*, pp. 232–239 (No. 3, 1991).

R.P. Desiardens, "Prosthesis Design for Osseointegrated Implants in the Edentulous Maxilla," 7 *Int'l J. of Oral and Maxillofacial Implants*, pp. 311–320 (No. 3, 1992).

Siemens Medical Engineering Group Dental Sector, CEREC Computer Reconstruction, CEREC Pamphlet, pp. 1–14.

Christensen, G.J., "Implant Prosthodontics Contribute to Restorative Dentistry," 121 *J.A.D.A.*, pp. 340, 341, 344, 345, 348, 350, (Sep. 1990).

Garber, David A., "Implants—The Name of the Game is Still Maintenance," 12 *Compendium Contin. Educ. Dent.*, pp. 876, 878, 880, 882, 884, 888 (No. 12, 1991).

Grunder, U., J. Strub, "Implant–Supported Suprastructure Design," 10 *Int'l J. of Periodontics and Restorative Dentistry*, pp. 18–38, (No. 1, 1990).

Israelson, Hilton, J. Plemons, "Dental Implants, Regenerative Techniques, and Periodontal Plastic Surgery to Restore Maxillary Anterior Esthetics," 8 *Int'l J. of Maxillofacial Implants*, pp. 555–561, (No. 5, 1993).

McGlumphy, Edwin A., et al., "The Combination Implant Crown: A Cement– and Screw–Retained Restoration," 12 *Compendium Continuing Educ. Dent.*, pp. 34, 36, 38, 40–42, (No. 1, Jan. 1991).

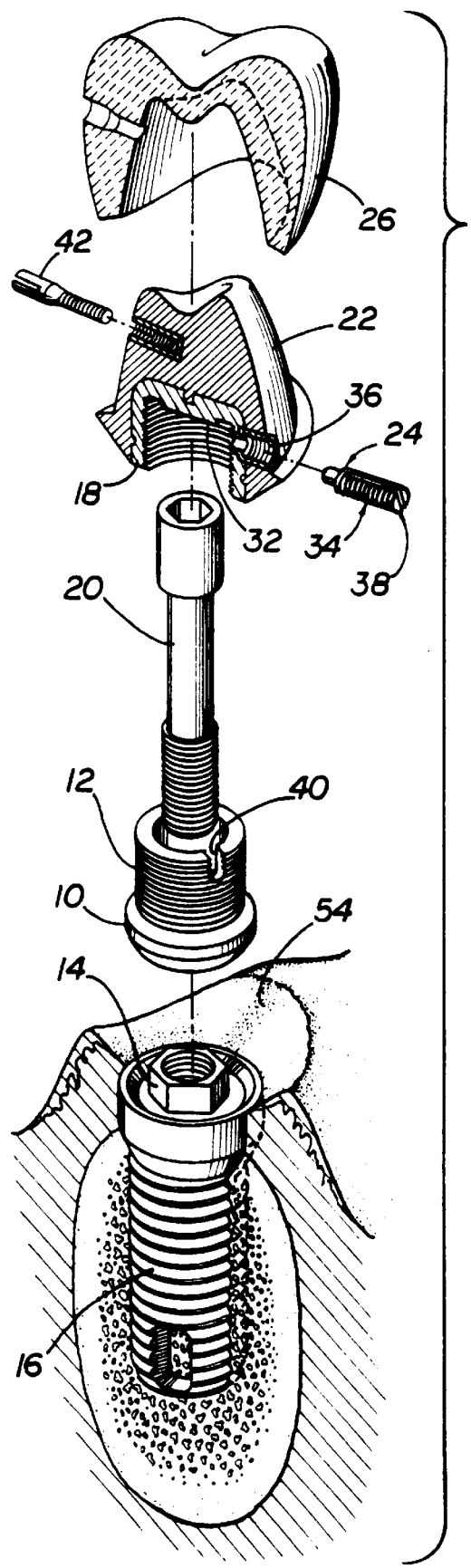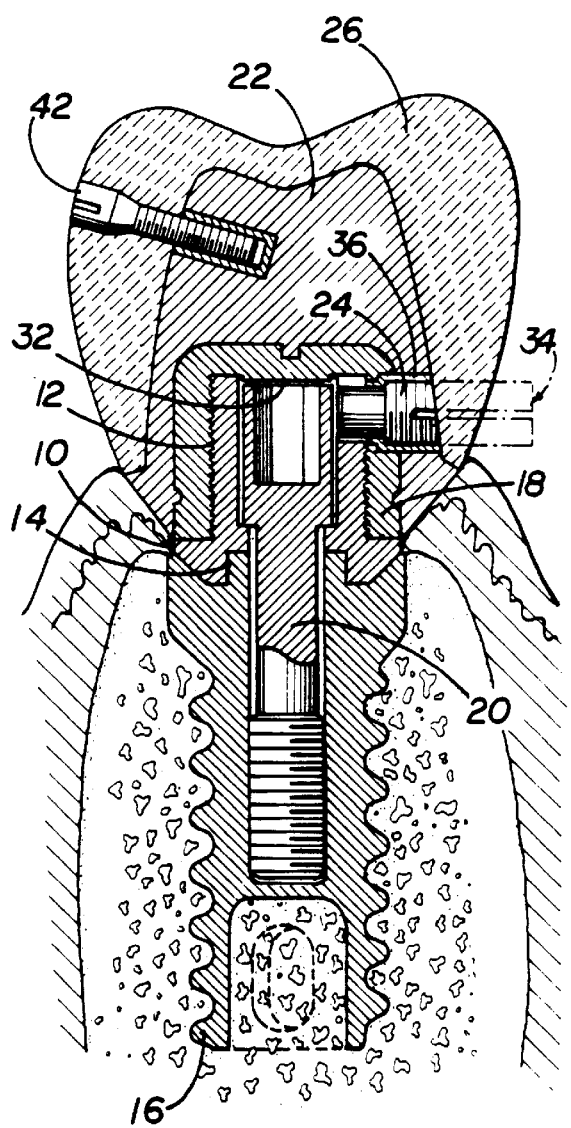
FIG 2
FIG 3

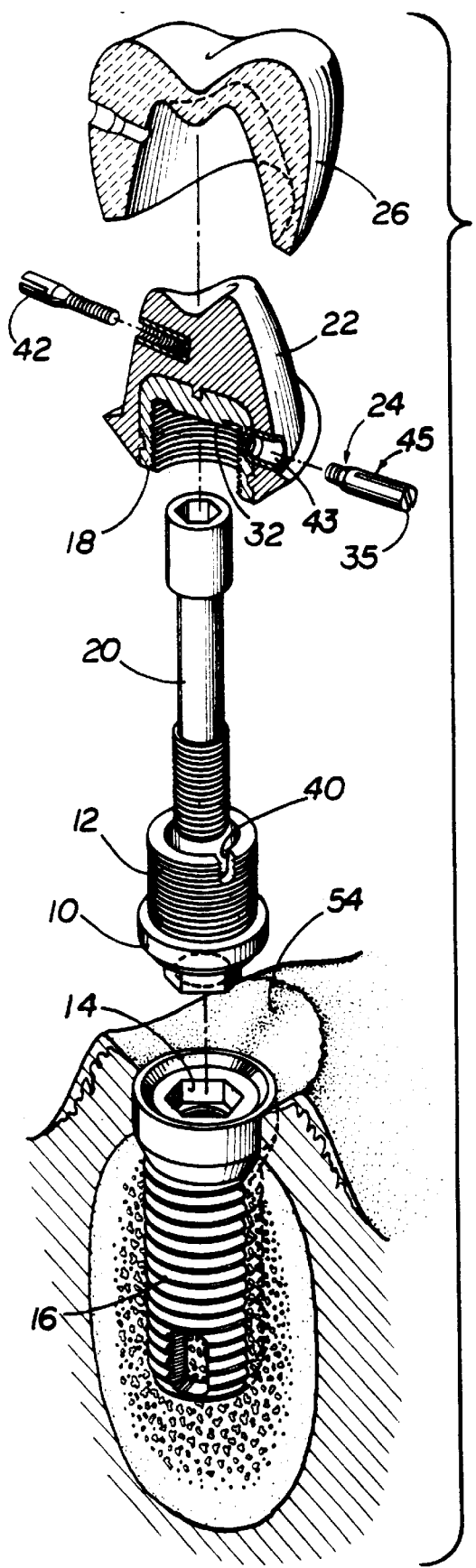
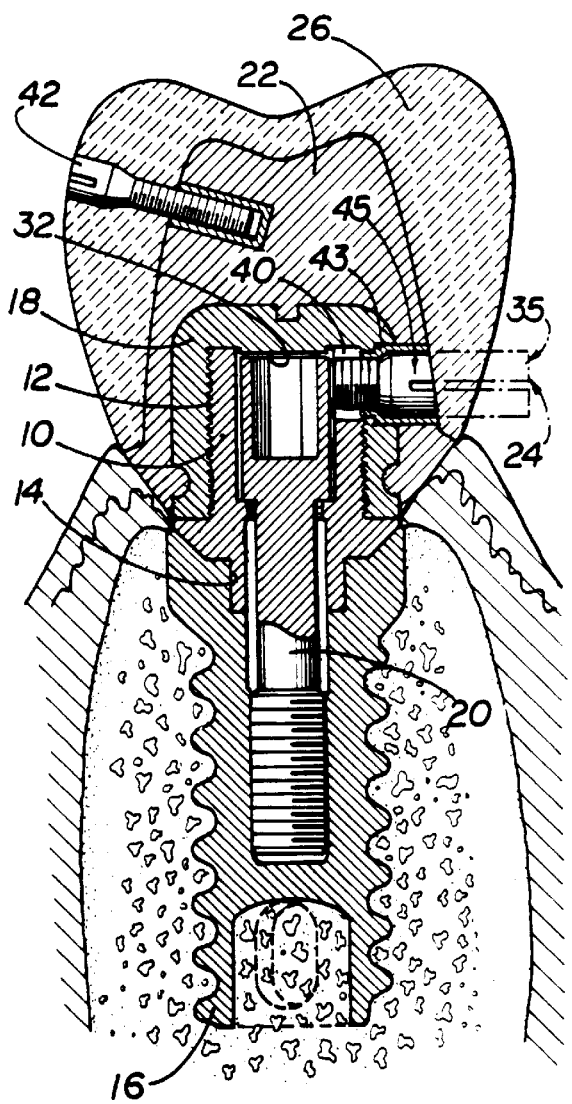
FIG 4
FIG 5

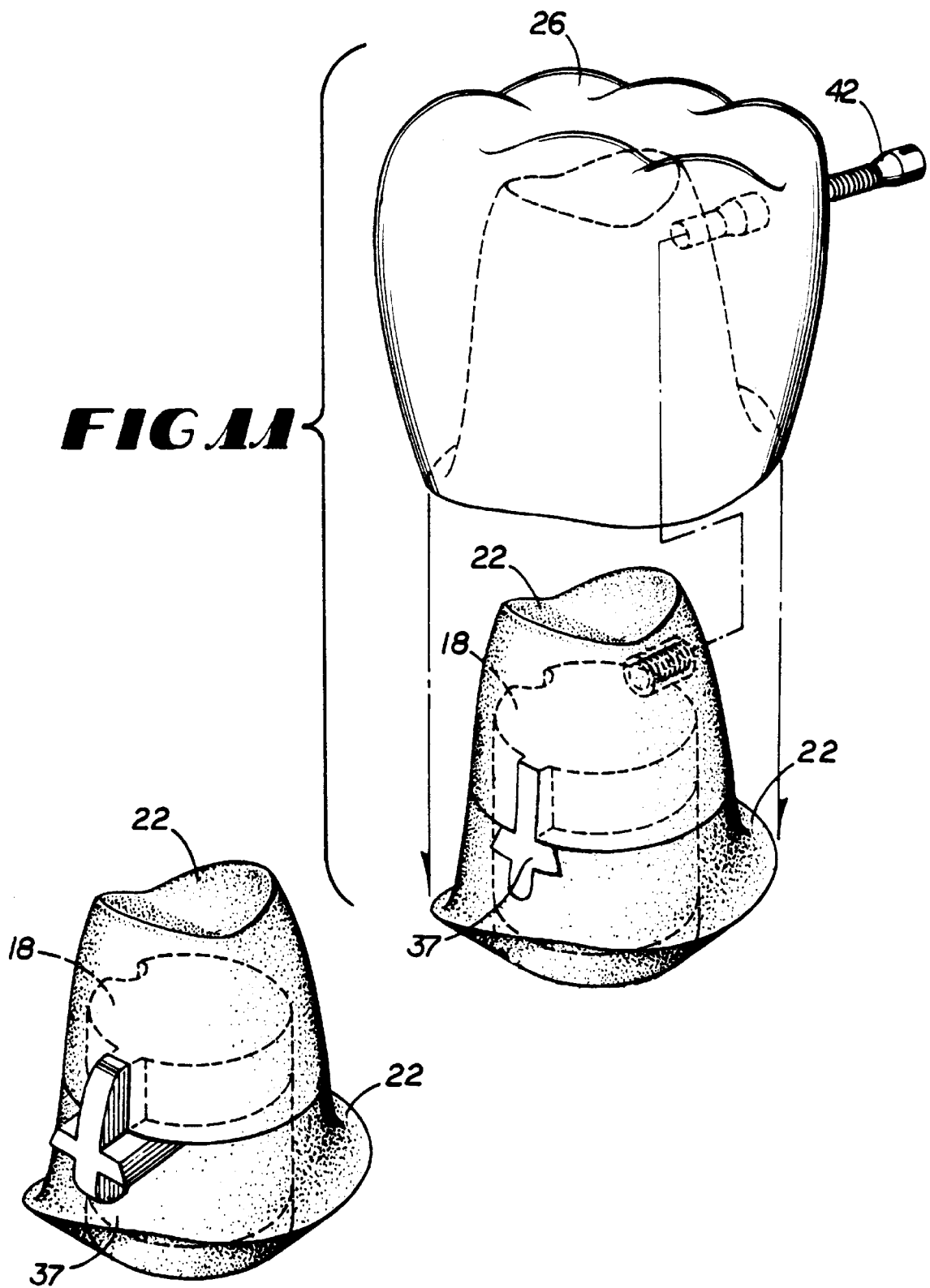

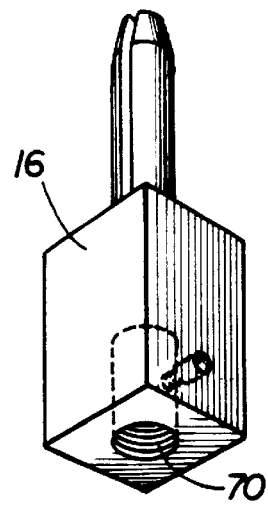
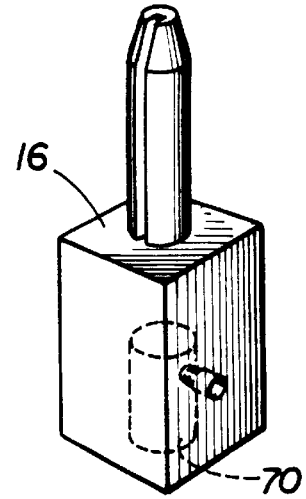
FIG 14  FIG 15
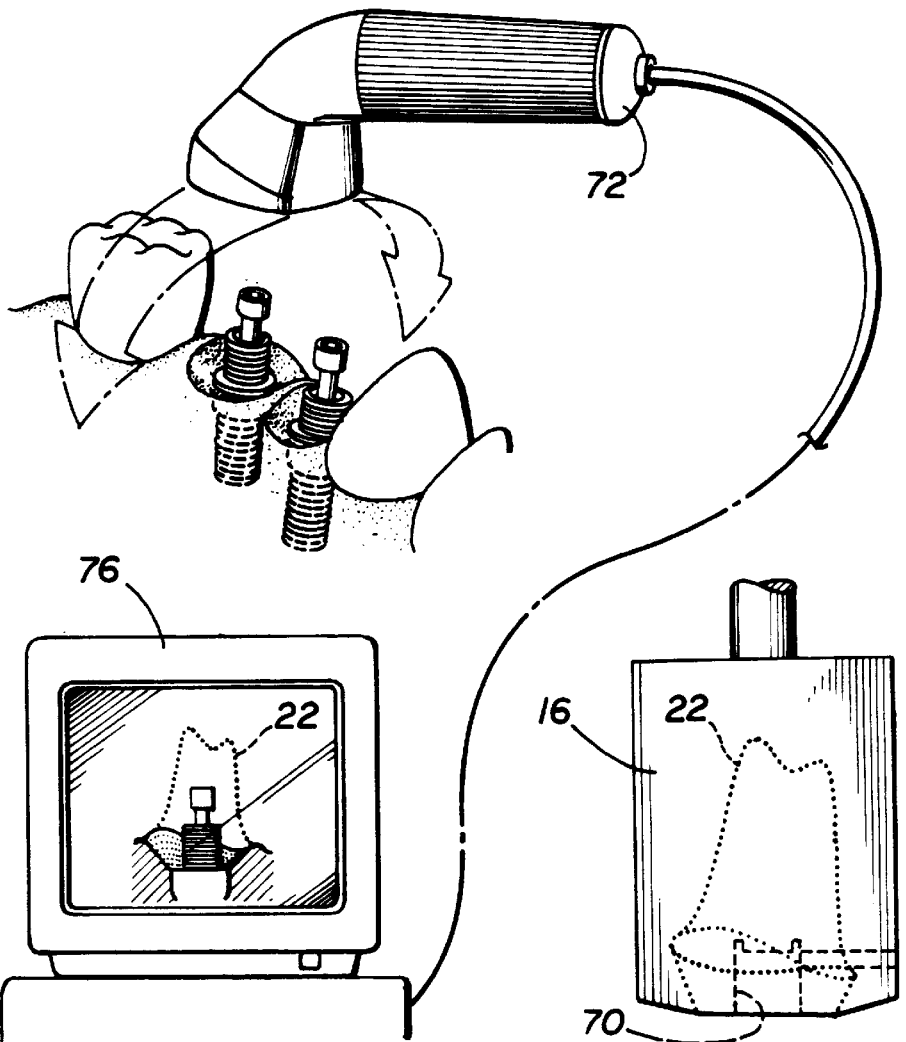
FIG 16  FIG 16A

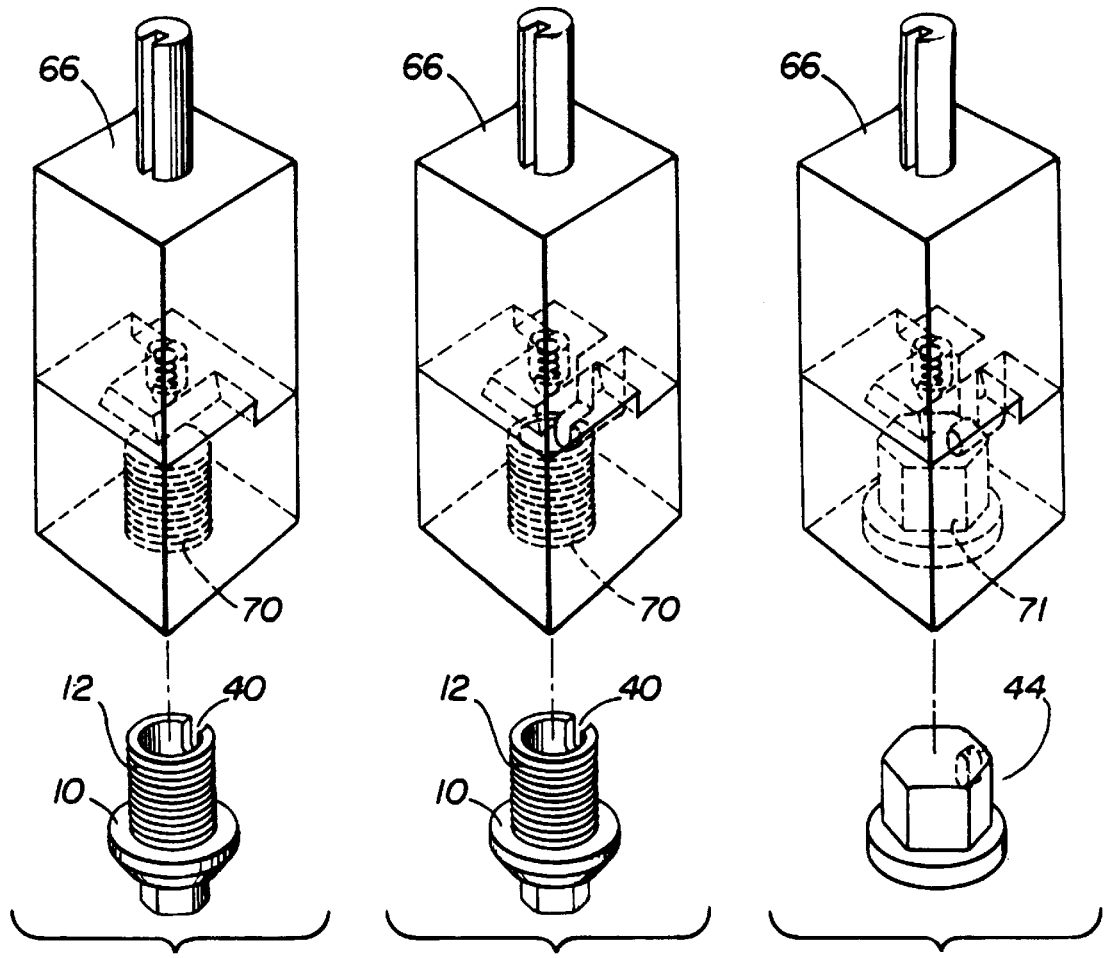
FIG 18  FIG 19  FIG 20
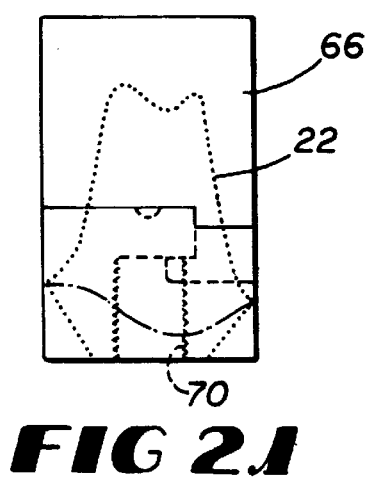
FIG 21
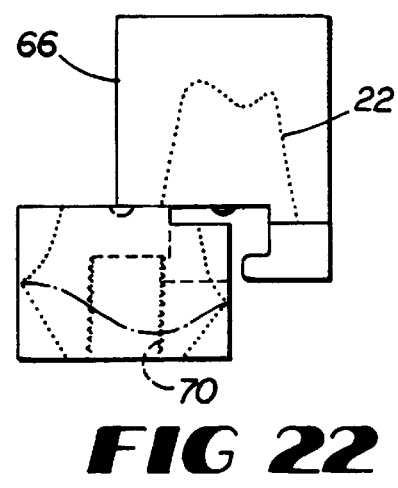
FIG 22

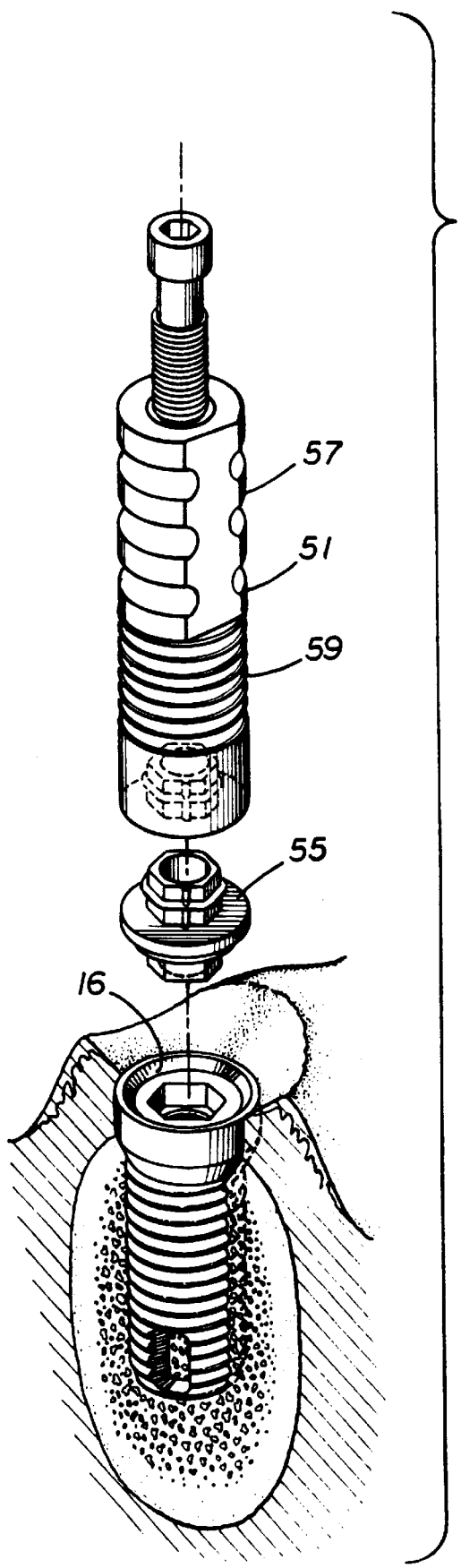
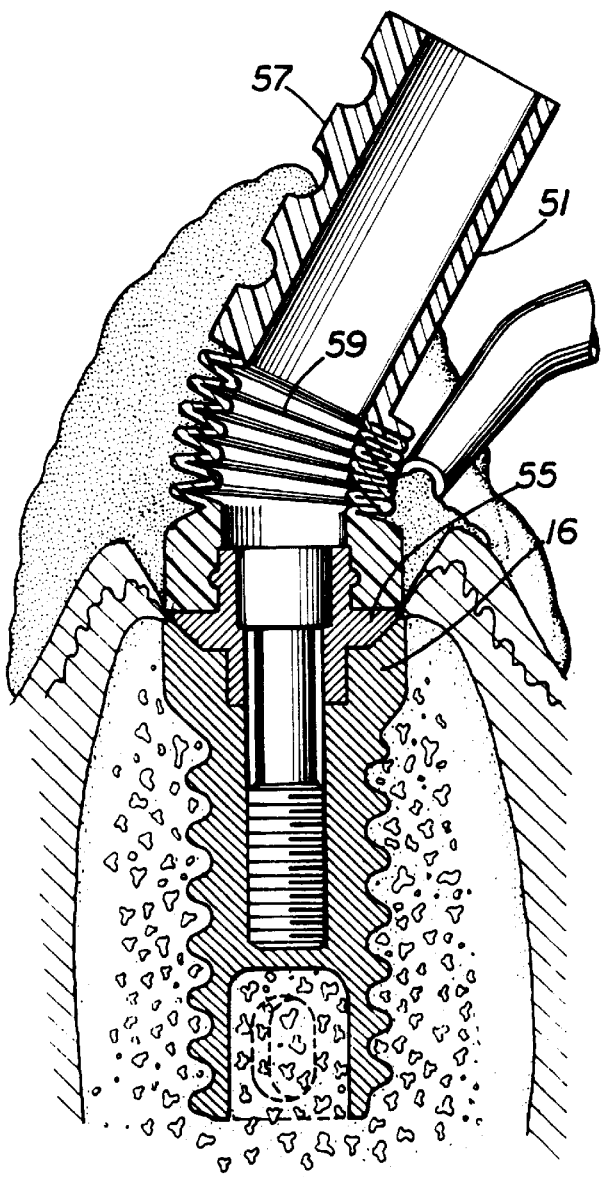
FIG 26A
FIG 26B

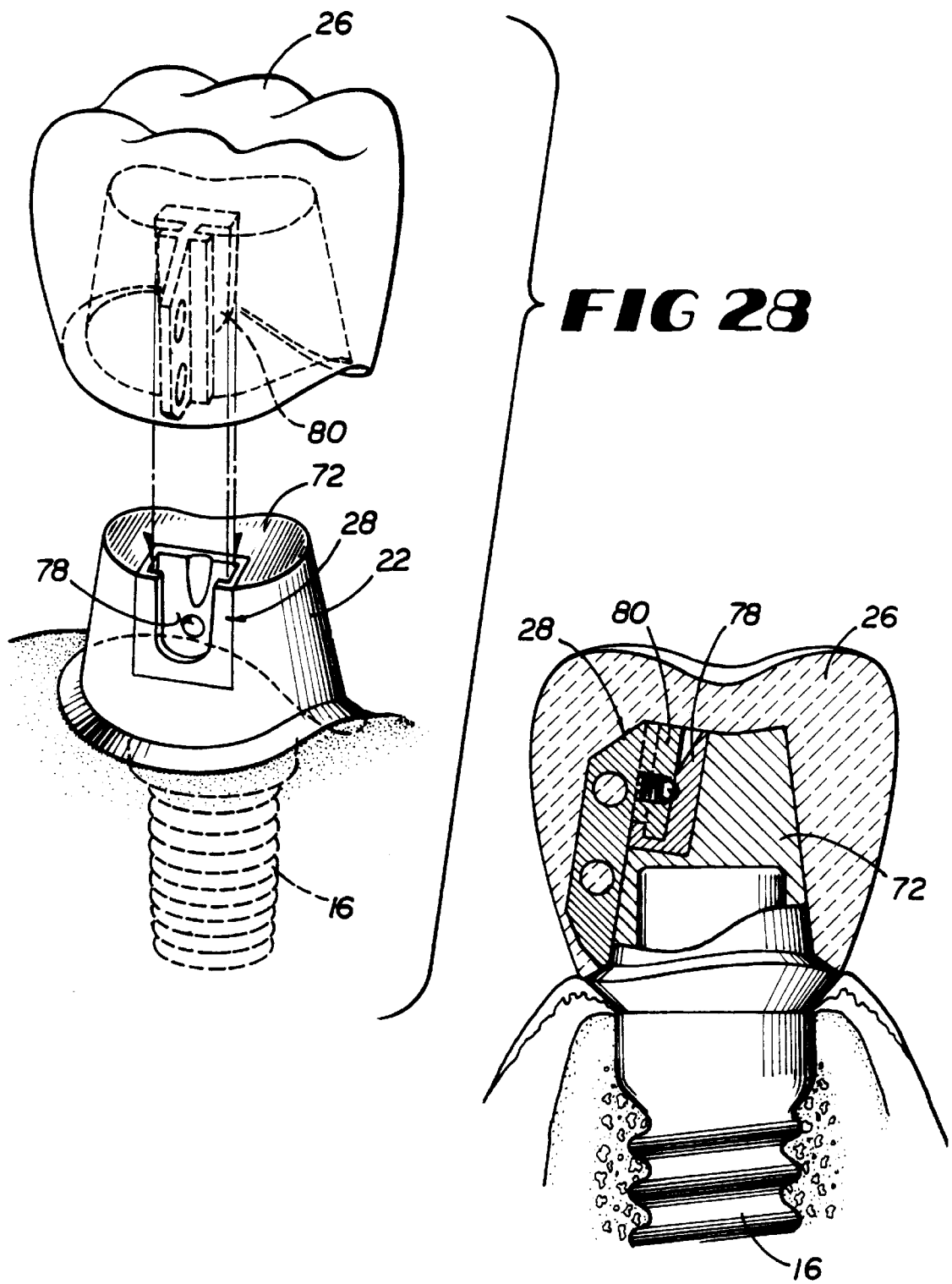

IMPLANT ABUTMENT SYSTEMS, DEVICES, AND TECHNIQUES

This is a divisional of application Ser. No. 08/176,011, filed in the U.S. Patent & Trademark Office on Dec. 23, 1993, now U.S. Pat. No. 5,527,182.

The present invention relates to dental implant abutment systems, related devices, and implantology processes and techniques.

BACKGROUND OF THE INVENTION

Various implant-related devices and systems have been created in recent years in an effort to anchor dental prostheses more directly and flexibly in the mandible or maxilla than was possible using conventional dentures or bridges. Conventional implant approaches have typically employed a pre-manufactured coping or abutment which must be ground by the practitioner or the lab in order to angulate the prosthesis which respect to the implant axis. Obviously, such angulation is limited in systems which require that the screw coupling the prosthesis to the implant be inserted through a bore in the crown.

Such systems typically employ an anchor or "implant" which has been inserted into the bone and from which extends prosthesis-supporting structure typically coupled to the implant using a fixation screw or other desired fastener. All such systems have involved biologic and aesthetic compromises. Bacteria, food and other matter exacerbate corrosion, chronic infection and bone loss. Secure fixation to the implant often requires fasteners that extend from the crown and thus invasion sites for foreign materials as well as distraction to the patient. Conventional such systems also typically feature narrow emergence profiles from the gingival tissue (sometimes exposing metallic structure) which can cause visually and often phonetically adverse aesthetic complications.

To the extent that conventional implant abutment systems employ precision attachments, they do so in a narrow manner, primarily to secure prostheses such as bridges to copings on natural teeth or other anchors. Such attachments have not been conventionally employed to provide patient—removable prostheses, primarily because the abutment designs (usually featuring a central access bore) could or did not accommodate a precision attachment component within the contours of the abutment.

The following is a brief review of some of the conventional implant- and abutment-related references.

U.S. Pat. No. 5,116,225 issued to Riera ("Riera") discloses an angulated abutment system, a pair of bases which are adapted to fit together and with the implant to allow prostheses to be disposed at a large number of predetermined angles with respect to the implant, a screw for mounting the bases on the implant, and a two part abutment system which may be screwed on the bases so that structures supporting the crown may be disposed at various angles relative to the bases. The system thus apparently aims to provide great flexibility in lateral and vertical angulation of the prosthesis with respect to the implant. The Riera system allows for angulation correction in intervals as little as 6 degrees by using a series of six different parts that are sequentially attached ending with a gold cylinder or plastic sheath that, once cast or cast to, serves as the basis upon which the crown is to be built. This device features no means for preventing loosening of the fixation screw, and it requires the laboratory to maintain comprehensive inventories of plastic sheaths, cylinders and other angulated components. Furthermore, the components feature centrally disposed cylindrical bores which would impede inclusion of precision attachment devices for coupling crowns or other devices.

U.S. Pat. No. 5,106,299 issued to Ghalili ("Ghalili") discloses a dental implant system which includes an abutment adapted to connect to upper portions of an implant, held in place using a fixation screw, and upper portions of which are adapted to receive an insert which bears against the fixation screw and a spring loaded device to hold the insert in place so that the fixation screw does not loosen. The crown fits the abutment. The Ghalili abutment, because of its height, permits relatively little angulation of the crown from the implant axis. Furthermore, the central bore of the abutment would interfere with precision attachments or other connection devices for prostheses or crowns. Additionally, the Ghalili anti-rotational pin is exposed on the exterior of the crown, which can introduce hygiene problems, particularly when combined with the relatively complex spring-loaded mechanism of the pin.

U.S. Pat. No. 5,125,839 issued to Ingber ("Ingber") discloses an implant system that includes an abutment held in place on an implant via a fixation screw, and to which a crown may be attached. The fixation screw enters through the top of the crown, which may be filled using resin filler. The Ingber implant assembly, while it facilitates customized formation and fitting of dental prostheses, requires a central bore in the crown for the fixation screw which requires a dental filler and thus impedes aesthetic effects, durability, retrievability, and does not adequately address the issues of screw loosening. Additionally, the requirement of a central bore in the crown to accommodate the fixation screw dramatically limits angulation of the crown with respect to the implant axis.

U.S. Pat. No. 5,104,318 issued to Peshe ("Peshe") once again discloses an implant system which includes an abutment adapted for connection to an implant, with fixation screw for connecting the abutment to the implant, and a separate retainer screw for attaching the crown to the fixation screw and the abutment. The Peshe structure, with its conceptually similar fixation screw and abutment, together with crown bore, presents the same types of problems as Ingber.

U.S. Pat. Nos. 4,854,872 and 5,015,186 issued to Detsch (respectively, "Detsch 872" and "Detsch 186") disclose prosthetic implant attachment systems that include a base member having a lower end adapted to seat on the upper end of the implant, and an upper end of diameter corresponding to profiles of various teeth, a securing device for securing the base to the implant, and various straight and angled or variably angled prosthetic heads attached to the base for supporting the crown. The Detsch 186 attachment system once again features a crown with a centrally disposed bore through which a fixation screw must attach, with the concomitant flexibility, durability, aesthetic problems and screw loosening problems.

U.S. Pat. No. 4,713,003 issued to Symington et al. ("Symington") discloses a device for attaching a prosthesis to an implant. The device includes a fixation screw for insertion in the implant which in turn carries an abutment connected to the fixation screw by a second screw. The abutment may carry a prosthesis, and it may also attach to a prosthesis via a retaining screw received in a threaded cavity in upper portions of the abutment. The Symington system once again requires a centrally oriented bore in the crown.

U.S. Pat. No. 4,780,080 issued to Haris ("Haris") discloses an implant system formed of a root member implanted in the bone and carrying a post in which an angular skewed head may be mounted for supporting a crown. The Haris system relies heavily on dental cement and fails to control rotation of the base with respect to the implant.

U.S. Pat. No. 4,988,298 issued to Lazzara ("Lazzara '298") discloses a dental implant system that contains a precision machined abutment for attachment to an implant and which supports a crown, portions of which are attached to the abutment. U.S. Pat. No. 4,955,811 issued to Lazzara ("Lazzara 811") discloses a dental implant fixture that is non-rotatably connected to an implant and includes a two part impression coping that may be non-rotatably connected to the implant. U.S. Pat. No. 4,850,870 issued to Lazzara et al ("Lazzara 870") discloses various abutment posts and copings for use with implants. U.S. Pat. No. 4,856,994 issued to Lazzara et al ("Lazzara 994") discloses a healing cap for use in dental implantology during healing in gingival tissue. The Lazzara systems are state of the art, but their premanufactured nature impairs flexibility in conforming an abutment and a prosthesis to the gingiva in a manner and at proper angulation to replicate the look and feel of natural teeth.

U.S. Pat. No. 4,318,696 issued to Kasama ("Kasama") discloses an implant system featuring elastic material attached to the head of the implant, together with a crown attached to the elastic material. U.S. Pat. No. 5,033,962 issued to Scatena ("Scatena") discloses an implant system that includes a "stump" which features a lower part or base for connection to an implant, and an upper head which attaches to a cap via an elastic element. The cap supports a crown. The Kasama device correctly addresses the need in certain cases to replicate natural root/ligament-induced articulation in opposing elastic or flexible material between the crown and the implant. The Scatena device also includes an elastic element, but between a cap which supports the crown and a head which fits the implant. However, the Scatena structure appears to include no mechanism for preventing rotation between the head and the implant, and the elastic material is distanced from the bone.

U.S. Pat. Nos. 5,073,111, 5,035,619, and 5,145,372, issued to Daftary (respectively "Daftary 111", "Daftary 619" and "Daftary 372") disclose a system and method for implanting tooth analogues which include a standard implant and a cover screw which may be replaced with a healing cap for healing of the gingival tissue. The healing cap may then be removed and replaced by an abutment having an emergence profile matching that of the healing cap, which abutment is adapted to receive a crown. The Daftary 111 patent healing cap claims to provide frusto conical emergence profile in the gingival tissue more closely simulating that of a natural tooth. It unfortunately provides only a circular cross section gingival cuff, however, and various healing caps of various heights must be inventoried in order to accommodate differing gum thicknesses and desired emergence profile.

SUMMARY OF THE INVENTION

The present invention provides a universal abutment system (and related devices, components and processes and techniques) which includes a base that is adapted to mount in non-rotating fashion on any desired dental implant, together with a fixation screw, which secures the base to the implant. A core, to which the abutment may be cast as desired from an appropriate wax-up, is attached to the base (preferably) in threaded fashion and secured with an appropriate anti-rotational mechanism such as an anti-locking screw, sliding lock or other suitable device.

The core and abutment of devices according to the present invention, unlike the prevalent conventional systems, do not require a central bore in the core component for insertion of the base/implant fixation screw. That significant and distinct feature, plus the relatively small size of the core, provides essentially an open palate for fashioning wax-ups and casting abutments of any desired shape, profile, shape and angulation in order to accommodate naturally occurring tooth profiles. The core, abutment and crown provide prostheses that have the same shape as actual and wax-up teeth both in their exposed and transmucosal portions, for aesthetic and accessibility reasons. Since teeth obviously come in many different sizes and shapes, each wax-up must be customized. This customized capability is not possible with other conventionally premanufactured systems.

Accordingly, the universal abutments according to the present invention permit unlimited vertical and horizontal angulation, and they eliminate any compromise of fixation screw, base or abutment strength caused in previous designs by grinding or heating. The shorter base/implant fixation screw receives less bending movement due to the base/implant surrounding connection and shortened length of the fixation screw relative to the previous design. The system additionally may be easily disassembled and retrieved with no requirement for dental cement. Previous inventory requirements for large numbers of parts to accommodate various prosthesis/implant angulations are no longer desired. The additional flexibility allows greater latitude in selecting emergence of a screw block that connects the crown to the abutment, which now may be located more easily in the cingulum area of the crown.

Abutment systems according to the present design also allow intracoronal precision locking attachment components to be placed in the abutment, which can accommodate corresponding attachment components fixed in the interior portions of a bridge, overdenture or other prosthesis in order to allow the prosthesis easily to be removed and cleaned at will. The precision locking attachments may be aligned on the abutments nearer the implant axis (and the abutments aligned) more easily because no central abutment bore for the fixation screw need be accommodated; the bridge may thus smoothly and passively fit to the abutments. In implementations using a combination of implants and natural teeth, the abutments may contain a resilient core to replicate root/ligament articulation and thus consistent articulation of the prosthesis.

The core and base may be prepared locally via computer aided machining. Computer aided manufacturing devices such as those presently used for crown fabrication may be controlled via data obtained from visual or other appropriate scanning of the mouth in order to mill blanks of titanium or other appropriate material in which appropriate threads, orifices, shoulders and other features have been pre-precision machined to accommodate the base and anti-rotational mechanisms and the precise tolerances of these features required in the present system.

The implantology processes employing these systems is radically different from previous such processes. Very briefly, as discussed in detail below, a first model and first or surgical template are created, and the implants are placed in the mouth to be incorporated in the bone structure for a several month (typically) healing period, as in conventional processes. A second stone model is created with out implants in place and accurate wax-ups are created on this second model. Full anatomical contours of the wax-ups are noted on the model. Their contours are outlined in pencil, the wax-ups are carefully removed, and a clear template is drawn down over the pencilled outline. This second template is cut to correspond to a smaller set of second outlines as disclosed further below. The template is additionally contoured using an angle burr to replicate natural tooth emergence from the gingiva. This "Tapered Gingivectomy Template" is employed to excise gingival tissue in the vicinity of the implant in order to create a tapered gingival cuff simulating a natural emergence profile, and through which the base, core, abutment and crown may extend.

Healing collars are fashioned for the (non-circular profile) gingival cuffs using wax-ups so that the gingival tissue heals corresponding to the desired emergence profile. Appropriate abutments and crowns are created on models all as disclosed in further detail below to be installed in a manner that closely replicates the look and feel of natural teeth.

These systems, devices and techniques are well suited for, among other applications, patient removable bridges, overdentures, other prostheses and virtually any implant-based dental restoration.

BRIEF DESCRIPTION OF THE DRAWINGS

FIG. 2 is an exploded cross sectional view of a UAS assembly according to the present invention.

FIG. 3 is a cross sectional view showing the UAS assembly of FIG. 2 after placement.

FIG. 4 is an exploded cross sectional view of a UAS assembly according to the present invention whose interlock structure with the implant differs from that of the assembly shown in FIG. 2.

FIG. 5 is a cross sectional view showing the UAS assembly of FIG. 4 after placement.

FIG. 10 is a perspective view showing the components of FIG. 9 in place.

FIG. 11 is a perspective view showing the components of FIG. 10 being fit with a crown.

FIG. 14 is a perspective view of a blank which may be used to mill a MUAS.

FIG. 15 is a perspective view of the blank of FIG. 14 from an upper aspect.

FIG. 16 is a schematic view of a computer aided design device which may be used to design and prepare a MUAS.

FIG. 16A is a schematic view which shows an abutment contour in an actual blank corresponding to the image on the screenface of FIG. 16.

FIG. 18 is a perspective view of a MUAS blank that employs a sliding lock rather than a locking screw.

FIG. 19 is a perspective view of a second embodiment of a MUAS blank that employs a sliding lock rather than a locking screw.

FIG. 20 is a perspective view of a third embodiment of a MUAS blank that employs a sliding lock rather than a locking screw, which includes a resilient core.

FIG. 21 is a schematic view of a blank according to FIG. 19 with the contour of a desired abutment.

FIG. 22 is a schematic view of the blank of FIG. 21 partially disassembled.

FIG. 26A is an exploded cross sectional view of a Flexible Modified Impression Coping according to the present invention.

FIG. 26B is a cross sectional view of the Flexible Modified Impression Coping of FIG. 26A being syringed with material to form an impression.

FIG. 28 is an exploded perspective view of a UAS fitted with a precision attachment according to the present invention.

FIG. 29 is a cross sectional view of the UAS of FIG. 28 that has been placed.

DETAILED DESCRIPTION

Figure 1:
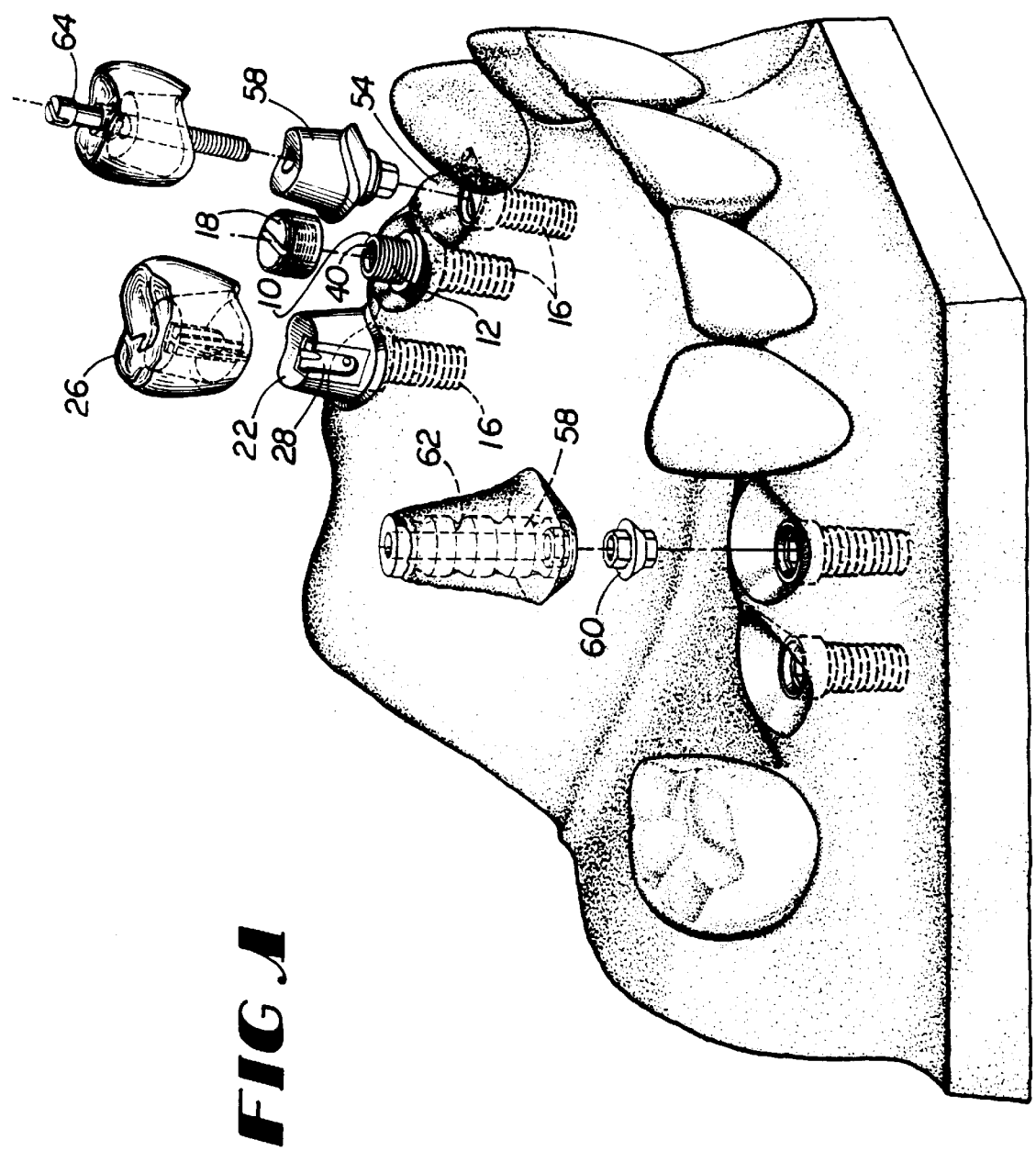
FIG. 1 is a perspective view of a dental model showing a number of components according to the present invention, including a Universal Abutment System ("UAS") assembly, a Universal Abutment System implant-base-core assembly, a temporary that includes a Locking Healing Collar to which a temporary abutment has been cast, and a Locking Healing Collar.

Section I: Context: Reevaluating Progressive Bone Loading Context Part 1: Progressive Bone Loading And the Issue of Stage II Uncovery.

The majority of root form endosteal implant literature suggests that implant mobility is directly related to the anatomic location of the implant during the first year of prosthetic loading. Implant mobility is also related to bone density, implant size, surgical approach and premature loading of the implant prosthesis. The ratio of the prosthesis' height and width to the implant length is another important factor. New techniques of progressively bone loading an edentulous space, especially a full arch are, however, necessary to address more completely the issue of implant mobility and longevity.

This Section I discloses new techniques for progressive bone loading in the edentulous arch which employ a more accurate manner of registering, verifying and transferring the vertical dimension, centric relation occlusion and anterior guidance from the temporary prosthesis to the permanent prosthesis. This is achieved by using UAS according to the present invention as disclosed further below in Section III and MUAS in Section V. This Section also addresses the effect of elevating the periosteum at state II uncovery on the ability of the bone to recover from premature occlusal loading.

Also addressed is the issue of bone maturation and premature occlusal loading. According to Wolff's law, trabecular bone places and displaces itself relative to the forces to which it is subjected. Therefore, the progressive bone loading of endosteal implants is an accepted protocol because it allows immature woven bone (often present at the implant-bone interface upon placement) to be slowly replaced with a more dense load-bearing lamellar bone. It is the presence of this denser lamellar bone and an increase in the amount of bone at the implant-bone interface that reduces the amount of implant mobility, especially during the first year of implant placement. In fact, complete bone maturation requires twelve to eighteen months from the time of initial placement and this is all the more reason why the wear time of the interim prosthesis should be extended.

Unfortunately for many patients, the clinician often races to see how quickly and with how few appointments the permanent prosthesis can be delivered. For example, the average full arch implant case is restored 2–3 months after recovery and in as little as 6 or 7 appointments. This practice is likely, however, to lead to detrimental long-term effects, not only on the implant-bone interface, but also on the patient's temporomandibular joints and surrounding musculature.

In order to make better sense of the following technology and these new techniques, this Section progresses through a hypothetical case; it also discloses an alternative method of rehabilitating the patient's occlusion using this technology.

A new technique has also been developed to prevent the unnecessary loss of peri-implant bone as the result of a Stage II full periosteal flap. The technique involves the use of a tapered gingivectomy procedure that not only offers a less invasive method of implant uncovery but also offers the means to create fully anatomically contoured soft tissue emergence profiles. The effects of this technique are obviously beneficial: Elimination of the need to disturb the periosteum means that the tissue heals faster, the underlying bone is not deprived of its blood supply and therefore the bone remains healthy and can be loaded sooner. Moreover, prosthetics can be contoured more accurately and readily to resemble natural tooth contours.

The key to progressive bone loading is to allow for a controlled loading of the implant-bone interface. This cannot be done if the clinician is peeling back the periosteum to expose the implants and place healing collars, for the act of peeling the periosteum off of the bone leads to a decreased blood supply. It takes many months before the periosteum reheals and its blood supply to the underlying bone is completely regenerated. If during this healing phase the implants are prematurely loaded, the surrounding bone is unable to absorb the occlusal forces because it is not receiving an adequately nutrient-rich blood supply. This leads to microfracting of bone, osteoclastic activity, cortical cratering and even avascular necrosis which appears clinically as bone loss, cupping of bone around the neck of the implant and even mobility in extreme cases. Avoidance of flapping of the periosteum and a slower more controlled progressive loading of the implant could induce more predictable clinical results and less bone loss. Furthermore, proper progressive bone loading allows more time to be spent developing the appropriate occlusal scheme and because a split frame index can be utilized for this purpose, the patients' occlusion can be more accurately recorded and reproduced in the final prosthesis.

The Steps in Progressive Bone Loading

With the technology of the present invention progressive bone loading can begin shortly after implant uncovery because the periosteum is usually not elevated.

The first commonly accepted step in progressive bone-loading is the placement of healing collars which allow for soft tissue healing, formation of the transmucosal cuff and occlusal loading.

In situations where the prosthesis is to be fixed into the patient's mouth, a tapered gingivectomy is required (see Section IV) and therefore the healing collars must be customized. In the fully edentulous situation the prosthesis can be made patient precision attachment removable and so healing collars with tapered transmucosal cuffs are not required. In either situation healing collars must be placed but should not be directly loaded by any prosthesis for the first few weeks. This time period can, however, vary quite significantly.

When the healing collar is placed, the periosteum is not elevated, and tissue healing will take only 2–3 weeks; if the periosteum is elevated, healing will take 6–8 weeks. Therefore, if for no other reason than the time factor, every effort should be made not to elevate the periosteum at the time of implant uncovery.

However, many clinical cases are less than ideal. For example, when tissue guided regeneration procedures are used to augment bone around the implant, bone can grow right over the top of the implant cover screw during integration. The result is often difficult access for the tissue punch. In this situation a conservative internal flap design may be indicated to gain sufficient access in order to remove the necessary bone. If this procedure is required, the periosteum must be allowed to heal completely (which takes 6–8 weeks) before the tapered gingivectomy is performed and the healing collar is placed. It is absolutely imperative that the implant-bone interface not be loaded for this 6–8 week period if the periosteum has been disturbed.

It has been said that the healing cap should seal and be of the same diameter as the outer part of the implant to prevent soft tissue ingrowth. Unfortunately, this frequently leads to the formation of a standard straight transmucosal cuff. It is the inventor's belief, however, that the transmucosal cuff should be surgically tapered and then further modified by both the healing collar and the final abutment to create a completely customized tapered transmucosal cuff in all but the patient removable situations. This procedure provides a way of accurately creating natural anatomically correct soft tissue emergence profiles for the overlying prosthesis. This, in turn, allows the prosthesis to be contoured in such a way that it too reflects the anatomical shape of the natural teeth. Up until now, there have only been a limited number of ways in which to create fully contoured crowns. This usually involved overexpanding and crushing the tissue, ridgelapping or by using symmetrical tapered healing abutments. Overexpanding the tissue without first surgically tapering it according to the present invention creates gingival clefting, sloughing of tissue and recession. Ridgelapping causes plaque accumulation leading to peri implantitis and the frusto-conically shaped tapered healing abutments from some companies require periosteal elevation and create symmetrical soft tissue profiles. As will be seen in more detail later, in order to create more anatomically correct soft tissue contours without elevating the periosteum, crushing the tissue or ridgelapping, an accurate surgical template is needed to first carry out the tapered transmucosal gingivectomy. Then, the healing collar must have a custom tapered capability in order to expand the tissue slightly and hold the tissue to its correct shape during healing. These two components are sometimes referred to herein as a gingivectomy template and a custom locking healing collar.

The tapered peri-implant sulcus or transmucosal cuff can also be modified by the final prosthesis as well; therefore, an abutment that can be flared and customized in terms of its emergence profile must be used. Conventional UCLA abutments cannot be used to create this flare, because, as discussed below, they cannot overcome the screw loosening and central access bore problems. With the universal abutment systems of the present invention (sometimes hereinafter, "UAS"), which maintain exact tissue contour, these problems have been eliminated. Advantages of these systems include: (1) hygienic access; (2) better aesthetics; (3) natural crown contours to help eliminate phonetic problems and food impaction and (4) an anti screw loosening capability. The systems are described further in Sections III, IV and V.

In the edentulous jaw, tapered transmucosal cuffs are not necessary to create hygienic access because of new and innovative removable precision attachment prostheses according to the present invention which allow the patient to remove crown and bridge appliances and expose the individual abutments for periodontal cleaning. In order to illustrate the new principles of design and technique, consider an edentulous maxilla opposed by a partially edentulous mandible when four implants replace the missing lower molar teeth and six implants are present in the upper jaw. With existing systems it is common practice at the second appointment (3–4 weeks after flapping the tissue) to replace the healing caps with the abutment of final size and height. However, this is far too premature because even though the gingival tissue around the healing collar may have healed, the underlying periosteum has not (not for at least another 3–4 weeks). Therefore, if a clinician chooses to use this standard technique, all that should in fact be done at this second appointment is to take an analog transfer impression in order to prevent damaging the periosteum.

With modified impression copings according to the present invention as disclosed below, the analog transfer impression can be accomplished at the first visit because the periosteum has not been elevated. As discussed in Section IV below, modified implant analogs can be attached to these modified impression copings so that they not only provide an implant analog transfer which duplicates the precise axial and rotational position of the implant, but they can also be used in non-patient removable cases to capture the tapered gingivectomy contours in the same impression. This can all be accomplished at the first appointment which also allows the temporary to rest more sturdily on the locking healing collars after an appropriate period of initial healing. Most importantly this can be achieved without elevating the periosteum.

It is also important to remember that the locking healing collars according to the present invention have the ability to be lab altered and individually customized. In the edentulous situation it is not necessary to incorporate a tapered transmucosal component because the overlying prosthesis, even though it is ridgelapped and overcontoured, can now be made patient removable for hygienic access according to the present invention. Furthermore, locking healing collars of the present invention are less likely to loosen than the standard screw-in healing collar because of their design which prevents soft tissue impingement between the superior edge of the implant and the base of the healing collar. This is a very common problem with existing healing collars which plagues clinicians and causes them routinely to perform unnecessary and avoidable gingivectomy procedures in order to remove excess tissue tags.

With conventional systems, usually only 1–4 weeks is required before the third appointment. At this stage most clinicians undertake the prosthetic reconstruction of the edentulous arch. The inventor believes this is far too soon, using existing techniques, because not only has the periosteum barely had time to heal completely (by this point a maximum of seven weeks will have passed since uncovery), but the inventor also believes that insufficient attention has been given to establishing the temporary occlusion and bone loading the implant-bone interface. Why do some consider the occlusion in the permanent prosthesis so critical and not the temporary? After all, how stable is a denture occlusion if it is anchored to a non-passive fitting tissue bar and a softlined denture, especially if the reconstruction is being rushed and has been placed on top of freshly elevated periosteum? Perhaps these are some of the reasons behind unexplained implant loss. Approaches of the present invention to full arch implant reconstruction, by contrast, permit initial reconstruction of a stable interim prosthesis after the first appointment without elevating the periosteum. The reconstruction takes several appointments to complete and is then left in place for a minimum of 3–4 months to progressively bone load the implant bone interface.

In an edentulous situation when the clinician is reestablishing the centric relation at the correct vertical dimension of occlusion (centric relation occlusion) and with all the appropriate centric and eccentric contacts, their accurate registration cannot be established by standard aesthetic and occlusal try-in procedures. In fact, unless the interim prosthesis can provide a stable reproducible set of registrations the clinician is unwittingly and arbitrarily setting the occlusal pattern for the final prosthesis. This can have profound longterm effects on the surrounding musculature and TM joints. It is not enough simply to take "occlusal try-in records" and then have a metal framework fabricated while adjusting the temporaries and placing them into occlusion. There must be a way of verifying that the final prosthesis accurately duplicates the same occlusal determinants as established by the interim denture. The interim denture cannot simply be removed and then the framework tied in because then all the centric stops are lost, and the clinician is left "lost at sea".

As stated earlier, many clinicians feel that 1–4 weeks after occlusally loading the temporary, the patient can receive the final implant supported prosthesis. The inventor believes that this seems an awfully large leap of faith; after all, one wonders whether this is really long enough to leave a temporary prosthesis before determining whether the TM joints musculature and occlusion are stable and asymptomatic, not to mention whether or not aesthetic and hygienic concerns are being met or whether the implant-bone interface circulation has totally rehealed. If these concerns are not being adequately addressed then how can a so-called permanent prosthesis be created? Do not forget that in the partially edentulous or single tooth situation where there are preexisting stable centric stops, establishing a CRO position and progressively bone loading the implants is not as complicated, simply because the patient's natural dentition can be utilized.

Context Part 2: Using an Interim Denture and a Split Frame Index: A New Technique for Accurately Registering, Verifying and Transferring an Edentulous Patient's Occlusal Determinants.

Figure 39A:
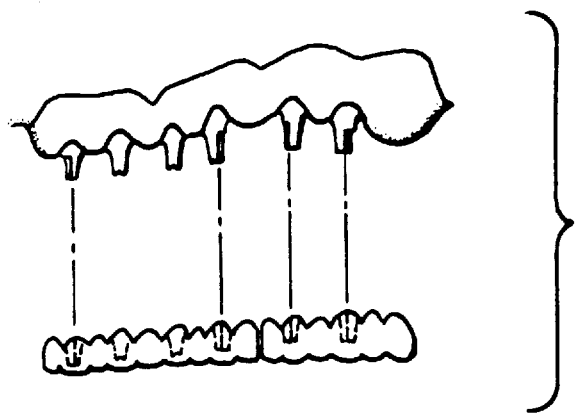
FIGS. 39A and 39B, 40A and 40B are schematic diagrams showing steps in a split frame index process according to the present invention.
Figure 39B:
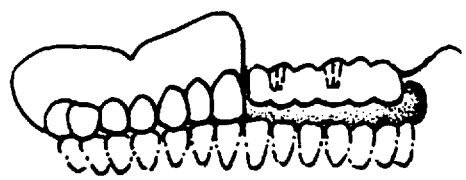
Figure 40A:
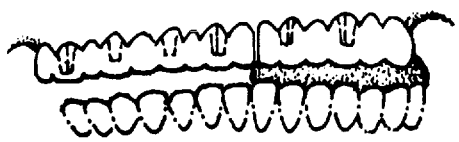
Figure 40B:
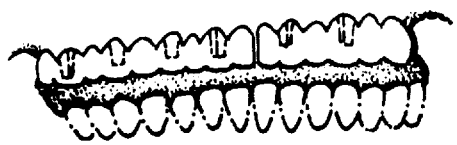
Figure 41:
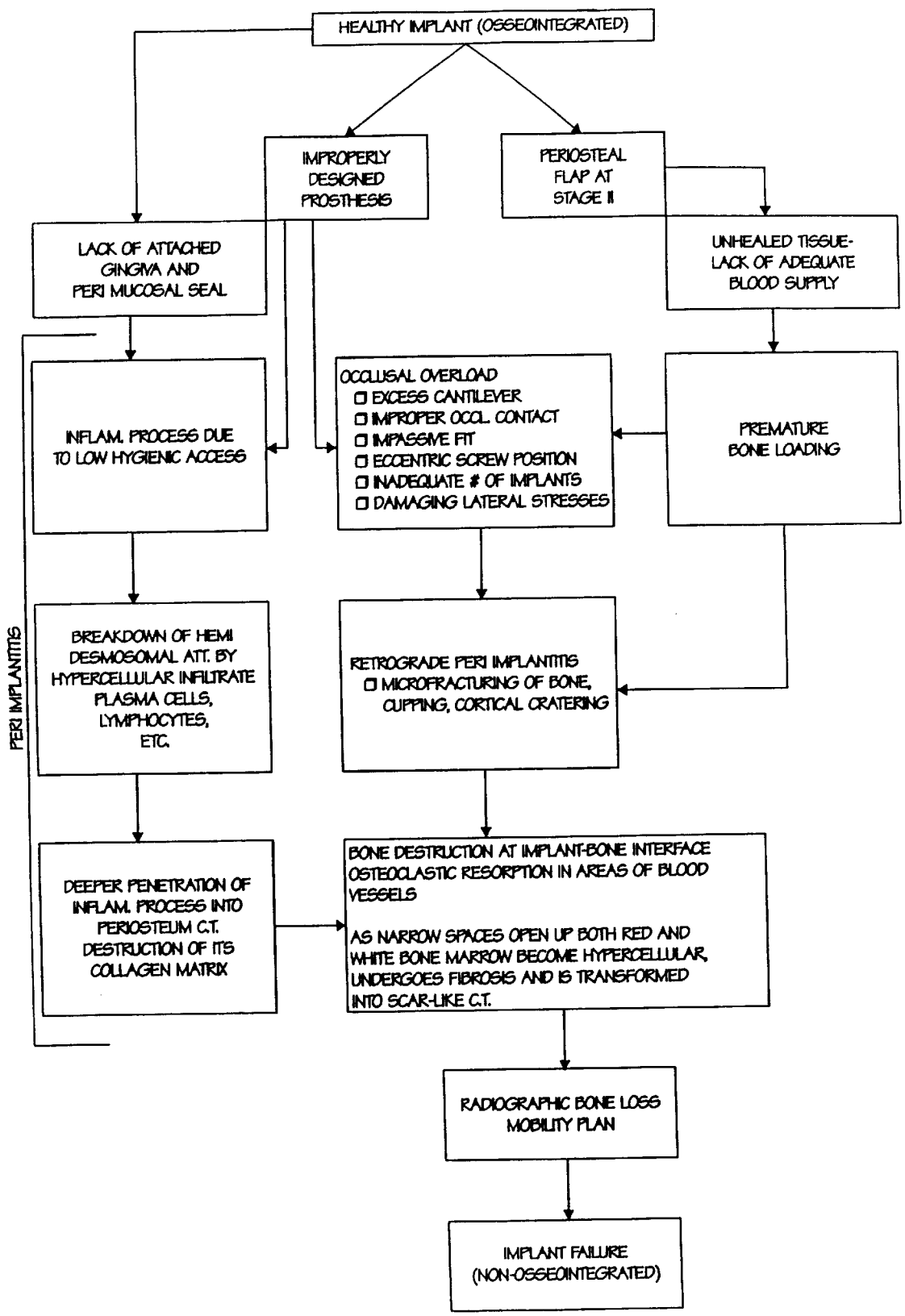
FIG. 41 is a flow chart showing analysis of suitability of devices and processes according to the present invention.

A split frame index technique has been developed according to the present invention in conjunction with a unique interim denture in order to (a) control the progressive bone loading of the integrated implant, and (b) aid in accurately registering, transferring and verifying centric relation, anterior guidance and vertical dimension of occlusion in an edentulous patient. FIGS. 39 and 40 (39A and B, 40A and B) schematically show steps in the process. The use of precision attachments mounted within the normal abutment contours of the present invention allows very accurate positioning and repositioning of the interim prosthesis. The split frame index technique utilizes one-half of the interim denture in order to hold the bite while the left half and then the right half of the final precision attachment framework (also part of the present invention) is used to record, transfer and verify the correct occlusal positions.

In the full arch situation, the interim denture fabrication can begin at the first appointment (the implant uncovery appointment) with a try-in of the stabilized acrylic bases loosely fitted over top of locking healing collars in the mouth. These stabilized bases are modified at this first appointment to fit down over the lubricated sleeves of the locking healing collars. The sleeves are made of plastic according to the present invention and can be adjusted for draw (path of insertion). Acrylic can be flowed around the sleeves of these healing collars to increase the fit and stability of the bases.

This provides the same type of passive fit that the conventional KAL technique claims in a permanent prosthesis, but because they both have the same problems with screw loosening, this approach provides a more than adequate temporary solution but certainly not one that can be carried over into the permanent fixture. While the interim denture is being fabricated, the patient uses their old denture which is secured to the locking healing collars with a soft liner.

Occlusal rims can be fabricated using greystick compound and by applying neutral zone principles. Centric relation occlusion is registered in the edentulous case by an inter-occlusal centric relation bite record. A facebow transfer record could then be taken to help mount the casts. Tongue and cheek matrices can be taken and trimmed back to the exact height of the occlusal plane. This is all done at the second appointment. The accuracy of the mounting should then be verified by using a separated cast technique. Upper anterior teeth can then be set in accordance with anterior guidance principles for the natural dentition, even though they may be modified at a later date to redistribute the occlusal load.

The interim anterior set up is tried in at the third appointment and a determination of the precise upper incisal edge location is made. The anterior teeth can then be set more firmly in acrylic which requires an additional lab procedure involving fabrication of a matrix. Only after this has been done can all excursive pathways from centric relation to an edge to edge relationship be check and adjusted. At this next (fourth) appointment an adjustment for long centric can also be made. A centric occlusal bite record should also be taken in the posterior segments at the correct vertical dimension (determined by solid anterior tooth contact) and then the anterior try-in denture can be remounted on the articulator. The patient's old relined dentures are re-inserted and the patient is instructed to remain on a soft diet. Before the fifth appointment and only if all anterior guidance contours are definite can the clinician finish restoring the lower posterior teeth.

The use of a Broadrick Occlusal Plane Analyzer is helpful in setting an ideal curve of Spee and curve of Wilson. At this point the position of both the buccal and lingual cusp tips and their appropriate contours should be determined. This can be done by fabricating acrylic temporaries on top of universal abutment systems of the present invention and grinding of the lower buccal cusp tips to match the exact line and plane of occlusion. The upper posterior teeth can now be set on the interim denture using 30° inclined plane denture teeth so that only the lingual cusp tips engage the lower fossae. At this stage, both the lingual cusp tips and the fossae contours of the lowers may have to be altered as well. A narrow occlusal table should be created to help reduce damaging lateral stresses and occlusal forces. At this time the patient may be brought in for another try-in.

At the sixth appointment, the lower posterior implant supported temporaries can be cemented in and the maxillary interim denture can be tried in. When the try-in is acceptable, the interim denture is processed and new tongue and cheek matrices of the interim denture are mounted on the working models and finalized contours can be set for the UAS abutments. Careful attention is paid to allowing sufficient clearance for the framework and crowns that fit overtop of the abutments. Precision attachment housings are then resin-bonded into place in the appropriate implant abutments of the present invention according to resin bonding techniques of the present invention. Once the processed interim denture has been remounted on the articulator, its underside can be hollowed out so that the implant abutments can be properly positioned without interfering with the denture. This hollowed-out space is created around each abutment so that when patrix analog components according to the present invention are inserted into female matrices, acrylic can be flowed into the denture and around the patrix analog flags. In order to assure a passive fit, this procedure should be done intraorally. Once the acrylic has set, the interim denture can be detached from the patient's mouth.

This assembly is not only patient removable but it also provides a very accurate and very stable interim denture. This is a tremendous help when trying to duplicate in the mouth the same occlusal markings created on the articulator. This usually means that the denture is created with a bilaterally balanced occlusion and no excursive interferences. When the clinician is satisfied with the aesthetics and occlusal patterns, impressions can be taken off both arches and the models remounted for later comparison.

The patient should be left in the interim prosthesis for 3–4 months to allow for adequate bone maturation around the implants and occlusal analysis. The patient should also be reminded to maintain a soft diet and instructed on how to remove the interim denture and clean around the abutments. A rotadent or a hydrofloss machine is ideally suited for this purpose.

By the fifth appointment, most clinicians have already delivered the final prosthesis. However, the inventor believes they have done so by (1) arbitrarily setting many of the patients' occlusal determinants, and (2) rushing the progressive bone loading. Therefore, the long-term health and stability of the patients' gnathostomatic system is questionable.

On the other hand, with the implant supported precision attachment interim dentures according to the present invention, everything is made to be stable and reproducible before the definitive prosthesis is fabricated, which gives the patient 3–4 more months of progressive bone loading. After this maturation phase is over, if the patient's TM joints and surrounding musculature are comfortable and pain-free, and the aesthetics and phonetics are acceptable, a final set of records is taken to mount the interim denture and the abutment back onto the articulator and the patient is given their old denture which is anchored to place by the locking healing collars. Then, and only then, can the final prosthesis be fabricated.

The inventor, as well as other notable clinicians such as Dr. Peter Dawson, believes that stable reproducible records cannot be transferred accurately from the interim denture to the final prosthesis without being verified intra-orally. The only effective way to accomplish this for the edentulous implant patient is by using a technique referred to herein as the "split frame indexing technique." This technique is employed to help determine and verify anterior tooth position at the correct vertical dimension. Dawson states that "anterior guidance is a proper determinant of posterior occlusal form" (P. E. Dawson, *Evaluation, Diagnosis and Treatment of Occlusal Problems* ch. 16 (C. V. Mosby Co. 2d ed. 1989) and the inventor believes that with the split frame index the appropriate posterior occlusal contacts can be accurately produced, once the anterior guidance has been established.

Split frame indexing is a technique that has been developed in order to ensure that once the interim implant denture has been fabricated with the proper occlusal determinants, aesthetics and hygiene access, these features can be accurately recorded, verified and duplicated in the final implant prosthesis.

Before the seventh appointment, the patient's interim denture is sectioned completely in half (preferably using a fine diamond disc). Both halves of the interim denture remain stable because they are secured via precision attachments to the implant abutments. The lab is now instructed to fabricate a precision attachment framework. This framework is made in two pieces that are later resin-bonded or screwed together. (See Section VII.) Again, the tongue and cheek matrices are used to help provide the framework with adequate clearance for porcelain application. In fact, the porcelain application waits until after the split frame index has been taken and verified and usually involves telescoped crowns or sections of crowns that are lingually set-screwed into place.

At the seventh appointment, the split frame index is created. The first step is for the framework to be tried in, in two pieces, and then to have the male patrices resin-bonded into the framework while they are rigidly attached to the implant abutment matrix. Both sections of the framework are then removed. The right half of the interim denture is inserted and attached securely to the abutments. The left half of the precision attachment framework is also secured into place. An index of duralay is then taken on the left side while the patient is fully intercuspated into the right side of the interim denture. The left split frame index is now complete and it is checked and verified for accuracy by inserting thin film articulating paper between the opposing natural teeth and the interim denture.

The right half of the interim denture is then removed leaving the centric relation occlusion position held by the left split frame index. The right half of the precision attachment framework is then secured to place in the mouth. The entire precision attachment framework should now be resin-bonded or screwed back into one piece. The patient is asked to close down into the left split frame index which is mounted on the top of the left half of the precision attachment framework. A duralay record is simultaneously taken on the patient's right side. The right split frame index is now complete and is checked for accuracy. The entire framework and the implant abutments can now be removed from the patient's mouth and the abutments are then screwed back down to place on the master model. The precision attachment framework is then reseated on the model where the accuracy of the right and left indexes are verified. The patient is given their old relined denture and healing collars until the porcelain crowns have been fabricated.

The split frame technique in essence allows the information contained in the occlusal records to be accurately transferred from the temporary prosthesis (interim denture) to the permanent prosthesis and then verified without arbitrarily setting the vertical dimension, anterior guidance or the centric relation occlusion of the patient. This technique also allows for a slower, more gradual progressive bone loading of the bone-implant interface. This results in more healing time for the bone (in which the implant is embedded) and allows the bone to mature.

The split frame technique utilizes the framework of final prosthesis in conjunction with the interim denture to record and transfer occlusal determinants. One-half of the final framework is placed intra-orally with the adjacent half of the Interim denture securely in place to "hold the bite". A bite record is taken overtop of the final framework to duplicate the position of the interim denture. The interim denture is then removed and the other half of the final precision attachment framework is placed intraorally. A second bite record is taken overtop of this half of the framework and it now duplicates the first half. In effect, the interim denture has been used to "hold the bite" while accurate records can be developed on the final framework. When the records are acceptable, the two halves of the final frame can be resin bonded together. The split frame technique and interim denture are especially suited to use with UAS and NUAS components of the present invention, because they do not require central access bores (which prevent true axial loading of the attachments and in fact preclude their use).

Context Part 3: Occlusal Considerations and Completing The Case.

The clinician now has a very accurate mounting for final porcelain application but because both the framework and the patrix portion of the attachment have been resin-bonded into place, direct porcelain application is not an option as the heat of the porcelain oven would destroy the resin bonds. Therefore, there are only two practical alternatives. First is to veneer the framework with a resin material such as Isocit. The advantages of the Isocit are that (a) if it is ever damaged it is easily repaired, (b) it is lighter than porcelain, (c) it is more flexible than porcelain and therefore when the framework bends this material it is less likely to break off (a common problem with porcelain), (d) it need not be baked on in an oven, thereby eliminating potential temperature distortions, and (e) the Isocit is a good "shock absorber" during the first 1–1½ years of bone maturation. The second alternative is to fabricate telescopic crowns or sections of crowns with lingual set screws that can be fabricated separately from the main framework. This second option also has many advantages including the fact that porcelain is more aesthetic and more durable than Isocit. Secondly, if a porcelain crown is chipped, that crown or section can be removed and repaired without having to refire the entire bridge. This is an excellent example of the ideas and principles behind prospective planning.

Once the choice has been made as to which type of material will be applied to the framework, the condylar paths of the articulator can be arbitrarily set to 20° horizontal and 15° vertical. This ensures posterior disclusion and allows the anterior guidance to be accurately developed in the porcelain. As Dawson states "posterior occlusions that relate to a correct anterior guidance will automatically disclude in excursions if condylar paths are steeper than those on the articulator." P. E. Dawson, *Evaluation, Diagnosis and Treatment of Occlusal Problems* 274 ch. 16 (C. V. Mosby Co. 2d ed. 1989).

Lower posterior teeth are completed and inserted at appointment eight, then the ninth appointment is scheduled for the following purposes: First, an anterior porcelain try-in of the precision attachment framework; and second, recordings for a functionally generated path (FGP) which accurately records the precise border pathways that the lower posterior teeth follow as dictated by condylar guidance and anterior guidance. This anterior porcelain try-in proceeds with the precision attachment framework firmly in place. Centric and eccentric movements are checked carefully and then one final record is required at the correct vertical dimension, but before this record is taken adequate posterior clearance must be confirmed (2 to 2.5 mm) between the framework and the opposing dentition in all excursions to allow for adequate final coping thickness and porcelain coverage.

This centric record is an excellent method of verifying the accuracy of the articulated models. Once again, this is something that is conventionally not done routinely by clinicians because the anterior try-in step is frequently skipped altogether and therefore the centric record cannot be taken at the correct vertical dimension.

Assuming that the record is accurate, the FGP record can now be taken. In many instances of full upper arch rehabilitation with implants, facial ridge resorption creates implant and subsequently tooth angulations that result in rather flat anterior guidance patterns. This feature makes it difficult to develop posterior disclusion, at the moment of lateral anterior guidance, without accurately recording the border movements of the lower posterior teeth. Immediate disclusion of the posterior teeth at the moment of lateral anterior guidance is extremely important, for recently it has been linked to a significant decrease in elevator muscle activity. This decrease in activity means that there is less force being placed on the anterior component of the occlusion and therefore less stress on the implant-bone interface.

To ensure that the upper posterior teeth disclude, the inclines of both buccal and lingual cusps are relieved so that only the centric stops of the fossae and lingual cusp tips make contact with the functional core. At this point, a matrix is made of the completed maxillary posterior wax-ups. The wax patterns are then cut back to provide for porcelain application. It must be remembered that these wax patterns form individual copings on the precision attachment framework of the present invention and are screw retained by lingual set screws. The wax-ups are cast and then refitted to the main framework. The matrix serves as an index for porcelain buccal tip location. Once the buccal cusp tips are located, the rest of the contours are readily achieved.

Balancing incline interferences are carefully checked and eliminated—this is easily done later on in the mouth. Once all the adjustments have been made, the tenth appointment is made for delivery of the final prosthesis. At this appointment the patient is reinstructed in oral hygiene, and a continued soft diet is emphasized for at least three months. The patient is seen periodically after this to assess implant mobility and soft tissue response, because these cannot be overemphasized as to the importance of gradual progressive implant - bone loading.

As an alternative to assembling the final prosthesis with universal abutment systems according to the present invention, other abutments such as modified UAS or MUAS with resilient cores can be placed. This allows for even more control over the progressive bone loading during the first year to year and a half when the bone is undergoing its critical remodelling and maturation phase. Without the UAS or MUAS, these types of prosthetic reconstructions are not possible.

Context Part 4: Summary

With all the intricacies of implant prosthetic design, clinicians frequently lose sight of the "overall picture." The focus must be constantly redirected not only to deal with the effects of progressive bone loading at the implant - bone interface but also the effects that prosthetic designs can have on the entire masticatory system. Allowances must be made in the prosthetic protocol to take into account the effects that these full arch appliances can have on the TM joints and musculature. More time must be devoted to correcting any discrepancies in the temporary appliance before irreversible changes are carried over into the final prosthesis.

A recent study by Hongchen, Filin and Ning has clearly pointed out "that the position of the condyles in the glenoid fossa may change in the edentulous patient" as the vertical dimension of occlusion is lost. L. Hongchen, Z. Filin and L. Ning, *Edentulous Position of the Temporomandibular Joint*, 67 J. Prosthetic Dentistry 401–04 (No. 3, Mar. 1992). This "edentulous position of the TMJ" can be potentially pathologic. It is therefore crucial as Hongchen, et al. point out to "correctly determine the vertical dimension of occlusion and intercuspal position, not only for the function and aesthetic value of a denture, but also for the proper position of the condyle within the glenoid fossa to prevent TMJ disorders." Id.

Once this position is established it must be maintained accurately and must be readily verifiable. Therefore, the idea of placing the patient in an "occlusally correct" interim prosthesis has merit.

For the edentulous patient, the interim prosthesis plays a very important role; it is the cornerstone to a successful full arch rehabilitation. Unless a stable interim denture is provided "you are lost at sea" and will end up approximating and arbitrarily setting centric relation occlusion and anterior guidance. In order to create a stable interim denture UAS or MUAS of the present invention must be utilized and more time must be taken before an accurate assessment of the health of the TMJ and musculature can be made. This allows for a slower, more progressive bone loading and more time for the bone to mature.

In order accurately to take records, transfer them from the mouth to the articulator, and then back to the mouth in the form of a final prosthesis, the temporaries must be stable. This is why the use of the interim denture is so very crucial. Furthermore, without the interim denture the split frame technique serves no purpose. The advantage in the edentulous situation of using both the interim denture and the final framework as part of the split frame technique is that it helps the clinician maintain solid reproducible centric stops.

If the condyles have been seated superiorly in bone to bone contact with the Glenoid fossa and the jaw is cradled and held in this position, removing one-half of the interim denture will not create any tendency for the condyles to rotate, translate or for the jaw to overdose. The split frame index can therefore be considered a viable alternative method for accurately registering, transferring and verifying the patient's occlusal scheme.

Section II: surgical Corrections of Ridge Deformities In Association With Implant Placement: Bony and Soft Tissue Augmentation

Part 1: Introduction

Dental implants are fast becoming an acceptable mode of tooth replacement; however, many of the edentulous spaces where implants are either placed or planned have an associated ridge deformity. This problem has been extensively detailed in the literature. Ibboth, Kovach and Mann state that: "Ideally a cross-sectional dimension of soft tissue to bone similar to the one found in a natural tooth should be seen . . . but as well as plate collapse occurring after loss, the authors have observed ridge effects that were related to traumatic tooth loss, surgical extraction, apical surgery and scarring from various surgical procedures." Ibbott, Kovach and Carlson-Mann, *Surgical Correction for Esthetic Problems Associated with Dental Implants*, 58 C.D.A.J. 561–62 (No. 7, July 1992).

Unless these soft tissue or bony defects are corrected the final implant prosthesis will be over- or undercontoured, and aesthetically as well as functionally it will lack a normal anatomical appearance. This can greatly affect the patient's ability to cleanse the prosthesis as well as pronounce certain words. It is therefore critical that associated ridge defects be surgically corrected in order to create full anatomical contour so that if tapered gingivectomy procedures according to the present invention are required, they can be performed, or if ridge lapping is required, it can be done without creating an excessively overcontoured prosthesis.

Ridge lapping is a very common way of dealing with aesthetic problems, as will be detailed below. The tapered gingivectomy procedure is a new method according to the present invention of creating anatomical contours but it too sometimes requires prior surgical correction of defects.

Part 2: Correcting Soft Tissue Defects.

A transepithelial collar of minimal height, shallow sulcular depth and a circumscribed border of bound down keratinized tissue are all essential ingredients in allowing for conventional plaque control measures.

If there is a lack of attached gingival tissue or flattened papillae then it is the surgeon's job to recreate normal gingival contours and an appropriate amount of attached mucosa. Gingival onlay grafting can be used as can subepithelial connective tissue grafts with rotated flaps. If the subepithelial graft is used it can be performed prior to uncovery, but the tissue be must be overbulked and then later recontoured. This eliminates the possibility of inadequate bulking at Stage II uncovery but does entail an extra surgical procedure. Therefore, procedures such as autogenous gingival onlay grafting are usually evaluated at the time a tapered transmucosal gingivectomy or a standard non-flap uncovery and healing collars are planned. Whether or not the tapered gingivectomy is to be performed, a sufficient healing period must first be observed if this enhancement surgery is required. For adequate soft tissue healing, a 2-month period should elapse before anything further is done.

Tissue guided regeneration using a reasorbable lamellar strip of allografted bone can also be used to correct lack of attached gingival tissue. However, this sort of surgery can only be done if bony augmentation is required. Assuming it is, then the lamellar strip acts as the barrier to prevent soft tissue invagination and in situations where the tissue has been "plugged up" by adding of extra bone or where there is a need for attached gingiva, the tissue can be resutured over the strip so that primary closure is not achieved. As long as the area is not too long (4–5 mm) and the patient keeps the area meticulously clean, the soft tissue will, over a period of a few weeks, granulate in, creating a new area of attached tissue.

Part 3: Correcting Bony Defects.

Proper anatomical soft tissue contours are dependent on normal underlying osseous topography. Frequently, endosseous implants must be placed into bony sites where there is ridge deformity. This resorption of the residual ridge occurs mainly from a buccal or labial direction resulting in ridge deformities that make it difficult to restore normal anatomical contours and shapes. In fact, the greatest reduction of the residual ridge occurs in the early post extraction healing period from 6 months to 2 years. Studies have further shown that the maxillary alveolar process diminishes by 23% in the first 6 months and an additional 11% in 5 years. In the mandible residual, ridge resorption creates a more lingually located ridge crest.

Tissue guided regeneration procedures such as onlay grafting and osseous refilling are among the approaches most commonly employed to correct these bony defects. As was mentioned above, one of the considerations with these surgical corrective procedures is how they affect both the sequence and timing of prosthetic treatment. Some procedures such as autogenous bone fill or onlay grafting can be performed simultaneously with implant placement but only as long as there is sufficient bone initially to stabilize the implant fixtures. Even sinus lift and bone augmentation procedures (referred to as sub antral augmentations) can be done at the time of implant replacement as long as there is adequate bone below the sinus to stabilize the implants.

A variety of materials can be used to rebuild a lost cortical plate, inadequate bone in the sinus area or a deformed socket. The osteoinductive materials most effectively used are:

(a) Autogenous Transplants—These can be harvested from any number of places, including the shavings from the spade drill, or from the medullary bone of the maxillary tuberosity which is rich in marrow containing precursor cells. If a large onlay graft is required the buccal plate of the 3rd molar crypt or the chin button serve as good sources.

(b) Demineralized Freeze Dried Bone.—This bone is commercially available through bone banks. Some people prefer not to use it because of the potential viral transmission concern and decreased inductive capacity related to sterilization.

(c) Resorbable Hydroxyapatite—This can be synthetic in which case it (HA) lacks osteogenic activity and is more accurately classified as an osteoconductive material. The HA can also be derived from a naturally occurring bovine source. This material has had all of its protein removed and is therefore considered biocompatible.

Many clinicians use a combination of the autogenous bone (because of its osteoinductive potential) and an allograft material such as the resorbable HA for its osteoconductive potential.

The future use of bone fill materials is likely to involve further research into "bovine osteogenic protein" which induces new bone formation in extraction sites in close approximation to the titanium implants within a very short period of time (3–4 weeks). For the present, 6 months should be observed before any progressive bone loading occurs around the implant bone interface.

Part 4: Conclusion.

These procedures for both soft tissue and bony defects, which can for the most part be performed in conjunction with implant installation, function to help reestablish normal anatomical contours. Without these surgical procedures, ridge lapping in removable prosthetic situations or performing tapered gingivectomy procedures according to the present invention for a fixed prothesis would not always be successful because as in standard crown and bridge procedure, the ability to produce full anatomical contour and the correct emergence profiles is critical to a sound aesthetic and functional result. This is something that some implant companies appear to have overlooked.

In those situations when the soft tissue has been augmented to provide for a greater degree of attached mucosa, these procedures help make the peri-implant sulcus more cleansible because firm tissue is much easier to work with than loose flabby tissue.

Bone augmentation procedures are becoming more and more common, especially with the new one-step surgical phase materials such as Bio Col that do not require Guided Tissue Augmentation Membranes (GTAM).

And finally, it should be remembered that clinicians should always start with the end in mind. This means that if osseous augmentation and/or soft tissue enhancement is required, it is preferable to do this in conjunction with the initial implant surgery rather than have to resurgerize the area. This not only creates further delays but requires full mucoperiosteal elevation which in the inventor's opinion should be avoided whenever possible.

Section III: Universal Abutment Systems According To The Present Invention.

Part 1: Introduction

Universal Abutment Systems according to the present invention comprise four basic components as shown in FIGS. 1–11:

(1) A unique transmucosal base 10 preferably having an externally threaded portion 12 and an interlock 14 which fits an implant 16. This base 10 can be adapted to any implant system's 16 mechanical interlock 14A, 14B, making it universally compatible.

(2) A preferably internally threaded core 18 which screws down and bottoms out on the base 10. From this core 18 a castable or millable completely customized abutment 22 is created.

(3) A shorter than conventional fixation screw 20 (with a smaller vertical cantilever).

(4) An anti-rotational mechanism 24 which prevents components base 10 and core 18 from rotating relative to one another when installed.

Figure 6:
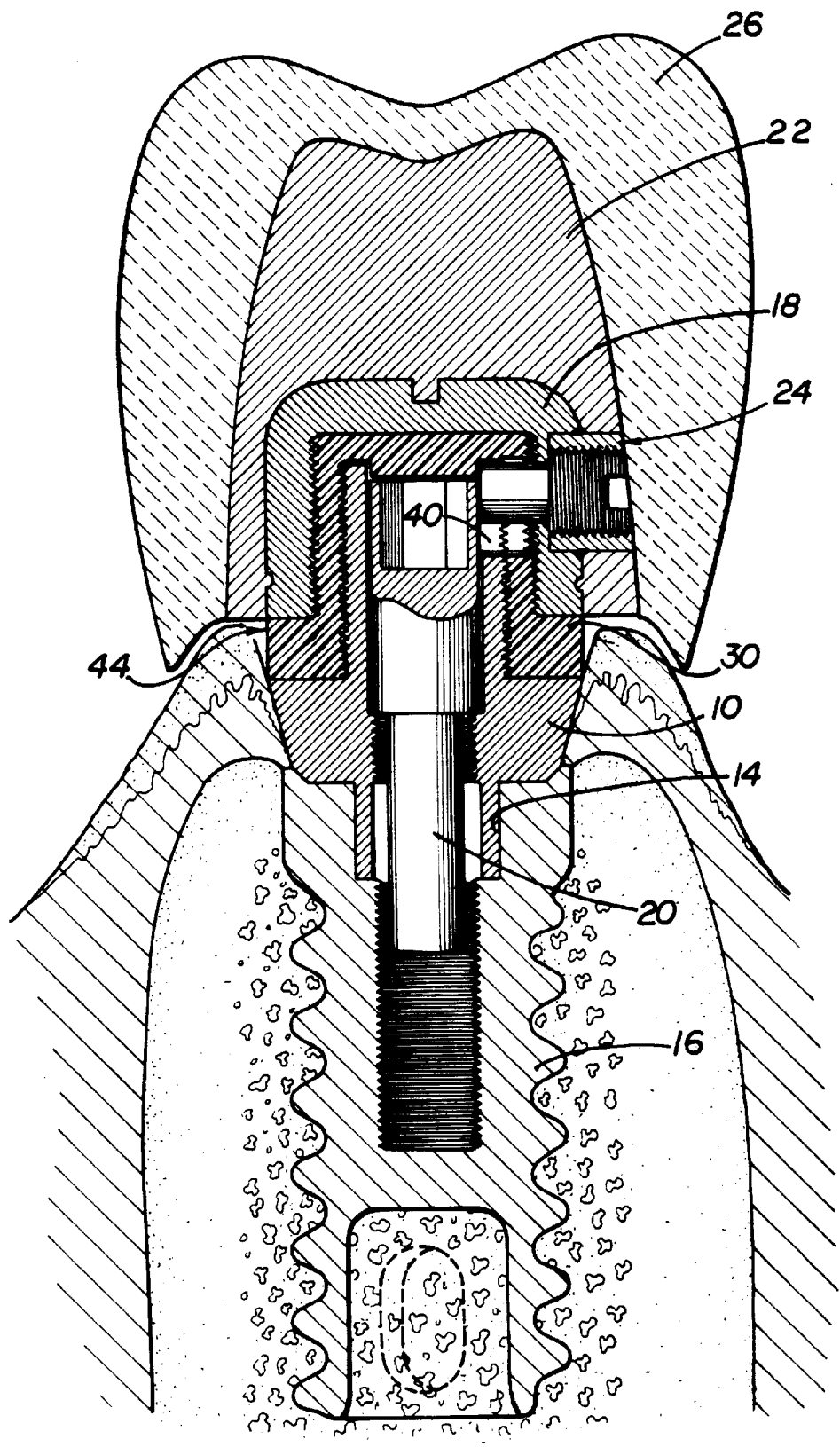
FIG. 6 is a cross sectional view showing a Resilient Core UAS assembly according to the present invention after placement.
Figure 7:
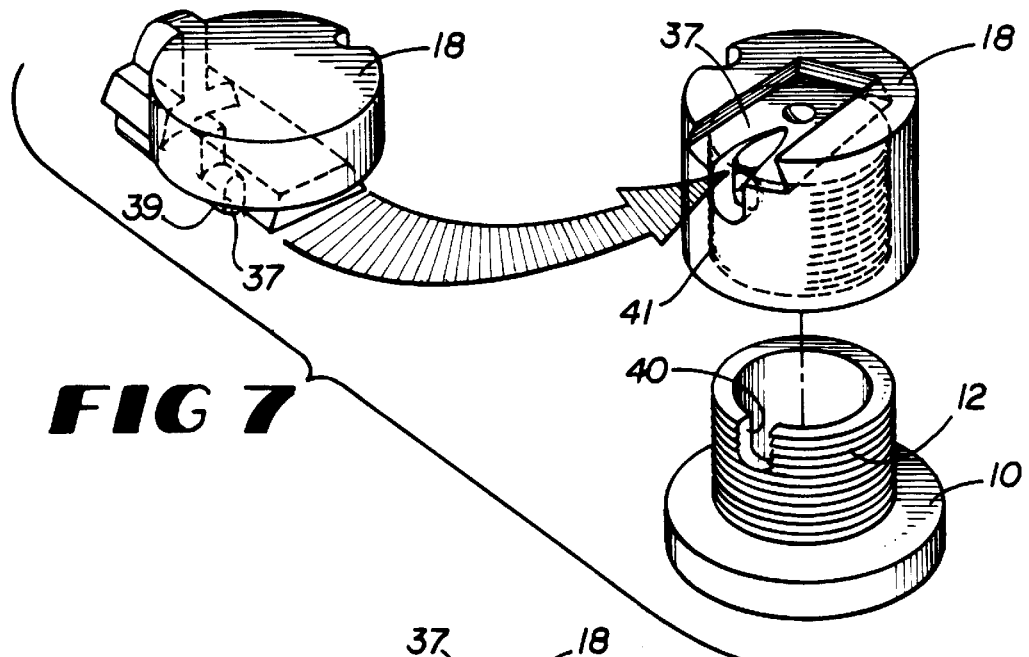
FIG. 7 is an exploded perspective view showing a UAS threaded base and core according to the present invention which employ a sliding lock rather than a locking screw for preventing rotation of the core relative to the base.
Figure 8:
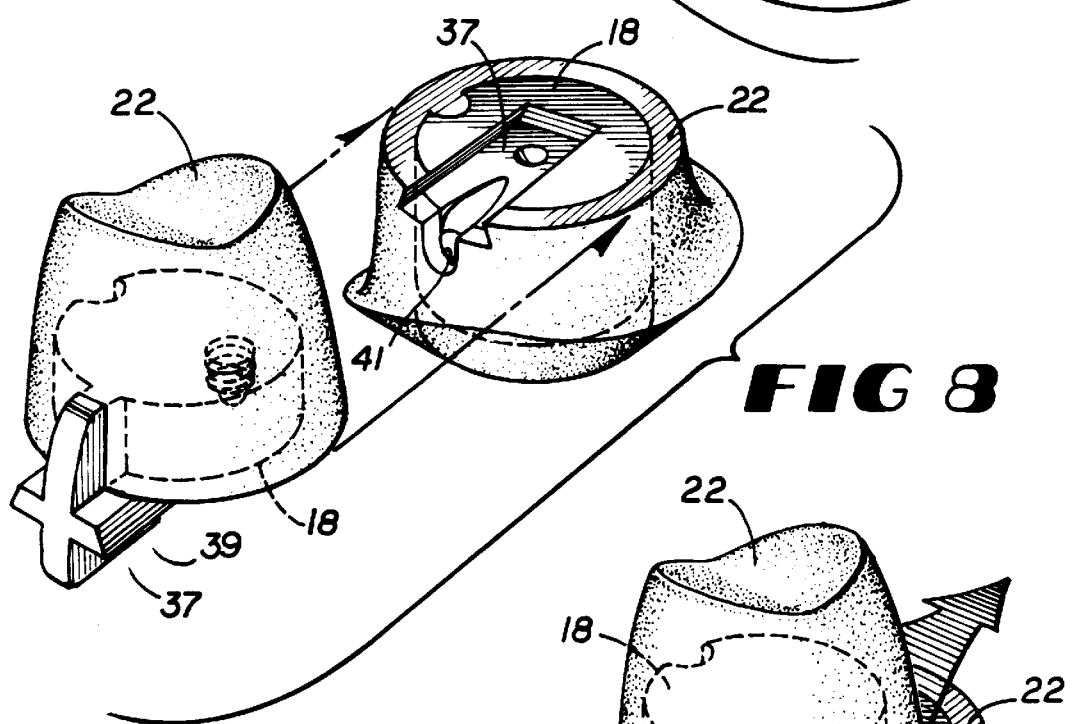
FIG. 8 is an exploded perspective view showing the components of FIG. 7 and with an abutment formed on the core.
Figure 9:
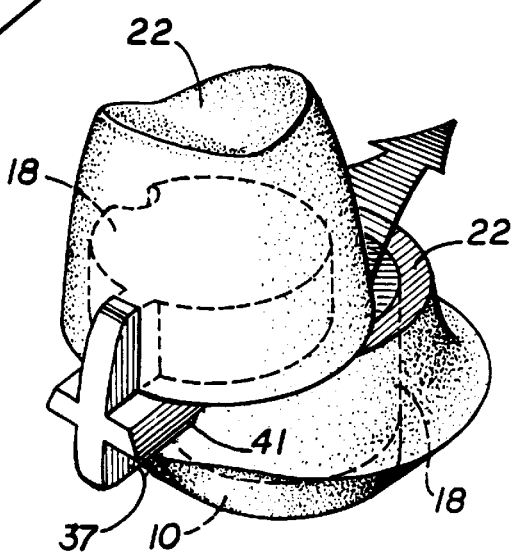
FIG. 9 is perspective view showing the components of FIG. 8 being further assembled.
Figure 12:
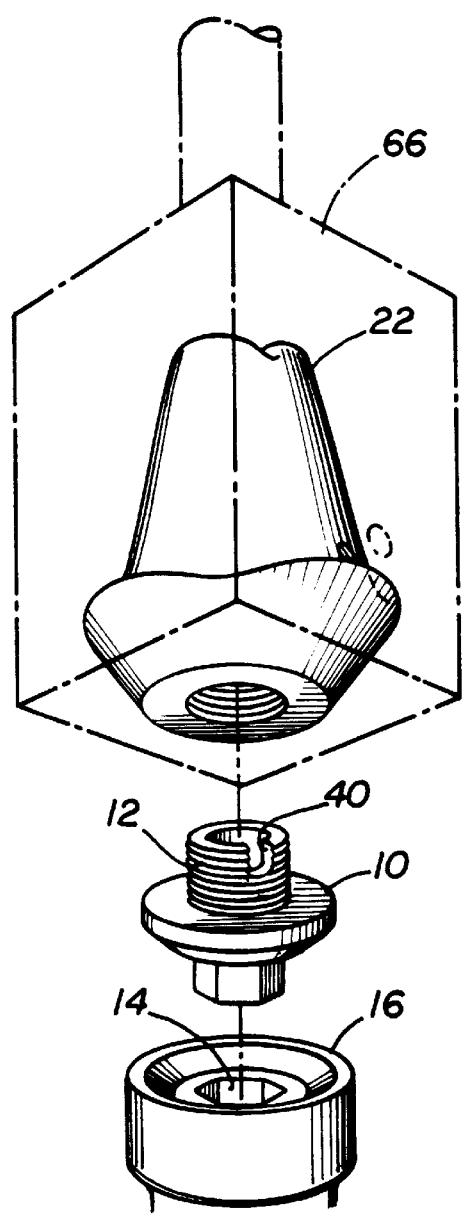
FIG. 12 is a perspective view of components of a Milled Universal Abutment System ("MUAS") according to the present invention.

These systems feature, among other advantages as discussed in the summary of the invention section above, a mechanism for preventing loosening of the fixation screw 20 and a unique method of housing a precision attachment 28 within the normal contours of the abutment 22. Conventional abutment systems do not provide these features, because, among other things, many must contend with central access bores for accommodating the fixation screw. Systems according to the present invention have such universal application that not only can they be made compatible with almost every root form and blade form implant system available conventionally, but also with all overdenture and crown and bridge applications as well. Furthermore, such systems can incorporate resilient core designs as shown in FIG. 6 that include resilient or elastic material 30 in the core/base interface in order to replicate articulation of natural teeth.

Part 2: A Review of Existing Abutment Systems.
Cementable Versus Screw Retained Prostheses:
Which Is better?

The inventor believes that cementing should be used only when (a) the prosthetic system cannot compensate for discrepancies in axial inclinations between the implant and the overlying crown or (b) there is concern over the fixation screws loosening and backing out. Neither seems to be a defensible reason for cementing the abutment or the crown (s), however.

On the other hand, there are many advantages to the use of screw retrievable abutments. Even with the use of pre-angled abutments or UCLA type abutments discrepancies between implant and crown axes can exist. Dr. Chiche refers to these problems as "eccentric screw positions," which are simply nothing more than poorly located screws. Because the screw-retained abutments are such a popular addition to the armamentarium of almost every prosthetic dental implant company, the solution to the problems of eccentric screw positions, screw fracture and screw loosening has far reaching implications.

No matter what type of implant has been placed, up until present there have only been a handful of options for the clinicians who wish to place a screw-retained abutment and a crown or bridge to correct for eccentric screw positions. First, one can make the abutment system screw retrievable, but cement the overlying crown with a permanent luting agent. The inventor believes that this is an unacceptable compromise in treatment. There are others that recommend the use of provisional cement but this also has its problems.

Second, using a noble alloy, one can cast a wax pattern to an existing straight hex/octa lock abutment or pre-angled abutment, redirecting its path of draw for proper screw emergence using a set screw. Unfortunately, this creates extra bulk and the original prefabricated component almost always has to be ground down or altered. This often compromises the fixation screw and is a time consuming process. Furthermore, this method does not address the issue of screw breakage and cannot be used to incorporate intraabutment precision attachments, which will be discussed later. Perhaps even more important is the fact that one cannot successfully cast or solder to titanium or titanium alloy with any reliable degree of success. A seemingly acceptable mechanical bond may be created, but never a metallurgical bond, which is the only truly stable type of bond between different metals. Furthermore, casting to titanium or titanium alloy, with a noble metal, must be done in the 1400°–1600° F. temperature range. Given the melting point of titanium, and depending on the grade, the risk is obviously that of altering the titanium's physical properties, which can obviously lead to metal fatigue and failure.

Third, one can fabricate an auxiliary substructure (telescopic coping) to correct the axial alignment. C. E. Rieder, *Copings on Tooth and Implant Abutments for Superstructure Prostheses,* 10 Int'l J. of Periodontics and Restorative Dentistry 437–51 (No. 6, 1990).

Fourth, one can use a plastic waxable sheath or a direct gold coping. However, it has been correctly emphasized that for severe angulation problems telescopic copings are also required.

The first and second options are self-explanatory. The third option means placing a telescopic coping and redirecting the path of emergence of the fixation screw with a secondary set screw. This set screw can be used to anchor the overlying crown to the coping and the position of the screws can be selected so that they do not interfere with proper occlusal morphology or aesthetics. For the third option, this also means extra steps, time, money, materials and, therefore, extra bulk.

For the fourth option, the Impac line of Vidents plastic waxable sheaths is a good example since it is said to be compatible with almost every major implant system. However, the Impac line seems to create its own special sorts of intricacies and, in the inventor's opinion, so can the direct coping and sheath combinations offered by Interpose ISS, Calcitek, Nobelpharma, 3I, Steri-Oss, Dentsply, Attachments International and other suppliers of conventional systems.

Use of an I.T.I. Bonefit Implant also allows for angulation compensation, but what is unique about the I.T.I. System is that this compensation of eccentric screw position is made in the root part design of the implant. It achieves this with a 15° angled implant neck. (A description of the I.T.I. System can be found in the JPD January 1992 issue.) As the authors of this article point out: "If angulation problems are extreme . . . telescopic constructions or primary gold coping can be made." G. M. Ten-Bruggenkate, F. Sutter, H. S. Oosterbeek and A. Schroeder, Indications for Analed Implants, 67 J. Prosthetic Dentistry 85–93 (No. 1, 1992). Therefore, if implant angulations are severe one is no further ahead with this implant system than any other because the auxiliary substructure is still required, and the problems of access bore location and screw loosening yet remain to be solved.

Contrast and comparison of the majority of conventional screw-retained implant systems to universal abutment systems of the present invention can begin simply by eliminating those systems where the sheaths are held to a metal transmucosal base by a fixation screw, but with no hex or octagon mechanical interlock. These systems do not adequately account for rotational stability. The abutment sleeve can in fact rotate as it is being tightened down to say nothing of the potential hazard of screw loosening.

Other suppliers of conventional systems provide a more stable direct connection between the implant and the plastic sheath in the form of a machined interlock made of either plastic or metal. These systems, however, like the ones offered by ISS, 3I, Vident and Nobelpharma, cannot prevent screw loosening. In fact, none of these systems appear able effectively to prevent the fixation screws from loosening and backing out. In the February 1993 issue of JPD, an article by Jaggers, Simons and Badr reported that "the main disadvantage of the UCLA Abutment is the potential for loosening of the retaining screw. This is related to frictional wear and micromovement between the titanium screws and the internal threads of the implant body. Frequent recall visits may be needed to tighten the screw." A. Jaggers, A. M. Simons and S. E. Badr, *Abutment Selection for Anterior Single Tooth Replacement: A Clinical Report,* 69 J. Prosthetic Dentistry 133–35 (No. 2, Feb. 1993).

The UCLA system is the same system that Implant Support Systems states "has been called the most significant product to improve aesthetics since the introduction of the Branemark System". Implant Support Systems Product Catalog (1993.). In truth, screw loosening is perhaps one of the single biggest problems plaguing the implant industry as a whole. In the 1993 Implant Support Systems Catalogue, ISS described "the problem of chronically loose fastening screws," which ISS blames on the "micromovement of the implant components and the supported prosthesis which can cause improperly tightened fastening screws to back out. Besides the aggravation, patient inconvenience, and loss of chair time, loose parts can also result in failure or component fractures." Id.

The problem of screws loosening and backing out is truly a universal problem. Companies try to solve this problem by endorsing the use of a torque wrench. Unfortunately, this does not solve the problem of the inadequately designed direct connection abutment. At a meeting of the International Congress of Oral Implantologists (March 1993), it was postulated that screw loosening occurs when complete seating of the abutment in the implant is not achieved, and that it has a great deal to do with less than adequate tolerances between these parts. It is this inventor's belief, however, that no matter how exacting the tolerances of these parts are, a retaining screw cannot be expected securely to hold the abutment directly to the implant, for when the screw shoulders on the sleeve and attaches directly to the implant, the forces of occlusion are directed around the neck of the screw. In a two piece system like the ones offered by Impact, Steri OSS, 3I and Nobelpharma this is simply too much strain and leads to loosening and/or breakage.

Calcitek, like ISS and others, also endorses the use of thread sealant to help prevent the eventual unscrewing of abutment, attachments and screws. Unfortunately, like the torque wrench, the occlusal loading forces far exceed the adhesion of the sealant. This sealant is, however, excellent for preventing a bacterial buildup and the subsequent odor that can develop around the implant abutments. Another of the big concerns over loose parts is that they are no longer passive fitting and therefore can frequently break under occlusal load or cause damage to the implant-bone interface.

Apart from screw loosening and screw fracture, the retaining screws of some systems (particularly the IMZ, the UCLA and the direct gold coping system of Calcitek) which anchor the sheath to the implant, protrude above the implant and can sometimes interfere with the axial wall preparation of the custom angled wax pattern.

The direct gold coping system of Calcitek is sufficiently large that it also frequently interferes with the placement of set screws and attachments. If one were to incorporate a solid core onto which a wax pattern could be cast (UAS) or an abutment milled (MUAS), and there were no plastic sheath or bulky gold coping underneath (with an access bore problem), it would be a much simpler and easier task to create a customized abutment.

Another problem with the UCLA Abutment is that (and again from the ISS Catalogue) "there has been a high incidence of failure of the two piece designs when investment finds its way into the junction between the metal and plastic cylinder. This causes a hairline defect in the final casting that subsequently fractures under load." ISS's solution to this problem is to use a machined, one piece UCLA abutment and a screw, onto which a gold alloy is cast. The problem with this solution is that it is bulky and can make restoring teeth with a lack of interocclusal distance very difficult—not to mention extra steps and extra components, which once again raises the issue of time and money. Furthermore, a substantial opening must be created to allow for the fixation screw's retrieval. This weakens the abutment and creates a huge access channel in the crown. This large access bore hole also creates limitations as to where additional set screws and attachments can be placed, for obviously they cannot be placed so that they block the access hole. The proponents of the UCLA abutment deal with the large access opening by sealing it with gutta percha and resin which, in the inventor's opinion, is hardly a permanent solution. It must be understood that the problem of the central fixation screws and access bore are common to virtually all if not all retrievable abutment systems, not just the UCLA system.

Sometimes a coping is used over the castable sheath to carry the tube of the screw, redirect the screw emergence, and reduce the size of the access opening. In the Journal of Prosthetic Dentistry April 1992 issue, Dr. Lewis and others point out that "slight angulation problems may be solved with the UCLA abutment" but that "bucally inclined implants would normally result in screw access openings on the facial surface of the restoration requiring extensive steps of fabricating custom telescopic copings." Lewis, Llamas and Avera, *The UCLA Abutment: A Four Year Review,* 67 J. Prosthetic Dentistry 509–15 (No. 4, April 1992). Unfortunately, there is often not enough interocclusal space to do this.

To solve this problem many technicians attempt to use the metal framework of the crown to redirect the path of the set screw, but it is not thick enough to accommodate a 3 or 4 mm screw. Thus, a threaded hole must also be tapped into the wall of the abutment. Unfortunately, not many people can cast in an appropriately hard enough metal (e.g., non-precious metal) or place a fine enough thread to prevent thread stripping or screw loosening without creating galvanic reactions or biocompatibility problems. Companies such as Calcitek try to solve the problem of screw loosening as mentioned earlier by recommending use of a thread sealant. As it stands, altering the coping or the abutment sheath to accommodate screw fixture is not only unreliable, but is also time consuming and involves many extra steps.

With the direct connection that the UCLA abutment and other plastic waxable or machined sheaths offer, there is the added problem of verifying the fit of the casting at the level of the osseous crest. Lewis et al propose that all direct abutment restorations on multiple implants must therefore be made as individual units and then soldered to one another, and that indexes are required to verify the fit of these castings. Id. All this is done to ensure a passive fitting framework which in fact does not remain passive once the retaining screws are tightened or come loose.

Universal abutment systems according to the present invention, however, eliminate these steps because the accuracy of the framework can be explored visually due to the design of the threaded base. Another reason these steps are not necessary is due to the fact that resin bonding technology involving precision attachments according to the present invention solves the problem of passive fit.

Lewis et al also point out that UCLA castings with round bases can be used for multiple implant restorations. This round base has no hex connection because, as Lewis states, "to engage the hexes on a multiple implant could make seating the restoration extremely difficult." Id. Lewis states that "the connection to multiple implants will prevent any possible rotation," but in fact, if a precision attachment appliance is used the abutments must be individually anti-rotational to prevent the attachments from lining up incorrectly. In order to bypass this problem of multiple hex-hex or hex-octagon positions and yet maintain rotational stability, the universal abutment systems according to the present invention employ a unique hex, octa or other desired shape lug/recess and thread combination that is disclosed in further detail below.

Because no conventional abutment systems have this unique hex-thread combination, they thus make it more difficult to incorporate precision attachments and align them accurately. Even if all of the abutments and attachments can be aligned accurately, the location of the central access bores prevents the attachments from being placed near the long axis of the implants. Thus use of these types of abutments for this sort of removable appliance is simply not a realistic option.

Apart from the direct abutments such as the UCLA system or the direct gold coping, almost all suppliers produce a screw-retrievable prefabricated straight or angled abutment. These are very popular components, but there are many situations in implant dentistry where these systems do not permit the precise clinical requirements of the specific case. This may be due to improper angulation of the implant fixture and associated aesthetic problems, or it may be due to reduced interocclusal space or lack of a finished shoulder ledge. Similarly, the fixation screw may pose a risk of breaking or loosening. In other words, such conventional prefabricated straight or angled abutments are also limited in this application.

One of the major concerns with several of these systems such as Calcitek and Dentsply is that there is no shoulder preparation allowance on the abutment sleeve, which makes it difficult to create a finely finished margin. The conventional pre-angled abutment or PAA's come in a variety of angles, depending on the supplier. From a manufacturing point of view, however, producing multiple variations of PAA's is expensive and really not necessary since there are many instances when a customized angle and height are required. For example, 3I produces a PAA with a secondary set screw already machined into the abutment but it has a pre-set vertical and is useless if the abutment must be ground down as it frequently is.

The multiple rotational position may allow for some part of the abutment to be parallel, but in most instances the abutment still needs alteration and this is often done very inaccurately with a resultant reduction in retention. A perfect example would be when the clinician tries to parallel six implant abutments for a full arch fixed crown and bridge case and several of the implant fixtures are poorly angled. Unless the clinician is prepared to go to the extra trouble of making telescoping copings, the pre-angled abutments must be dramatically altered—to such an extent that the abutments lose their retentiveness and the crowns frequently end up being cemented, or an overdenture is placed.

Plastic waxable sheaths and direct gold copings are not the answer either, because of the problems posed by the access hole of the retaining screw and its potential for loosening. As discussed below, the use of a coping may solve the problem of "draw," but it is frequently an imperfect solution for it involves many extra steps, more money and besides, the old abutments under the coping still utilize an elongated fixation screw which can be subject to undue stress.

The prosthetic system offered by Calcitek, the Integral Omniloc System, is a perfect example of why telescopic copings are required in conventional systems. Even with its pre-angled 15° and 25° abutments, auxiliary substructures are endorsed when there are discrepancies between implant inclination and the facial crown contour. Calcitek, in fact, subscribes to the idea that simplicity is a key requirement for its abutment system, "to minimize the number of components used." The inventor believes that Calcitek's endorsement of telescopic coping is contrary to the basic premise of simplicity. Calcitek is not alone however, for none of the other conventional implant systems provide a better solution. The use of an auxiliary substructure to parallel abutments also creates aesthetic compromises, for as the margin of the telescopic coping is brought more occlusally to parallel the coping, a metal collar which cannot be masked appears. This problem does not occur with the UAS.

Many angled abutment systems suppliers claim that their products can be altered by grinding down the metal and then rewaxing the custom shape necessary, but this is both a time consuming procedure and one which does not readily correct for eccentric screw position. Straight hex and octa lock abutments of Steri OSS, Nobelpharma, Calcitek, Dentsply, 3I and others are examples. Furthermore, achieving a metallurgical bond between the titanium alloy and other metal is questionable due to the incorporation of an oxidation layer. As a result a purely mechanical bond is created which in the inventor's opinion is not adequate. The added bulk of the cast to abutment also inevitably interferes with the placement of set screws and precludes the use of intraabutment attachments.

In the case of Dentsply's Titanium Abutment (TLT), which is a one piece screw system, the abutment can theoretically be altered simply by grinding down the metal, then casting it. The problem with this system is threefold. First, because it is a one piece unit, it is screwed into place bypassing the hex or octagon interlock between the abutment and the implant making it virtually impossible to accurately duplicate its original orientation in the mouth. Second, a crown cannot be screw retained to the TLT if an eccentric screw position exists without either altering and "casting to" the TLT which can be a suspect solution, or fabricating a telescopic coping. If these options are not employed the crown is usually cemented. Third, the TLT cannot prevent screw loosening.

It is also important to remember that altering the path of draw of, say a conventional hex lock abutment, plus additional lateral stresses on its elongated fixation screw, can lead to screw breakage. Rather than complicating matters by waxing to an existing prefabricated abutment, the entire abutment system can be simplified by using a UAS. Similar problems exist for the direct gold copings; however, they have the additional problems. that stem from access bore and screw loosening. Because this system, like the plastic waxable sheaths, has a direct connection to the implant, it is prone to screw loosening, unlike the UAS.

Many clinicians endorse the use of Plastic Castable Abutments (PCA). They too, however, have a limited application and are mostly used when the clinician decides to cement a single crown. Unfortunately, there are a number of problems with doing this. First, the prefabricated transmucosal collars are a standardized width and shape which makes it cumbersome adjusting the plastic and wax portions to accommodate the often thin friable anterior maxillary tissue. Cementable fixtures such as the PCA are very technique sensitive, and as Chiche has stated "Unpredictability of the agents used in luting may result in either difficult retrieval or premature loosening," [McGlumphy and Papazoglou, *The Combination Implant Crown: A Cement- and Screw-Retained Restoration,* 13 Compendium Continuing Educ. Dent. 34–42 (No. 1)] not to mention incomplete seating. If the PCA, for example, is not fully seated the implant abutment assembly is not stable. Clinically, if this happens it can lead to a non-passive fit and or cause periodontal problems. The PCA also requires pre-angling and alteration which usually must be done in the mouth—this is time consuming, cumbersome and less accurate than with other systems such as the universal abutment systems according to the present invention. Implant Support Systems (ISS) also offers a castable plastic cement on crown (COC) which is an abutment designed to be threaded rather than cemented into the implant. However, there is a world of difference between a cast thread and a machined thread. With a cast thread, for instance, there is always the risk of damaging the implant thread.

For those clinicians who are placing implant assembly systems, the second worst feeling next to a loosening implant is that of a loosening abutment—one that has loosened because the fixation screw holding it in place has broken or come loose. As described above, the use of fixation screws in screw retained prostheses has also caused concern due to problems with aesthetics, path of emergence and alteration of abutments.

It is also painfully obvious that the control access bore of most retrievable systems prevents precision attachment housings from being placed within the contour of the abutment and thus axially loading the implant. The added bulk created by casting or soldering the attachment into place not only grossly overcontours the abutment but also affects the attachment's physical properties. Ideally the attachment should be resin bonded within the contour of an abutment that has no central access bore. This is impossible to do with conventional existing abutment designs but not with universal abutment systems according to the present invention.

More often than not, when screws break, they break off at the thread which leaves them submerged in the implant. This makes them very difficult to remove without damaging the implant. The inventor has seen many interesting techniques for retrieving broken screws, but all it takes is to damage a single thread of just one implant and potentially an entire case can be put in jeopardy.

It can be argued that the only reason these screws break is because of poor treatment, planning and excessive occlusal overloading of the implant assembly. However the inventor has seen numerous cases of screw breakage—everything from the screw-retained single tooth, to a screw retained dolder bar supported by six implants. Even though there are times when screw fractures can be caused by occlusal discrepancies and "sloppy tolerances" these are not the primary reason for breakage. Rather, fixation screws fracture as a direct consequence of inadequate abutment design, specifically the manner in which the abutments are connected to the fixation screws and the tremendous strain that is exerted on them.

The fulcrum or point of "0 Force" for a fixation screw is usually at the level of the implant screw threads and that portion of the fixation screw extending occlusally into the abutment sleeve acts as a vertical cantilever. The longer the screws, the greater the risk that occlusal forces will lead to screw breakage. In fact, the bending moment which the screw undergoes leading up to breakage is a function of: length of lever arm (cantilever) x force (occlusal load). Therefore, in an ideal world, the shorter the fixation screw, the less bending moment and less chance of breakage. In other words it is advantageous to have a shorter screw bearing the bending moment.

Universal abutment systems of the present invention address all of the above mentioned problems without the need for an auxiliary substructure, and can also prevent loosening of the fixation screw.

A relevant conventional system for comparison is the Ha-Ti system which is disclosed, among other places, in the Mathys Product Catalog [Articles in the Mathys Product Catalog and Scientific Research Papers, including Dr. G. Graber, ZWR, 100. Jahr g. 1992, Nr. 2 70–76; Dr. Ledermann, *Neue Chirurgische, Konstruktive und Zahntechnische Aspekte in der Enlossalen Implantologie,* Quintessenz Heft Jan. 1, 1992 43, 7–22 (1992)]. According to this system abutment design, the abutment requires no central access bore. However, that abutment or "soldering base" appears to have a very limited application. First, it is positioned so its inferior border is level with the gingival crest and so it is not employed to develop a transmucosal gingival taper like the UAS or MUAS of the present invention. Second, it has no means of preventing itself from unscrewing from the soldering base ring—in other words it has no anti-rotational mechanism and therefore cannot be used to reproduce an exact rotational position like the UAS or NUAS of the present invention. Third, no mention is made of how slide attachments could be housed in the soldering base. There is also no mention of how the component can be customized and reangled in situations where the implants are eccentrically positioned. Another limitation is that the semi precision attachments are soldered to the "soldering base" and not anchored into cavities by resin or a casting technique as in the UAS. Fourth, the Ha-Ti system does not incorporate any form of intra abutment resin bonding like the present invention in order to resolve the problem of passive fitting prostheses. In the internal portion of the soldering base there is no lug or projection and thus there is no way to prevent the fixation screw from loosening. In fact, because the threads of the soldering base and soldering base ring are not opposite to one another, the Ha-Ti design may not be stable for any purposes. Fifth, the Ha-Ti soldering base ring also demonstrates no ability to help establish preferred non-circular customized diverging flare of the transmucosal taper. And because this system has no capacity to create this sort of taper, it does not benefit from the modified impression copings and custom healing collars of the present invention. Sixth, the Ha-Ti soldering base, unlike the UAS System, cannot be modified to create a CAD/CAM generated completely customized abutment complete with anti-rotational mechanism. Seventh, unlike the UAS, whose threaded base can be made compatible with internal and external mechanical interlocks of the various implant systems, the Ha-Ti system cannot, because it is specific for the Ha-Ti implant and its hex interlock has a greater diameter than its threaded portion. Accordingly, placing a recessed hex on the soldering base would eliminate the threads. This in other words would radically alter the design concept of the Ha-Ti system. The Ha-Ti soldering ring also engages a ring at the same time it engages the hex of the implant and is therefore specific to the Ha-Ti Implant. Eighth, the Ha-Ti soldering ring is used as a solid soldering base whereas the UAS core 18 can be modified with slots, grooves and channels that open internally to expose the notch on the base 10 and form a customized sliding lock 37. Ninth, the Ha-Ti system cannot incorporate a resilient core component 44 whereas the UAS and NUAS of the present invention can. Other differences will be apparent.

Part 3: Universal Abutment Systems.

Many features of conventional screw-retained abutment systems reflect good design practice, especially the protruding or recessed hexagonal or octagonal mechanical interlocks of certain specific abutments which are adapted to engage certain specific implants, and the use of a fixation screw. However, concern arises over the design of the coronal portion of the abutment and the way it is anchored to the transmucosal base or directly to the implant. It is these aspects of the prosthetic system and the central access bore which need to be dramatically altered, and this is what the UAS and MUAS of the present invention accomplish.

Some systems use a two piece abutment system that anchors directly to the implant fixture by a long fixation screw but as has been seen these systems experience problems with screw loosening, eccentric screw position and screw breakage. The three piece assemblies which consist of a transmucosal portion, an angled post and a fixation screw exhibit some advantages (in the inventor's opinion) over the UCLA type abutments; however they too still share conventional problems.

The universal abutment systems according to the present invention, as shown perhaps most clearly in FIGS. 2–5, feature a base 10 with a mechanical interlock 14 that is compatible with any implant system. This creates a totally universal component and interface to the abutment system of the present invention. The coronal threaded portion of the base 10 has a left handed thread, which engages in a counter clockwise direction (opposite to the fixation screw which penetrates the center of the threaded base) and it preferably employs a worm screw thread design. The threaded portion of the base 10 receives the internal threads of the abutment core 18, which is preferably a thimble shaped component that screws down very precisely onto the base 10 and in fact bottoms out on the base. The threaded portion of the base 10 and the core 18 can be manufactured in varying heights to accommodate the variable height of the transmucosal tissue and often severe inclinations of some implants.

Through the center of the base 10 a fixation screw 20 is used as it was intended—to anchor the base 10 to the implant fixture 16 via their mechanical interlocks 14. A standard fixation screw would emerge through the top of the base's threaded collar. It would need to be cut off in order to remain slightly submerged below the top of the base 10. Therefore a fixation screw 20 which has been so modified according to the present invention is used. It is shorter and has less of a cantilever arm and for this reason is subject to less of a bending moment. As shown in FIGS. 2–5, the top of the fixation screw 20 features a (preferably) hex hole to provide for easy retrieval. Once the fixation screw 20 has securely fastened the base 10 to the implant 16, a core 18 according to the present invention can be screwed down onto the base 10.

The flat portion of the base 10 onto which the UAS core 18 bottoms out is preferably approximately 0.6 mm in height. This creates a very short transmucosal portion which is often advantageous when restoring areas where the tissue is thin and friable for it allows the crown margin of the customized abutment 22 to be placed on the UAS core 18 within 0.75 mm of the implant. (The UCLA abutment allows only 1 mm). Using a UAS core, the taper for the crown 26 can be started further subgingivally. This is also advantageous when the clinician needs a more divergent restoration to help create the appearance of interproximal papillae.

The UAS core 18 is designed to "cap off" the fixation screw 20 and therefore provides no external access bore. In order to access the fixation screw 20 the UAS core 18 must first be unscrewed. Because it is the UAS core 18 to which wax is added and then cast to create a customized abutment 22, this system is able to provide a retrievable customized abutment 22 with no central access bore.

The UAS core 18 may be machined out of a non-oxidizing metal such as ceramicor or platinum iridium and preferably has a retentive sandblasted exterior surface which extends to the edge of the base 10. The core 18 may also be designed with an annular ring for increased retention (a bell- or other desired-shaped top can also be incorporated into its design for this purpose as well). The head of the core 18 also features a slot in it to allow it to be screwed down onto the base 10.

On the internal aspect of the core 18 there is preferably a machined projection 32. When the core 18 has bottomed out, which preferably happens at precisely 1 rotational position, the projection 32 is aligned with the head of the fixation screw 20. Furthermore, the projection 32 is machined to such exacting tolerance that it almost bottoms out against the top of the fixation screw 20 head at the exact moment that the core 18 bottoms out on the base 10. There is, however, an intentional micro gap which forms between the head of the screw 20 and the projection 32, but if the fixation screw 20 unscrews more than 15° or ¹⁄₂₄th of 1 turn it will bottom out against the projection 32. If this happens the frictional rotation of the screw 20 against the projection 32 acts to tighten the core 18 thereby preventing it from ever loosening. In other words the unique combination of the counter rotational core threads and its internal projection 32 prevent the fixation screw 20 from unscrewing far enough to create a "loose abutment".

An anti-loosening screw (sometimes hereinafter, "screw") or similar anti-rotational means 24 is also preferably incorporated into the UAS design to further guarantee that the core 18 will not become loose. If the core 18 does not come loose then the fixation screw 20 cannot come loose, as described above. The ALS mechanism comes in at least two basic designs. Both have the same function, although they both have different applications.

The first design, which is shown in FIGS. 2 and 3, is the "standard ALS mechanism" 34 which has an internally threaded sheath 36 through which passes a screw 38 with a non-threaded dog point that inserts into both the wall of the core 18 and the base 10. This standard design bottoms out in the wall of the core 18, rather than against the fixation screw 20, in order to avoid imposing lateral loads on fixation screw 20. When the screw 38 is fully engaged (shouldered in the wall of the UAS core 18) its dog point is flush with the internal wall of the base 10 and thus does not interfere with the fixation screw 20. In fact the dog point engages a machined notch 40 in the wall of the base 10.

The second design is a "modified ALS mechanism" 35, one version of which is shown in FIGS. 4 and 5 and has a non-threaded internally tapered sheath 43 through which passes a modified screw 45 that inserts into both the wall of the core 18 and notch 40 of the base 10. The screw 45 of this modified ALS mechanism 35, unlike the standard ALS mechanism 34, has a threaded dog point and a non-threaded shank. This modified design bottoms out on the internal taper of the sheath 43, once again to avoid imposing lateral loads on fixation screw 20. This design is very helpful in situations of extreme angulation where the screw 38 and sheath 43 have to be cut right back because the screw threads are internal to the core 18.

Both of these anti-rotational mechanisms 24 (34 and 35) act to "lock" the core 18 and base 10 together not only maintaining an exact rotational position but also preventing them from unscrewing. This is achieved in the following manner; when the core 18 is fully seated, the screw 38 or 45 passes through the core 18 and then engages a notch 40 in the top of the base 10. When the screw 38 or 45 engages this notch 40 it creates a "dead bolt effect".

With both designs the bore holes (both larger diameter in the core and small diameter in the core and the base) may be formed when the core 18 is assembled to the base 10. This way is simply more accurate than attempting to try and line up the bore holes for the screw 38 or 45 in two separately machined components.

The UAS core 18's rotational position can therefore be accurately repeated because of the combination of the ALS and the precision milled core 18 and base 10. This precise rotational position is critical and can be achieved in different manners by other systems but not in combination with an anti-screw loosening capability or without a central access bore as in the UAS. These are features that preclude the use of intra abutment precision attachment prosthetics in other, conventional systems.

The anti-rotational mechanism 24 may also take the form of a sliding lock mechanism 37 as shown in FIGS. 7–11, in which the core 18 comprises two sections that fit together in a dovetail or other cooperating fashion in such a manner as to insert a protrusion 39 on one section into a corresponding slot 41 in the other section of the core 18 and the base 10. This may be accomplished with the abutment 22 formed on the core 18 in conventional manner.

Before the unique features of these ALS mechanisms 34 and 35 are discussed in further detail, it should be mentioned that the custom wax pattern is added onto the UAS core 18. This is done by waxing around the sheath 36 or 43 and the screw 38 or 45. The wax pattern(s) can be shaped and angled as required. This may involve parallelling six misaligned implants or a poorly angled single abutment. It may require incorporating a step preparation into the wax abutment (not shown) or setting a tube and screws or creating a box preparation to accommodate a precision attachment component 78 or 80 (see FIGS. 28 and 29). All of these options are available. Before the wax pattern is finalized the margin must be created to reflect the scalloped contours of the lab model, which assures that the margins are positioned subgingivally. This margin for the crown 26, that will be formed later, must extend below the ALS 38 for reasons that will become more evident below. At this time the precision attachment component 78 or 80 (be it, for instance, an intra-abutment slide attachment) can also be secured into the wax at the appropriate angulation and in the appropriate position. The precision attachment 28 can also be added to the abutment 22 after casting, if a wax cavity is created for it. As will also be explained below, the attachments 28 can subsequently be resin bonded to place.

The wax pattern(s) are now ready to be cast to the UAS core 18—the importance of the ALS sheath 36 or 43 now becomes readily apparent, since it is used to protect the ALS screw 38 or 45 threads during the casting process when the wax abutment (not shown) and the UAS core 18 are cast to become a solid one piece custom cast abutment 22.

The ALS sheath is left extending out from the side of the core 18 until after the abutment 22 is cast; only then can the screw 38 or 45 and the sheath 36 or 43 be cut down so that they are flush to the axial wall of the abutment 22. Once the exact screw length is determined a slot can be created on the head of the screw or a pre-slotted screw 38 or 45 can be used.

After the abutment 22 has been cast (preferably investment cast using conventional techniques based on the wax-up abutment 21), the metal framework for the crown 26 can be fabricated and once this framework has been firmly anchored down on the abutment with a screw block or intra abutment precision slide attachment the ALS mechanisms 34 or 35 cannot loosen simply because it cannot back out. Frameworks can easily be created with as little as 75–100 microns micro gap fit so with the screw 38 or 45 being flush with the abutment 22, it too is within 75 to 100 microns of the crown's framework. Because the dog point of the screw 38 or 45 engages 0.4 mm (nearly 400 microns) into notch 40, it is therefore physically impossible for the screw 38 or 45 to back out far enough to disengage the notch 40.

If the anti-rotational mechanism 24 cannot come loose not only can the exact rotational position of the abutment 22 be maintained but also the abutment 22 cannot come loose and therefore neither can the fixation screw 20. This simply means that the entire abutment system remains firmly in place.

The UAS allows the anti-rotational mechanism 24, with considerable flexibility, to be located labially on anterior teeth and mesiolabially or lingually on the posterior teeth. This is done by rotating the threaded base 10 so that the notch 40 is properly positioned and provides proper access for the dentist when tightening and loosening the screw 38 or 45.

Both anti-rotational mechanisms 24 are also designed so that they can be inserted into the UAS or NUAS assembles before they are fully seated. This prevents mishandling of the mechanism 24 in hard to reach areas of the mouth. As mentioned earlier, anti-rotational mechanism 24 also aids the UAS and MUAS assemblies in reproducing an exact rotational position, because they will only engage the notch of the base 10 in one precise rotational position. This one position is where the outer and inner bore holes in the core 18 and base 10 align. Therefore, one can verify that the core 18 is completely seated when the screw 38 or 45 can be screwed all the way in flush to the axial wall of the abutment 22. This unique anti-rotational mechanism 24 never comes in contact with the fixation screw 20, unlike in other systems. This provides an independent and reliable means of confirming the proper fit of the components of the present invention to the implant 16 (unlike the UCLA system, for instance, which must be examined "microscopically" for such confirmation.

The UAS base 10 and core 18 assembly also allows for the total retrievability of a crown and bridge prosthesis without the need of a telescopic coping or auxiliary substructure or the worry of eccentric screw position. Just as importantly, its design strengthens the abutment 22 and totally prevents any chance of the fixation screw 20 loosening or backing out. Because the fixation screw 20 cannot loosen and is not in direct contact with the abutment 22, it cannot extricate itself either, unlike other systems.

Figures 31, 32:
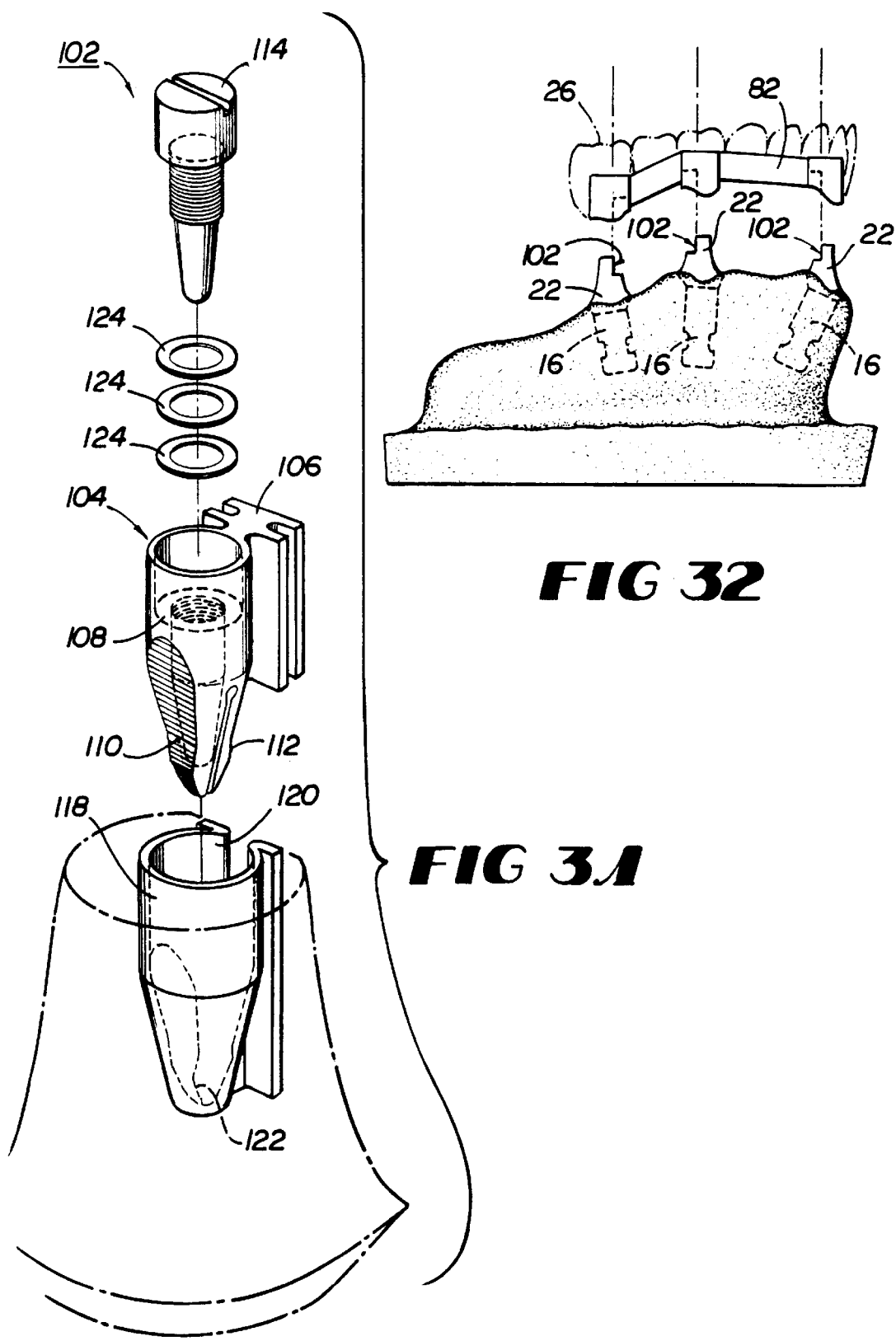
FIG. 31 is an exploded perspective view of a Vertex precision attachment according to the present invention.
FIG. 32 is an exploded cross sectional view of Vertex precision attachments employed for retention of a passive fitting prosthesis according to the present invention.
Figure 33:
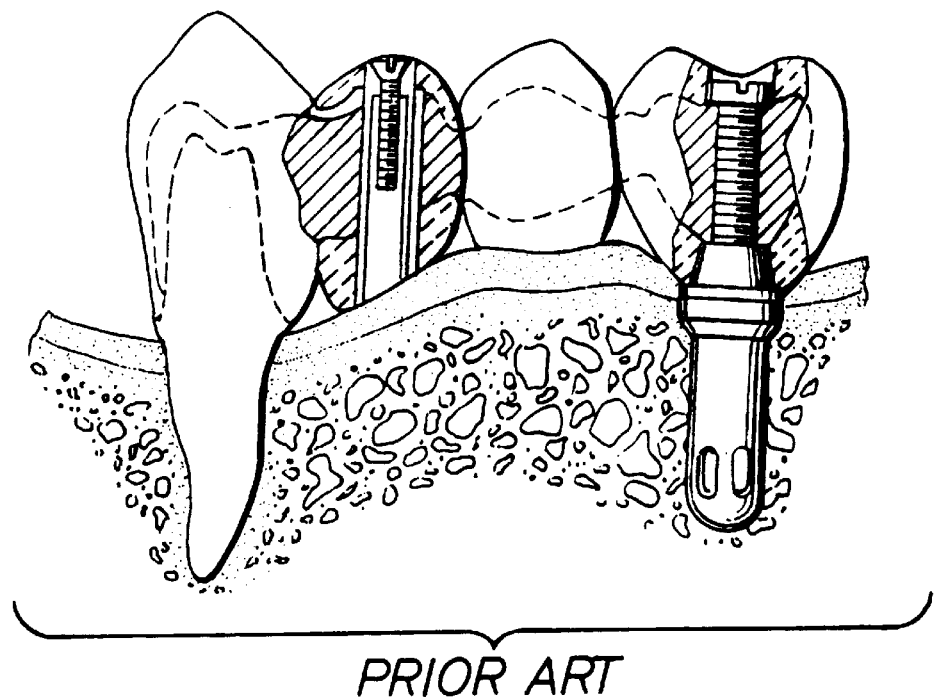
FIG. 33 is a cross sectional view of a prosthesis which employs conventional precision attachments and implant abutment systems that utilize an intra-mobile element.
Figure 34:
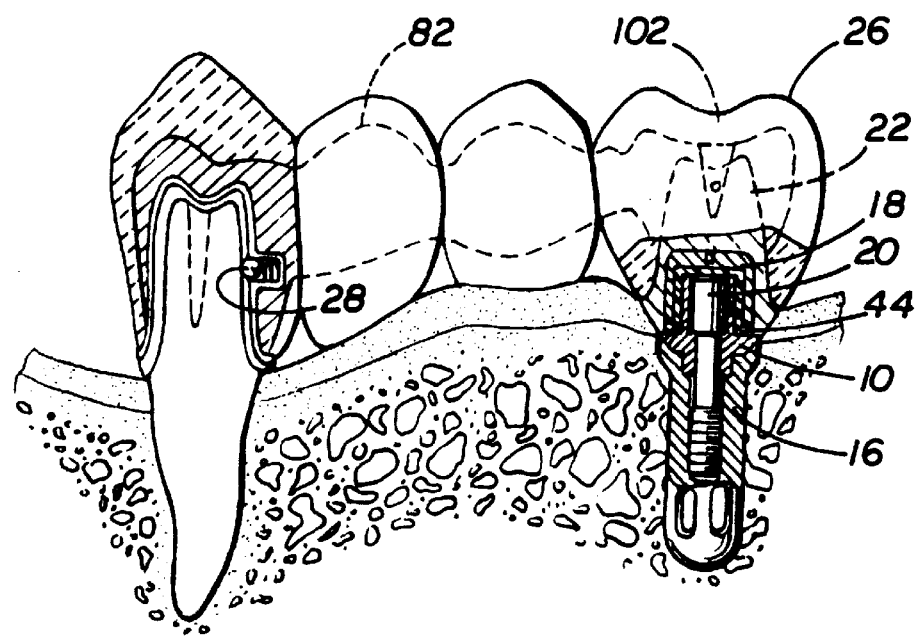
FIG. 34, by comparison, is a cross sectional view of a prosthesis similar to that of FIG. 33, but which employs precision attachments and an implant abutment according to the present invention (in the form of a modified Uniform Abutment System which employs a resilient core).

The UAS system can be used for many other applications as well, for example, alignment and parallelling of multiple abutments (see, e.g., FIG. 32). This system can also, as mentioned earlier, provide for placement of intra abutment precision slide attachments, set screws, grooves and ledges, which make the prosthesis patient removable.

Perhaps one of the most obvious choices for using the UAS system is in the restoration of the anterior teeth. Many reasons can be given as to why these crowns should be screw retrievable and not cementable, but perhaps the best reason is that the screw retrievable crown will allow repairs due to porcelain fracture or accidental breakage. It is also important to note that a screw-retrievable crown allows for proper soft tissue evaluation and calculus debridement around the implant base. Up until now, however, one of the biggest problems with the screw retained crowns has been causing the screws to emerge through the cingulum area of the anterior crowns. This has been the leading reason why so many crowns have been cemented. This off angle fixation screw often creates some very challenging situations for both the restorative dentist and the oral surgeon. Unless the implant can be placed at the exact angulation, the proper screw position is difficult to achieve. With other systems, if screw retrievability is essential, then the only way to correct for this angulation discrepancy without using a telescopic coping is to alter and cast to an existing prefabricated abutment or plastic sleeve. In this situation, a secondary set screw is used to redirect the screw emergence. Unfortunately, even if the proper angulation can be achieved using these methods, once again the use of these other abutments can lead to screw loosening and breakage.

The alternative solution is to use the UAS in conjunction with a secondary set screw such as a screw block which can be placed so that it exits perpendicular to the lingual framework of the crown. In fact, it can be placed in a horizontal position if the cingulum location interferes with a centric stop. An added feature of this system is that the set screw 42 can be placed into the wax abutment 21 without interfering with the fixation screw 20 and then cast to place, rather than tapped with a crude screw pitch into the abutment 22 after the fact. Lingual secondary set screw placement is rapidly becoming a common feature in other systems for it does not require a large access opening. However, with these other systems, major modifications are required.

With the UAS, no matter what the angle, the assembly allows for ideal screw position, full retrievability, a stronger abutment, no risk of screw loosening and a more simplified approach to treatment. There are fewer steps involved for the patient, dentist and technician when the UAS is employed.

Part 4: Resilient Core UAS

Another example of the UAS's flexibility is its ability, as shown for example in FIG. 6, to incorporate a resilient component 30, preferably in the core 18, which helps the implant 16 and abutment 22 replicate the periodontal membrane of natural teeth. This is particularly important when splinting ankylosed implants to mobile natural teeth because these resilient components 30 are able to absorb and distribute occlusal stress to the bone/implant interface more evenly than metal to metal implant components. If both the implants and the natural teeth are able to function in the same basic manner then combining them as part of the same prosthesis becomes more acceptable. There are other advantages gained by splinting natural teeth to implants, including: (1) providing the prosthesis with a sense of proprioception that hitherto only the intact periodontium of the natural dentition can provide; (2) unless the teeth and implants are splinted it becomes very difficult to equilibrate the patient's occlusion accurately as the teeth are mobile and the implants are rigid and (3) implants when splinted to periodontally compromised teeth provide added stability and support.

The IMZ Implant Company, perhaps among others, has developed a number of ways to splint implants and natural teeth using its Intra Mobile Element (IME). IMZ provides at least two versions of the IME: (1) its threaded IME whose external threads make direct contact with the internal threads of the implants and with which metal transmucosal tissue extensions may also be used, and (2) a newer version of the IME component referred to as "IMC" and which is disposed above a threaded metal transmucosal element. Both versions, however, have internal threads through which pass the main fixation screws. These fixation screws in fact pass directly through the overlying crowns, thus leaving external access bores. Not only are they unsightly but if even moderate angulation discrepancies exist between implant and crown, a complicated T block screw system must be employed to correct these discrepancies. This obviously involves more screws and more components. Furthermore, the use of a system with a central access bore precludes the use of intra abutment and intra coronal attachment prostheses. The IME components also contain a circular nonrotational upper sleeve which makes it impossible to reproduce a rotational position exactly, such as for a single tooth application or a precision attachment patient removable bridge. Another limitation is that conventional IME's have central access bores which obviously preclude the use of intra abutment precision attachments. The same problems of screw loosening apply to the IME as well, and the potential for screw breakage is greater because of the lengthy "vertical cantilever" that the main fixation screw demonstrates. The IME itself is very specific to the IMZ implant and therefore cannot be readily converted to be compatible with other implant systems. Furthermore, the upper sleeve of the IME is an unsupported projection of plastic which takes a tremendous load and is therefore at far greater risk of breakage. Dr. Howard Kay, a noted clinician, admits that "breakage of intra-mobile elements are not uncommon." H. B. Kay, *Free Standing Versus Implant—Tooth Interconnected Restorations: Understanding the Prosthodontic Perspective,* 13 Int'l J. of Periodontics and Restorative Dentistry 46–69 (No. 1, 1993). Kay also states that "the broken component can be readily retrieved and replaced" and that "I.M.E.'s break before undue stress is transferred to the implant/bore interface." Furthermore, IME's do not permit easy retrieval because in disassembling the prosthesis the main fixation screw has to be removed which totally removes any rotational stability the prosthesis may have had.

Another interesting limitation of the IME is that in order to splint the implant to the natural tooth, an extra coronal cantilevered screw attachment system must be used (which to begin with is bulky). However, there are situations where there is insufficient space between the implant and the natural tooth to place such a screw system, thus requiring the lab manually to "mill in" a thread into the crown in order to accommodate yet another screw. Once the IME's have been used to help splint natural teeth and implants together these screw systems make it virtually impossible to create patient removable prosthetics. This limitation creates problems associated with ridge lapping and is why posteriorly some create "high water" designed prostheses for periodontal access.

Another problem with the IMZ system is that all these screws create a "pre-stress" in the system and thus bending moments related to pre-loading and tightening down the screws. This in turn causes problems with passive fit.

The resilient core version of the UAS aims to address these problems, thus allowing more flexibility in design and performance.

When a "resilient core" 44 is incorporated into the UAS assembly, the assembly may be referred to as a "Modified UAS." The resilient core 44 is designed so that its internal threads mate with the threads of the UAS base 10. The external irregular, such as hex, shape of the resilient core 44 then engages a hollowed out correspondingly internally shaped metal core 18. The resilient core 44 is thus "sandwiched" between metal components leaving no unsupported plastic surface. The interface between the metal core 18 and the resilient core 44 depends on frictional retention but can be glued if desired with no effect on retrievability.

Once the metal core 18 has been placed on top of the resilient core 44 the assembly can then be customized in the same manner as the UAS was with one important difference. Before the metal core 18 and the wax abutment are invested and cast the resilient core 44 insert is removed so that it does not "melt". It can simply and easily be replaced after the casting procedure because alignment is guaranteed by the hex interconnections and the anti-rotational mechanism 24.

It is evident that when a resilient core 44 is utilized there are small but significant changes that must be incorporated into the design of the UAS base 10 and core 18. For example, the notch 40 in the base 10 must be deepened to accommodate for the resiliency of the resilient core 44. This helps prevent the ALS mechanisms 34 or 35 from bottoming out metal to metal which be antithetical to the purpose of the resilient core 44.

The Resilient Core UAS may, similar in some ways to the UAS, contain a projection 32 so that when the system is occlusally loaded this plastic projection 32 can deform into the hex hole of the fixation screw 20. It still, however, provides a surface against which the fixation screw 20 will, if it unscrews, bottom out against.

Once the metal core 18 has been customized and cast it becomes evident that there are once again no access bores and no need for screw attachment systems to join or splint the implants and natural teeth together. This means at least two things: (1) precision slide attachments can be incorporated to the customized Resilient Core UAS abutment and (2) because of the precision slide attachments the prostheses can be made patient removable which allows the prostheses to be ridgelapped and overcontoured if necessary for aesthetics.

Another small Resilient Core UAS modification to the UAS design is that the resilient core 44 may be threaded down onto a threaded base 10 which is designed with an extended 2 or 3 mm or more transmucosal collar. This design alteration allows the plastic insert to remain hygienically accessible in the peri-implant sulcus as shown in FIG. 6. Even though it is now visible, the beauty of the patient removable prosthetic design is that the resilient core 44 can be covered over and hidden by ridge lapping porcelain and metal without the associated risk of peri implantitis.

It is important to remember that the resilient core 44 does not interfere with the anti-loosening capability of this system for the following reasons, among others: (1) the modified UAS core 18 still has an internally recessed bore hole, against which the anti-locking mechanism 24 solidly rests so that it is stable and when the overlying crown is in place it cannot back out; and (2) as was mentioned earlier the projection 32 will still stop the fixation screw from backing out.

Part 5: Variable Height Universal Abutment Systems. The

The variable height UAS assembly is yet another example of the flexibility of the present invention. In situations where there is excessive soft tissue depth overlying the exposed implant there is a need to create a heightened or elongated version of the UAS base 10, the fixation screw 20 and the UAS core 18. If a resilient core 44 is to be used then an elongated resilient core 44 must also be fabricated.

The base 10 can be readily manufactured in different heights. The variable height base 10 would then have a varying number of external threads. The UAS core 18 would be machined accordingly.

As already mentioned, it is not uncommon to find areas in the mouth with varying thickness of tissue coverage, or where the implants are all placed at different heights. The variable height UAS was developed so that if there was 6, 7 or 8 millimeters of soft tissue coverage this assembly could provide a longer and more gradual taper. The variable height UAS was also designed to allow the notch of the variable height base 10 to be located at or near the gingival crest. This allows the crown margin to be extended below the anti-rotational mechanism 24 and secure the UAS.

The variable height UAS should be thought of as a tissue extension which simply adds more flexibility to the UAS.

Part 6: Conclusion.

Perhaps the biggest concern that clinicians face today regarding implant dentistry is its seemingly endless assortment of techniques, terminology and product. Each company has what it considers to be the most comprehensive range of prosthetic options. However, it is in the best interest of all these companies to simplify everything as much as possible. Unfortunately, the product catalogues seem to be getting bigger and more complex rather than smaller and simpler.

The UAS, on the other hand, is the simplest approach to retrievable implant prosthetics—it is also the most practical, especially when compared to some of the alternatives, such as the telescopic coping, the plastic sheath and/or the direct gold coping or the "altered abutment".

The UAS is a simple four piece system that can provide both the dentist and the lab technician with the greatest range of prosthetic options available. In fact this abutment system can be easily modified to replace the full range of all screw retrievable prosthetic abutments, including those that incorporate a Resilient component. This creates far less confusion for the dentist and the lab technician because there would be far fewer parts and more standardized procedures for all systems. This also means that there would be less inventory to contend with. From the manufacturer's point of view a superior job could be done with fewer machined parts giving rise to increased profitability.

There are many other advantages of the UAS. In the full arch situation, substructures are usually cast or soldered to one another creating a continuous metal framework that is either cemented or screwed down, allowing no individual access to the implant abutments themselves. This is not the case with the UAS, because their frameworks are made to be precision attachment patient removable which allows access around the individual abutments. This in turn makes oral hygiene easier. Cleansability is an important factor.

Because the UAS has no telescopic components, assembling and disassembling the device is also less time consuming, far less expensive and something the general restorative dentist should feel comfortable doing. As far as the dental lab and the dental implant companies are concerned, the UAS creates an unparalleled standardization of technique and inventory.

In fact, the UAS simplifies all crown and bridge procedures, whereas conventional telescopic systems complicate treatment considerably. As we will see later on, the UAS can be used in all types of implant reconstructions, not just crown and bridge applications. There is also less stress on the oral surgeon who is placing the implant fixtures when he or she has the flexibility to place the implants in the most appropriate surgical site, knowing that the axial inclination does not have to be such a critical decision when the restorative dentist is using a UAS.

Furthermore, the use of an auxiliary substructure to parallel abutments creates aesthetic compromises, for as the margin of the telescopic coping is brought more occlusally to parallel the coping, a metal collar which cannot be masked, appears. This problem does not occur with the UAS.

For the restorative dentist, a modified analog impression (see Section IV) of the implant fixtures at the time of uncovery is all that is required. With the UAS, abutment selection is not required. The UAS can be made to function in any number of ways. It could, in fact, be fabricated without a set screw or a precision slide attachment which would allow the dentist to cement the overlying crown for whatever reason.

It is this author's opinion, however, that most clinicians favor the fully retrievable assembly to the cementable system. Not only does the UAS significantly reduce the risk of screw breakage and screw loosening, but perhaps equally as important, it allows the clinician to make every prosthetic situation fully retrievable.

Up until now, various levels of retrievability have existed for case-specific reasons. However, it is the inventor's opinion that this exists only because of the design limitations of the specific prosthetic abutment systems. Those situations where the abutments are screwed in and the prosthetics are cemented are simply due to poor screw emergence patterns and compromising esthetics. Full retrievability only makes sense, for how would the clinician deal with a cemented prosthesis if there was a porcelain fracture? Certainly the clinician would not risk tapping or cutting the crown off and damaging the underlying implant assembly.

Up until now, companies and clinicians alike have been trying to deal with prosthetics using prefabricated abutment systems. Why? Crowns, inlays and veneers are not made in this manner—they are all custom made to fit each individual case. The abutment systems should be converted to include this same custom capability. After all, as clinicians we can all appreciate the difference between a prefabricated para-post and a customized gold cast post and core.

Many companies believe that they can create a custom abutment by casting to and altering a prefabricated titanium abutment. However, as we mentioned earlier this not only creates extra bulk but incorporates an oxidation layer. When precision attachments are to be incorporated into these abutment designs their central access bores also prevent them.

Waxing over top of a ground down abutment is a waste of both time and money, especially when the same result can be achieved by using less material and fewer steps. It is also important to remember that altering the path of draw of devices such as an HLA (Dentsply Hex Lock Abutment), places additional lateral stresses on its elongated fixation screw, which can lead to screw breakage. So, rather than complicating matters by waxing to an existing prefabricated abutment, the entire abutment system can be simplified by using a UAS.

As mentioned earlier, the same basic problems exist for the direct gold copings. However, they have the additional problems of dealing with screw loosening. Because this system, like the plastic waxable sheaths, has a direct connection to the implant, they are prone to screw loosening. The UAS is not. As far as the fixation screws are concerned, the longer the screw the greater the potential bending moment that the screw is subjected to. The shorter fixation screw of the UAS allows the assembly more readily to absorb the occlusal loading forces and resist breakage.

Secondary set screws are frequently employed in pre-manufactured angled abutments. The set screw threads come pre-tapped into the occlusal portion of the abutment. However, they usually come in only one height and are limited to a pre-set angulation (i.e., 3I's angled abutments). And so if the implant is severely angled or there is a lack of interocclusal space, then these abutments are of absolutely no use at all. With the UAS, the set screw can be placed in any position and at any angle.

Another important feature of the UAS is that the crown and the abutment can be removed without disturbing the rotational position of the prosthesis. The base 10 and the anti-rotational mechanism 24 always maintain their one exact rotational position for the UAS. This means that there is far less trouble in re-establishing the original orientation. This can save hours of lab and chairside time.

The UAS is the first truly universal abutment system because not only can this one system be used to design all types of implant prostheses from the single tooth and overdentures right on up to the removable crown and bridge appliances, but the UAS can also be made to fit every major implant system on the market today including both root form and blade form endosteal implants. In this respect it is the base 10 component that can be manufactured so that its machined interlock 14 "mates" exactly with the implant 16, whether it is an external or internal interlock, octagon, hex or tapered core.

Depending on the system, the mechanical interlock 14 between the base 10 and the implant 16 may change but the external threads of the base 10 and the core 18 always remain as a constant no matter what implant is used. Because of this common feature this system can "blend" different implants into the same prosthesis. Furthermore, it also allows a resilient core 44 component to be compatible with any system on the market because it fits on top of the base 10. This creates a brand new market for a lot of companies.

The UMA (Universal Modification Abutment) from Attachments International claims to have the same type of universality but, upon closer examination, the UMA still has the problems of an exposed central access bore hole. Furthermore, the UMA is screwed into the implant and there is nothing stopping it from unscrewing, for there is no mechanical interlock between it and the implant. Therefore, the UMA may be compatible with other implant systems however, it has a very limited application because it shares the same conventional problems that face the rest of the abutments.

Finally, the flexibility of this UAS will be further demonstrated in Section V which describes a unique new process that allows customized UAS's to be constructed in the dental lab from a pre-machined block of titanium using CAD/CAM technology according to the present invention. These new custom milled abutments are called "Milled or Machined Universal Abutment Systems" ("MUAS").

Section IV: The Tapered Transmucosal Gingivectomy, the Modified Impression Coping, the Locking Healing Collar and the Universal Abutment Systems: A Combined Technique to Eliminate the Need for Ridge Lap Prosthetics in Implant Dentistry.

Part 1: Introduction.

The use of a Tapered Transmucosal Gingivectomy procedure in conjunction with a Locking Healing Collar, both according to the present invention, and UAS/MUAS Assemblies can eliminate the need to ridge lap implant supported crowns that are either cemented or screwed into place. This combined technique also ensures proper cervical margin placement, soft tissue emergence profile and hygiene access. This procedure can be achieved without flapping or elevating the periosteum, which allows the soft tissue and the bond to heal faster. This. Locking Healing Collar is designed to hold the gingival tissues in any number of fully customized anatomically contoured shapes—the outline of which is determined by the Tapered Transmucosal Gingivectomy procedure according to the present invention. And finally, because the peri implant sulcus has been tapered and contoured the final prothesis can be secured into place without ridge lapping the tissue which effectively eliminates the risk of peri implantitis.

In 1990 there were between 550–650,000 implants placed in the United States alone; as more and more implants are placed, the need to create aesthetic and hygienic restoration grows. J. E. Bentley, *Surgical Dental Implants*, J.A.D.A. (Monograph, August 1993). Up until now, the options for creating aesthetic restoration have been very limited. One of the biggest concerns is the constricted emergence profile of the implant supported crown, which frequently creates a need aesthetically to ridge lap the tissue which in turn creates a hygienic access problem. This is especially true in those situations where the clinician chooses to make the restoration screw retrievable.

The conventional UCLA abutments and other direct connection abutments presently on the market aim to create a more divergent restoration by starting the crown contours well below the gingival crest. The hope was that this would allow for a more natural soft tissue emergence profile. The proponents of the UCLA system claim that this would eliminate the need to ridge lap the tissue as much. Unfortunately this system and others like it cannot totally eliminate ridge lapping, for this requires modification to both the abutment system and the surrounding soft tissues. (Many articles about the UCLA abutment still picture ridge-lapped crowns.) J. Beumer III and S. G. Lewis, *The Branemark Implant System: Clinical and Laboratory Procedures* ch. (FIGS. 149A and B, 150, 151), pp. 228–29 (Ishiyaku Euro-America 1989).

Because a universal solution to the constricted neck of the crown has not been found, restorations are either designed in a high water fashion or ridge lapped. For aesthetic reasons, ridge lapping the tissue has gained in popularity in recent years, but once again the concern that ridge lapping creates is that it smothers the peri implant sulcus and makes it extremely difficult to cleanse. Ridge lapping does create more ideal contours and cervical margin placement, as well as the "appearance" of good soft tissue emergence, but, it does so at the expense of the gingival tissue and can frequently lead to peri implantitis.

The solution to this problem has two parts: (1) use of an abutment system that starts diverging down by the implant and that can accurately replicate the more anatomically contoured shapes of the tissue; and (2) (in order to create these more anatomic contours) the tissue itself also must be altered. Precursors to this technique have shown promising results but have required periosteal elevation, placement of a standardized conventional healing collar, and subsequent to that placement, modification of the transmucosal tissues. H. Israelson, J. Plemons, *Dental Implants: Regenerative Techniques and Periodontal Plastic Surgery to Restore Maxillary Anterior Esthetics*, 8 Int'l. J. of Maxillofacial Implants, 555–61 (No. 5 1993).

By using the Tapered Gingivectomy Technique, the Modified Impression Coping, the Locking Healing Collar and a UAS or MUAS Abutment according to the present invention, exacting control over the shape of the peri implant sulcus and the crown emergence contour can be achieved.

Part 2: The Tapered Transmucosal Gingivectomy: Description of the Technique.

With this technique, it is important to ensure that all necessary steps have been taken to create a "fully contoured" edentulous space over top of the implant. If the ridge is not fully contoured the gingivectomy procedure should not be performed. Thus, it behooves the surgeon and the restorative dentist carefully to pre-plan the treatment and determine beforehand whether or not the implant placement will require bone augmentation and guided tissue regeneration.

Figure 23:
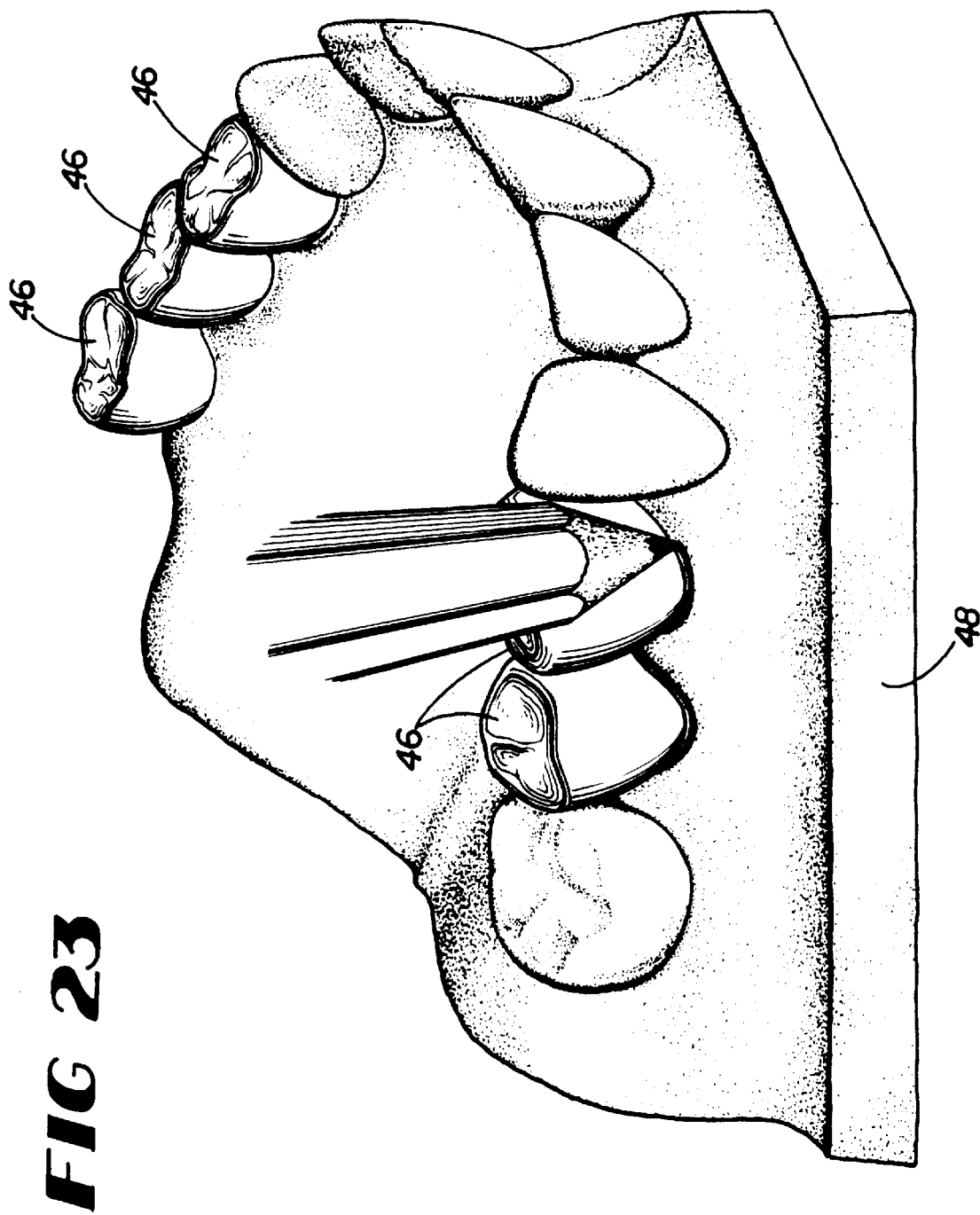
FIG. 23 is a perspective view of a stone model on which wax up contours are being outlined in accordance with Tapered Gingivectomy procedures according to the present invention.

Assuming that the ridge has been properly prepared, then 3–4 months after the initial implant placement an impression of the implanted arch is taken and poured in stone to create stone model #2. Using accurate full contoured diagnostic wax ups 46, the missing teeth to be replaced are added to the stone model #2 and an outline of their scalloped asymmetrical gingival contours are then traced in pencil onto the stone model 48 as shown in FIG. 23. The wax patterns can then be carefully removed and put aside, and the pencil lines can be extended interproximally, without the lines touching so as to provide room for the papillae. A red line is then carefully extended 1–2 mm inside the black pencil lines, but reproducing the same curved asymmetrical shape. This is a crucial step for two reasons: (1) it helps establish a snug fit between the gingival tissues and the final prothesis, and (2) it is the development of these asymmetrical scalloped contours that give rise to the unique shapes of the Tapered Gingivectomies and is what sets them apart from the cuff shapes that the conventional symmetrical healing collars create.

Figure 24:
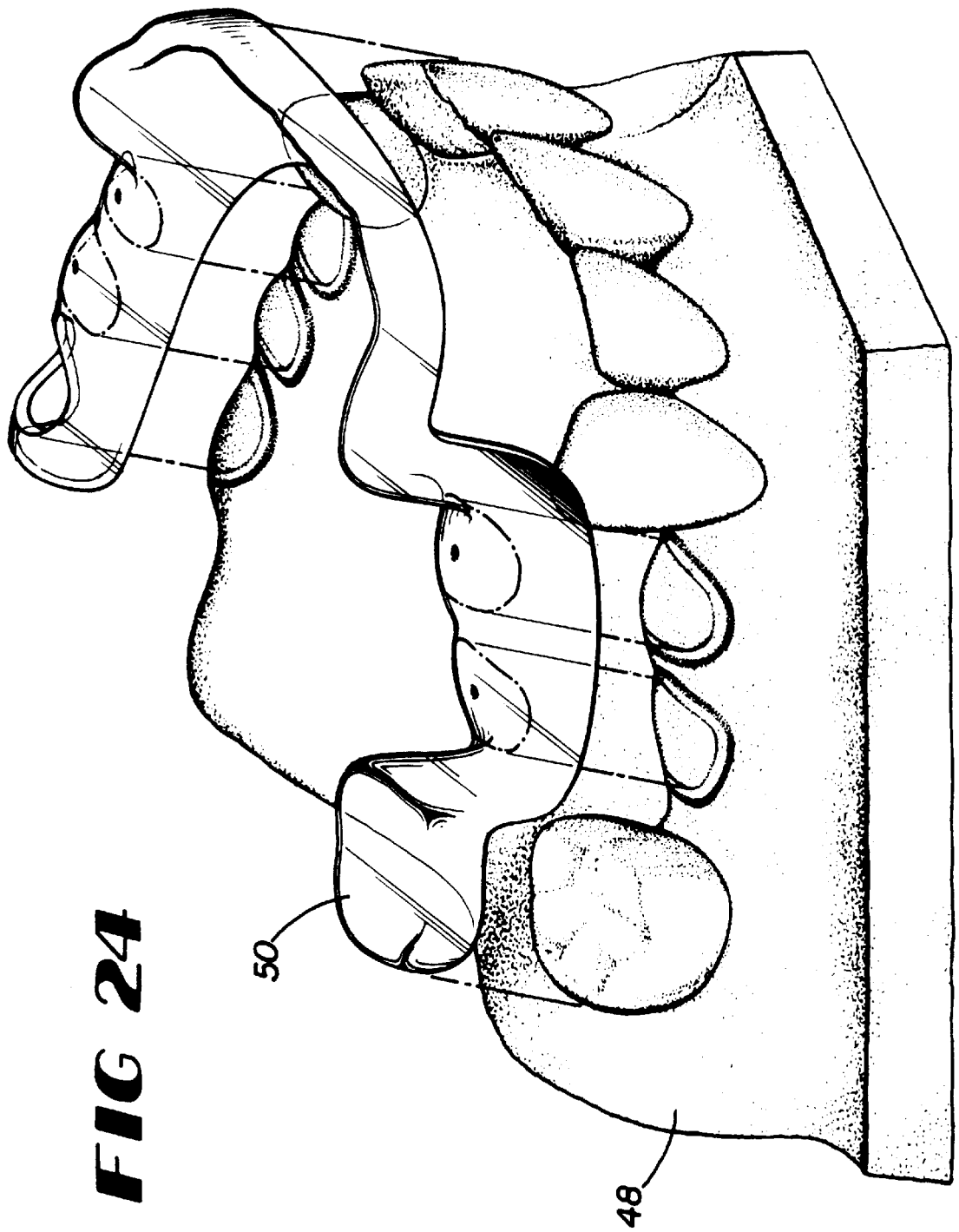
FIG. 24 is a perspective view showing a Tapered Gingivectomy Template used in Tapered Gingivectomy procedures according to the present invention.

A template is then pulled down over this Model #2 and the red lines are again carefully traced onto the clear template, which is referred to as the "gingivectomy template" 50 as shown in FIG. 24. Next, that portion of the gingivectomy template 50 inside the red line is cut out and carefully trimmed back until the operator can barely see the outside edge of the red line which leaves a small amount of the template overhanging the red lines on the model. Before the template 50 is completely cut back flush with the model #2 48, the depth of soft tissue covering the implant 16 must be recorded on the model 48. This can be done at either of two times: (1) by the oral surgeon at the time of implant placement, at which stage a fairly accurate measurement of soft tissue depth can be provided; or (2) after the implant surgery when the gum has healed, the patient's tissue can be probed down to the depth of the cover screw. Either way is acceptable—an x-ray can also be of great help.

The depth measurement is transferred to the model #2 by creating a depth cut in the center of the template hole. That portion of the overhanging gingivectomy template 50 can now be removed in the following manner. Specially tapered lab burs or conventional burs are used to hollow out the stone model area within the template hole down to the depth cut, and with light lateral pressure on the bur the template is quickly expanded until it is flush with the red lines on the model #2. As a result, the conically shaped burs not only create a natural asymmetrical taper on the model 48 but also on the walls of the template 50. This taper acts as the surgical guide for the Tapered Gingivectomy procedure. The template 50 is now complete and can be cold sterilized in the appropriate manner before it is taken to the mouth.

Part 3: Locating the Implants.

Using the original surgical template from model #1 the clinician should be able to locate the center of the implants and mark the overlying soft tissue with an indelible marker. If the surgical template is not accurate due to anatomical or surgical corrections that were made at the time of the implant surgery, then a periodontal probe, an Nd: YAG laser, the Siemens Periotest or other means can be used to locate the implants and they can be marked accordingly.

Once all the implants have been "marked" the Gingivectomy Template 50 can be inserted into the patient's mouth. The first thing the clinician checks for is to see whether or not all the implant markers lie within the holes of the template. To start, the clinician should only work on those that line up. It is important to make sure that all of the implants have a solid band of attached gingivae up to and beyond the periphery of the template holes. If there is inadequate attached gingivae—stop. Autogenous gingival grafts must be placed before one can proceed any further. Assuming that this has now been done, or that there was initially adequate attached gingivae, the next step is to take a small tissue punch and remove a tissue plug, while staying within the confines of the template holes. This should expose the implant cover screw. The cover screw can then be removed; however, if there is new bone growth over the top of the implant, then it must be carefully removed with a low speed bur. After the screw has been removed any and all tissue tags around the implant are also removed.

This is usually the extent of uncovery with a tissue punch, the result being an exposed implant with a straight or slightly flared but symmetrical gingival cuff. Up until now the only other alternative has been to raise a flap and lift the periosteum. However, this is a very risky procedure in the inventor's opinion because no matter how conservative the flap design the operator runs the risk of disturbing the periosteum and damaging the blood flow to the implant-bone interface. This can have damaging effects if the implant is bone loaded incorrectly or prematurely. The Healing Collars that are placed when the tissue is flapped are all symmetrical. Some of the very latest designs such as the 3I healing collars have a flared shape to them but their cross sectional shape is still round. R. J. Lazzara, *Managing The Soft Tissue Margin: The Key To Implant Aesthetics,* 5 Practical Periodontics and Aesthetic Dentistry 1–7 (No. 5, 1993). This does not accurately reflect the shape of a natural looking crown and its supporting soft tissue. Furthermore, the healing collars and transfer analogs are the same size and shape which means that the final prosthesis will not expand the tissue at all. This will create a lack of tension around the gingival tissue and allow for potential food and bacterial entrapment.

Assuming that the tissue plug has been removed and the gingivectomy template 50 is in place one cannot help but notice the large irregular amount of tissue that appears between the tissue punch hole and the hole in the template. In some cases there is only a small amount of excess tissue but in other areas there are significant amounts. It is at this stage that the clinician can begin to appreciate the difference between creating a standard symmetrical gingival cuff and a customized gingival cuff shape that is different for every tooth/implant according to the present invention.

It is this excess tissue that must be removed down to the constricted neck of the implant to create the asymmetrical naturally contoured Tapered Transmucosal Gingivectomy. This can be done carefully with a scalpel while pressing down on the template 50 to keep the tissue firmly in position or with the aid of special gingivectomy burs. There is also new clinical support mounting for the use of the $CO_2$ and Nd: YAG lasers. If these lasers could be used without risk of damaging the implant it may prove to be an effective method of performing the Tapered Gingivectomy.

Figure 25A:
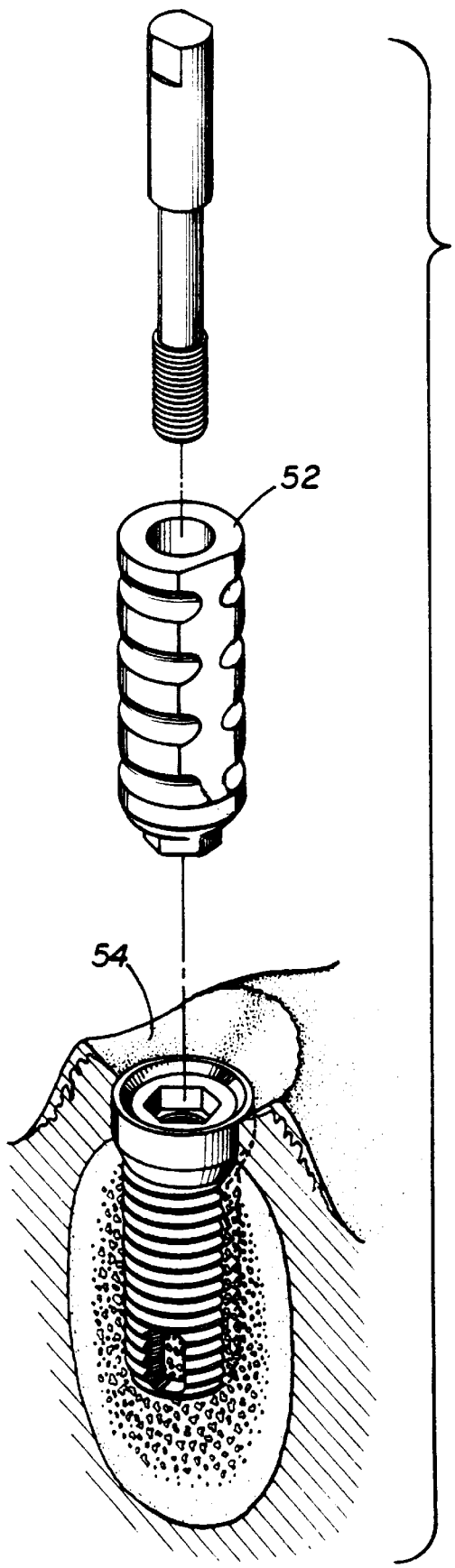
FIG. 25A is an exploded cross sectional view of a Modified Impression Coping according to the present invention.

After the Tapered Gingivectomy has been performed the template 50 can be removed. Once the hemorrhage has been controlled appropriately sized Modified Impression Copings 52 as shown in FIG. 25 can be placed into the implants 16 and screwed down firmly to seat. The unique design of these copings 52 allows the operator to get an accurate impression of the surrounding tapered transmucosal tissue 54 and at the same time get a transfer impression of the implants' position. This can all be accomplished in one simple procedure because the flat side of the copings 52 help create rotational accuracy and the annular rings which extend below the gum line help create an accurate impression of the tapered tissue 54.

Figure 25B:
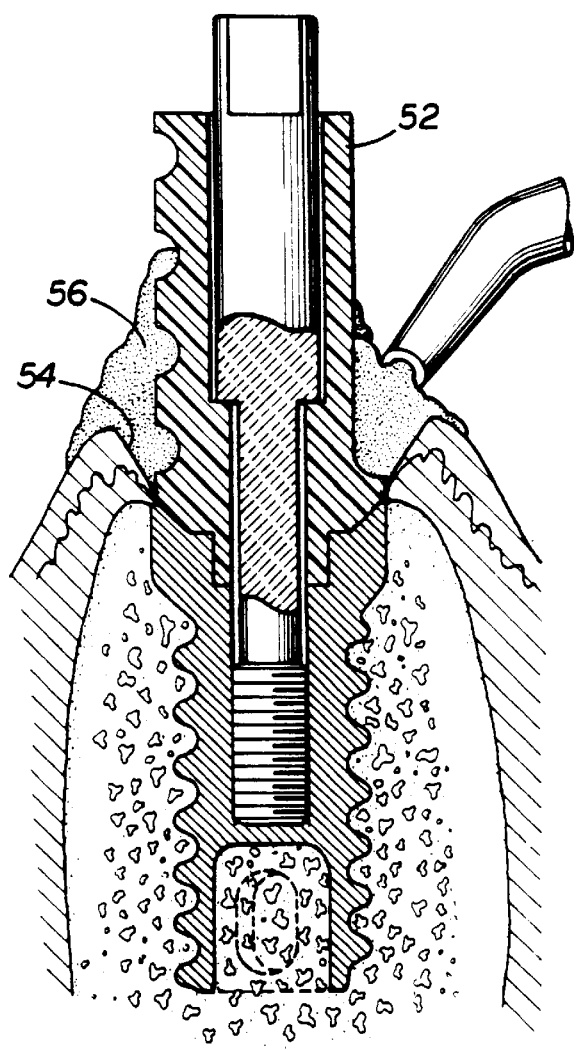
FIG. 25B is a cross sectional view of the coping of FIG. 25A being syringed with material to form an impression.

The impression is usually taken with a polyvinylsiloxane material 56 and with the Modified Impression Copings 52 in place as shown in FIG. 25B. The material 56 is carefully syringed around the base of the copings 52 and once the material has set the clinician has an accurate impression of both the implant 16 and the surrounding tissue 54. Even if the copings 52 are in perfect alignment a direct analog impression technique is preferred so as not to disturb the impression. There is considerable potential inaccuracy in repositioning the copings 52 back into the impression (indirect transfer analog impression technique) and such repositioning should therefore be avoided if at all possible. As discussed below in this Section, the direct analog impression technique is not always possible, especially when the implants are severely angled such as in the posterior less accessible areas of the mouth. Once the copings 52 have been unscrewed and removed a set of UAS base 10's and fixation screws 20, described in Section III above, and which can later be retrieved and reused, are inserted into the implants 16 and Barricaid light activated periodontal wound dressing is syringed around them. This material serves to hold the tissue 54 in place and allows initial healing until the Customized Locking Healing Collars 58 according to the present invention have been fabricated. The patient's denture or temporary is hollowed out and relined to accommodate the threaded base 10's and Barricaid.

Figure 27A:
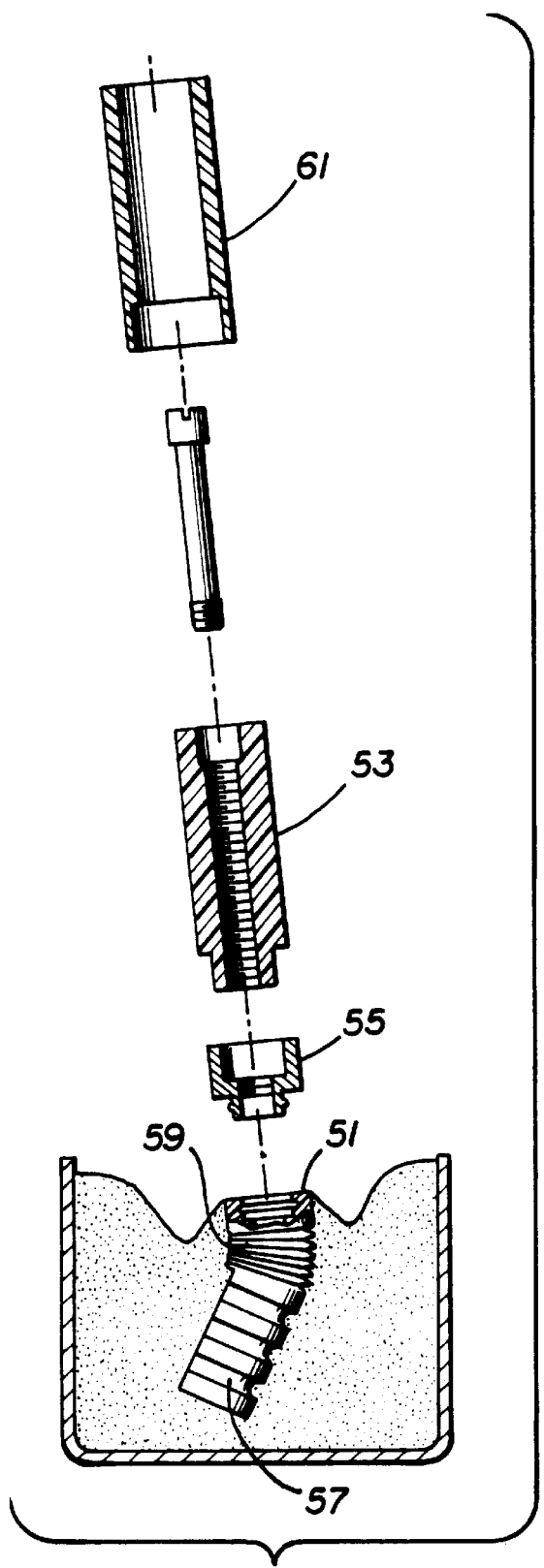
FIG. 27A is a cross sectional view of a Modified Implant Analog according to the present invention.
Figure 27B:
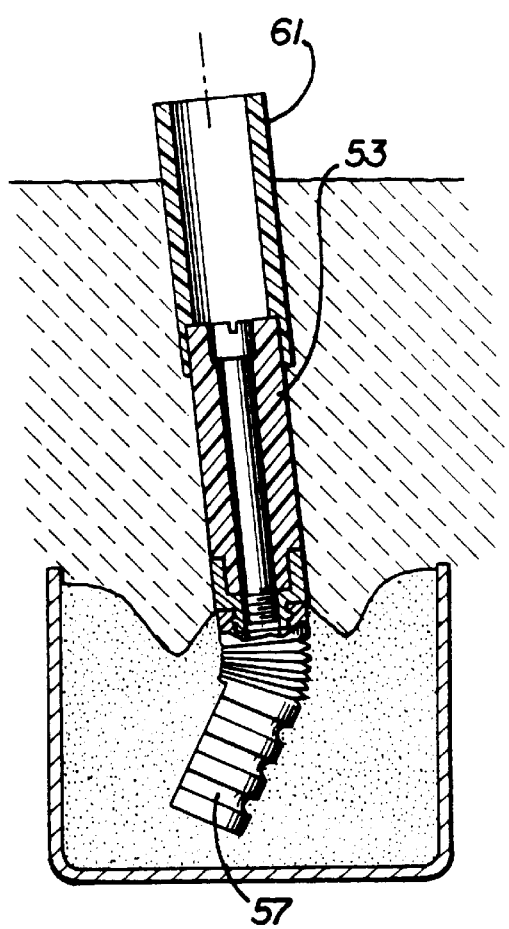
FIG. 27B is a cross sectional view of the Modified Implant Analog of FIG. 27A attached to a Flexible Modified Impression Coping.

Modified Implant Analogs 53 as shown in FIG. 27 and as discussed below can then be attached to the Modified Impression Copings 52 in the impression and the impression can then be poured in a dental stone. This model is referred to as the Master Model #3.

A Flexible Modified Impression Coping 51 according to the present invention may be required when creating a tapered gingivectomy around an off angle implant. See FIGS. 26A and B. As far as misaligned implants are concerned: If when the Tapered Gingivectomy Template is placed, the implant 16 appears to be slightly beyond the hole, a tissue punch cannot be used. Instead, a scalpel or other implement must be taken and angled through the template hole to gain access to the implant 16. This creates a tapered transmucosal cuff with a slight undercut. This undercut, however, is removed when model #3 is lab altered. If a standard impression coping or even one of the inventor's MIC's were used in this situation, it would press or penetrate through the gum at some point beyond the tapered cuff. A normal MIC would extend straight out of the off angled implant and not only distort the Tapered Gingivectomy but could also create the wrong soft tissue emergence position. In off angle situations, especially in the back of the mouth, this also makes it difficult to get a direct transfer analog impression. This is what frequently gives rise to crowns with exposed transmucosal necks or oddly contoured cervical (neck) contours.

The solution to this problem is a Flexible Modified Impression Coping 51 according to the present invention ("Flexible MIC"). The base 55 of the Flexible MIC is similar mechanically and in appearance to the metal base of the Locking Healing Collar, perhaps with a lower profile flange. Onto this base a flexible plastic tube or coping 57 can be positioned. Normally this plastic tube would have to be screw retained to the metal base. The plastic coping 57 may, however, feature an internal machined metal snap interlock which is both precision fitted and removable. The outside wall of this plastic coping 57 has a pleated collapsible section 59 which allows the sheath to be bent.

Once the Flexible MIC 51 has been bent into position so that it exits through the tapered gingivectomy hole and so that impression material can be syringed around its base, (see FIGS. 26A and B) it must be rigidly fixed to place. This is achieved by simply providing light cured acrylic down the 'hollow' of the sheath (the head of the fixation screw must first be lubricated). Once the acrylic sets up it holds the Flexible MIC 51 rigidly in position. Once impression material has been syringed around the tapered cuff to capture its contour and the material has set up around it, the Flexible MIC 51 will snap off the metal base when the impression is removed remaining firmly anchored in the impression.

The advantages of these Flexible MICs are at least threefold.

(1) They allow for all impression copings to be aligned parallel or near parallel, which circumvents the problems associated with inaccuracy and impression taking of off-angle copings.

(2) The Snap Removable Flexible MIC creates the ability to remove this MIC sheath off of the metal base and be held accurately in the impression.

(3) They allow the integrity of the Tapered Gingivectomy to be maintained, transferred to Model #3 and then lab altered as usual even if it is undercut.

Once the metal base has been unscrewed from the mouth, it can be attached to a modified impression analog 53 ("MIA") (FIG. 27).

Once the MIA 53 is assembled to the base of the flexible MIC, a plastic tube 61 is snapped onto the distal end of the MIA 53 (the end poking out of the impression). This assembly (metal base/MIA/screw/plastic tube) can now be snapped into the flexible MIC plastic coping 57 which is housed in the impression. Exact rotational position is maintained by simply aligning a small groove present in both the metal base and the flexible MIC plastic sheath. The assembly is left poking up at an odd angle out of the impression. Die stone can now be poured into the impression and around the assembly. Die stone must never be poured above the level of the plastic sheath attached to the MIA as this channel provides access to the screw holding the assembly together. When there is more than one flexible MIC and MIA, assembly the stone is only poured up to the top but not beyond the level of the lowest plastic tube. Once the stone is set, the impression tray can be removed and with it the flexible MIC sheath snaps off of the metal base. The Master Model #3 can be carefully turned over and the MIA screws backed out. This will allow the metal bases to be removed and will leave the Modified Implant Analogs in the Master Model #3 complete with their surrounding Tapered Gingival Cuffs which can then be lab altered.

One of the most important features of the MIA system is that after the lab altering procedure is completed and healing collars have been made, it allows the UAS wax up to be held securely in position from the underside of Master Model #3. This means that the base 10 and core 18 do not have to be anchored to the implant 16 by the fixation screw 20. This further means that once the UAS core 18 is waxed up, the core 18 and the base 10 do not have to be unscrewed from one another. They can simply be pulled straight off the model. This preserves the anatomically asymmetrical taper of the wax up. This can only be done using an MIA but requires that the MIA screw be undone before attempting to remove the UAS wax up.

As was mentioned earlier, a most important feature of the flexible MIC is that it allows all of the impression copings in the mouth to be aligned. In the posterior jaw, where there is limited access, screwing standard impression copings to place is not only difficult to do but if they are off angle, the risk of distortion is increased.

Whether the impression contains Flexible MIC's or MIC's, it is then repoured using a new set of regular implant analogs, but this time with a GI soft tissue mask around the implants. This Model is referred to as Model #4 and its significance will become apparent later.

On Master Model #3 the modified implant analogs and the tapered transmucosal sulcus should now be evident. They may appear to be somewhat jagged in shape but they accurately represent what is in the mouth. This Master Model #3 must now be "lab altered" to recreate the customized gingival tapers. This is why the red line was drawn inside the fully contoured pencil lines, so it could now be enlarged. This full anatomical taper on the Model #3 will allow the customized healing collars to stretch the gingival tissue to full contour without damaging the tissue and at the same time create a snug fitting gingival cuff.

To lab alter Model #3 accurately, the Gingivectomy Template 54 must be used. It is first replaced on Model #2 and the full contour black pencil lines are traced onto the template 54. The template is then enlarged until the black traced line is removed. The template now represents "full anatomical contour" and can be positioned on Model #3 so that the contours of this model can also be enlarged using conventional or special gingivectomy lab burs with rubber tips that protect the modified implant analogs from damage while the contours are being enlarged. Once these contour changes have been made, the diagnostic wax ups 46 can be positioned on the Master Model #3 to confirm that it accurately represents "full anatomical contour." Master Model #3 can now be referred to as "Lab Altered Model #3".

Locking Healing Collars 58 as shown in FIG. 1 may now be inserted into Lab Altered Model #3. Such collars 58 include a base 60, preferably formed of a non-oxidizing metal (such as Ceramicor), which is adapted, as in the UAS base 10, to engage the top of the implants 16 in locking fashion, and unlike the UAS base 10, to receive a plastic sleeve 62 in its upper portion. [These will be secured in place in the mouth to the implant 16 by a fixation screw 64 (which shoulders on the inside of the plastic sleeve 62).] On model #3, wax can now be added to both the metal base 60 and the plastic sleeve 62 of the Healing Collar 58 to create a more divergent collar and one that fills the "lab altered cuff". Annular rings on the wall of the plastic sleeve 62 help ensure that the wax pattern is anchored solidly to the Healing Collar 58. The wax pattern that is formed on the outside of the plastic sleeve 62 is built up to the crest of the cuff, and the sleeve 62 is left extending up beyond the wax pattern so that a prothesis can later be attached. The fixation screw 64 which shoulders on the inside of the sleeve 62 can be removed, as the wax pattern now holds the metal base 60 and the sleeve 62 together as one unit, and is now ready to be invested. The inside of the sleeve 62 can either be invested and the screw seat redefined after casting with a reamer, or an alternative method can be used to remove the fixation screw and insert a graphite or ceramic analog which can be cast to and then sandblasted out afterwards. If the metal base 60 is made of a non-oxidizing material such as ceramicor or platinum iridium, the wax pattern and sleeve can be cast to it in Type IV gold which creates a strong metallurgical bond and is biocompatible with the titanium implant.

The newly cast Locking Healing Collars 58 can be polished and returned to the patient's mouth whereupon the Barricaid can be removed and the Locking Healing Collars 58 secured to place. As was mentioned earlier, the unique design of these Locking Healing Collars 58 allows the slightly oversized collars to fit snugly into the mouth compressing the tissue just enough to provide a firm fit. Note that some blanching does occur but excessive pressure is prevented by controlling the contours in the mouth and on lab altered model #3. If excessive pressure is applied this can lead to gingival clefting and recession. This is a common problem with many of the existing abutment systems. They force the technician arbitrarily to create arbitrary anatomic shapes without first tapering the tissue slightly and second, accurately contouring and customizing the healing collars.

As was mentioned earlier, 3I has attempted to solve this problem by recently developing large tapered healing collars and implant transfer copings. The problem with 3I's approach is that the healing collars are symmetrical and therefore do not represent anatomically correct soft tissue contours. Furthermore, the healing collars and the transfer copings have already determined the full soft tissue contours for the crown before the master model has even been created. This means that the crown ends up being the same shape as the healing collar—a standard symmetrical shape.

With the Locking Healing Collars 58 in place the tissue has now reached its full anatomical contour and is given several weeks to heal. The Healing Collars 58 are then progressively loaded. In the partially edentulous situation or the single tooth replacement situation, the temporaries are in fact left out of occlusion for the first few weeks.

It must also be remembered that in the completely edentulous situation the Tapered Gingivectomies are not performed but the Locking Healing Collars 58 are still placed and the denture is simply relined with a soft liner.

If necessary a screw block can be added into the hollow open end of the Locking Healing Collar sleeves 62 so that temporaries can also be screw retained. Either resin temporaries with non-precious metal cores can be used to add stability and strength or normal heat processed temporaries can be used to load the bony architecture progressively. As was discussed earlier in Section I these temporaries can remain in place for upwards of 3–4 months.

Once this healing phase has been observed the final restorations can be fabricated. However, the exception to this rule is in the fully edentulous situation where there are no custom tapered transmucosal cuffs and the final abutments can be placed at an earlier stage to anchor the interim denture (as discussed in Section I).

Note that in all other situations where these gingivectomies have been performed new impressions do not need to be taken after the healing phase for two reasons: (1) there is very limited tissue shrinkage with the Tapered Transmucosal Gingivectomy technique, and (2) the lab altered contours are already present on Lab Altered Model #3.

However, before the final abutments and prosthesis can be fabricated one final alteration must be made to Lab Altered Model #3, which has to do with the appearance of the tissue in the patient's mouth around the Locking Healing Collars 58. Remember that the Locking Healing Collars 58 are structured so that their flat base portion on which the temporary sat is level with the gingival margin on the stone model. Frequently, however, the gingival tissue does shrink, ever so slightly, and because the base of the Locking Healing Collar 58 was initially fabricated level with the gingival crest this can be examined intra-orally and any shrinkage can be compensated for on Model #3. This is simply done by shaving down the occlusal gingival height of the cuff on the model by a millimeter or more, especially at the labial or interproximal sites. When the final abutment margin is prepared it is level to Model #3 which is now lower than the gingival margin in the mouth. In effect the clinician is "lab altering the Lab Altered Model #3" one final time. After this has been done, it can be referred to as the "Final Lab Altered Model #3". This shrinkage of tissue is but one more very good reason why the fabrication of the final prothesis should not be rushed. With existing technology, new soft tissue impressions would be necessary especially when the tissue is flapped to expose the implants and allows for tissue shrinkage.

As an added control step, the customized abutments with their final margin placement can be tried in to reconfirm proper margin location. If necessary the margin can easily be altered.

In order to ensure that the abutments 22 and the crowns 26 will be divergent enough to fill the custom tapered gingival cuff 54, UAS or MUAS assemblies must be used (See Section III & V). A direct connection abutment such as the UCLA is not recommended because: (a) of problems with screw loosening and access base location, and (b) they are direct connection abutments and to create a tapered crown their margin starts 1 mm above the neck of the implant which is difficult to check clinically when the soft tissue coverage is 3–4 or more mm thick. Prefabricated abutments with so-called more anatomically correct contours such as those that 3I endorse cannot be used because they are prefabricated and cannot reproduce the individualized custom tapers and contours of the tapered transmucosal cuff. Furthermore, these 3I abutments, like virtually every other abutment system on the market, also have central access bore and screw loosening problems. The only logical choice is the UAS or MUAS assemblies so that contours can be developed to match the gingival tissue exactly. There is also no worry of screw loosening with these assemblies.

When the UAS/MUAS abutments are ready to be fabricated, the importance of Soft Tissue Model #4 becomes apparent. Because of the design of the UAS core 18, once it is cast to form the customized taper it is often asymmetrical and therefore will not thread down to place on the stone die of "Final Label Altered Model #3." This is why Soft Tissue Model #4 is required. On Model #4 the core abutment 22 can expand the flexible GI Mask and allow for complete seating of the components. Furthermore, Model #4's soft tissue profile has not been altered like Model #3 and so this allows an accurate means of checking the final crowns 26, margin placement and emergence contours.

It should be emphasized that when the wax UAS abutment 21 is being contoured to the "Final Lab Altered Model #3," once the wax up is complete it cannot be rotated off of the Model without breaking the wax pattern. The reason once again has to do with the customized asymmetrical tapers that are being created on this Model. There are two solutions to this problem: First, before the core 18 is screwed down onto the base 10 the threaded base 10 must be firmly anchored to the implant analogue. This is achieved by tightening down the fixation screw until the machined interlock 14 is fully engaged. The fixation screw 20 is then backed out. If the machined interlock 14 does not have a Moore's Taper incorporated into its design, the base 10 must be secured down with a little sticky wax. Only then can the core 18 be threaded down to place. After the wax abutment 21 has been created and the anti-loosening screw is in place the entire core 18 and base 10 can be lifted straight out of the implant analog by holding firmly onto the ALS mechanisms 34 or 35. This prevents having to rotate the wax pattern off of the stone model and damaging the wax pattern.. Second, a Modified Implant Analog (described earlier) can be placed which allows the UAS base 10 to be temporarily anchored from the underside of final lab altered master model #3. Before the base 10 and core 18 can be removed, the MIA screw must be backed out.

It is in situations such as these that conventional systems are limited, for they feature less flexibility to address off angle or customized contoured cases.

With the MUAS System, since there is no waxing or casting to the components, this is not even an issue. After the custom tapered wax pattern has been cast (UAS) or the abutment has been custom milled from a premachined titanium blank (MUAS), the abutments 22 can be screwed down onto the threaded base 10's on Model #4 because its gingival cuff is made of an elastic deformable GI mask material.

Part 4: Fabrication of the Overlying Crown.

The UAS or MUAS base 10's can also be secured down with a fixation screw 20 onto an analog and the abutment 22 can again be secured to the base 10. In this fashion, the components can be handled as if they were an individual die onto which a framework and porcelain can be built up using the transmucosal taper of the abutment 22 as a guide for proper contour. Model #3 can also be used to create the proper emergence profile and occlusion for the crowns 26.

Part 5: Conclusion.

It is evident that there is a need for the Tapered Transmucosal Gingivectomy procedure in the partially edentulous jaw, and it is important to note that by custom tapering the transmucosal cuff the clinician can enjoy the following advantages, among others:

1. Make the peri-implant sulcus more accessible for oral hygiene purposes.
2. Provide better aesthetics than ridge lapping for the crown can now truly emerge through the gingivae with the cervical contours of a natural tooth.
3. Eliminate the need for ridge lap prosthetics which many clinicians believe is one of the leading causes of peri implantitis.
4. Provide more natural lingual contours since the relief of the palato-gingival area is not required for hygiene access.
5. Avoid unnecessary periosteal elevation which allows the gingival tissues to heal more rapidly.
6. Avoid placing Healing Collars then having to come back and take separate Transfer Analog Impressions.
7. Create interdental papillae by compressing the tissue and creating crown with the proper mesiodistal width.

The problem of ridge lapping was said to have been eliminated with the most recent introduction of certain "anatomically correct" abutment systems. However, without first altering the width, taper and contour of the transmucosal cuff, ridge lapping cannot be entirely eliminated.

Another very important consideration is that of periosteal healing. Many suppliers of conventional systems endorse the use of a full thickness mucoperiosteal flap at the time of implant uncovery. No matter how conservative, the flap design studies have shown that elevating the periosteum results in a risk of necrosis and slow remodeling of the cortical plate which, if incomplete at the time of second stage surgery, will load necrotic or immature bone resulting in excessive cortical crater formation. With this in mind it becomes obvious that if periosteal elevation can be avoided then it should be avoided. The solution is to use a Custom Tapered Transmucosal Gingivectomy procedure which does not require a flap approach. When this procedure is combined with a Modified Impression Coping, a Locking Healing Collar and a UAS or MUAS, the combined technology provides for optimum aesthetics and function.

Finally, the flexibility of this system is perhaps best illustrated by the incorporation of Flexible MIC's and MIA's. These components allow the clinician to correct for off angle implants and to deal with waxing to the UAS core regardless of the peri implant transmucosal taper. The following is a summary of the steps of the tapered gingivectomy procedure according to the present invention:

1. Using preliminary wax up teeth to set tooth position for missing teeth, create a surgical template using model #1.
2. The surgical template aids the dentist in placing the implants. This template is saved during the 4–6 month healing period.
3. Before implant uncovery, an impression of the mouth is taken. A second stone model is created and accurate full gingival contour diagnostic wax ups are created on this model. Using the initial surgical template to indicate implant position, outline these accurate full anatomical contours on stone Model #2 with a black line.
4. On Model #2 create a redline 1.0–1.5 mm inside these outlines.
5. Make a clear template on Model #2 ("Gingivectomy Template").
6. Trace the red outline markings onto the Gingivectomy Template.
7. Remove the template from Model #2 and using a bur, slowly enlarge the holes up to the red lines, exposing the red lines on the model.
8. Before replacing template on Model #2, create depth cuts in the model to replicate approximate depth of soft tissue coverage (measured by probe).
9. Replace the Gingivectomy Template on Model #2.
10. Angle bur and enlarge the template until red lines on model disappear. This is done to a predetermined depth (depth cut). Enlarging the model creates a flare on the Gingivectomy Template.
11. Place surgical template from model #1 in mouth and place a dot where the implant center should be.
12. Remove surgical template and place Gingivectomy Template in the patient's mouth. Check to see that implant dots line up with holes.
13. With the Gingivectomy Template in the mouth, start removing gingival mucosal tissue. Using a tissue punch, remove a plug of tissue and expose the implant.
14. Between the border of the tissue punch hole and the Gingivectomy Template there will still be excess tissue. Using a bur, scalpel, Nd: YAG or $CO_2$ laser, remove this tissue to form a taper from the annulus of the implant to the perimeter of the Gingivectomy Template creating an anatomically tapered gingival cuff, of specific individual dimension and contour.
15. Place modified implant copings or Flexible MIC's onto implants and syringe impression material into the tapered transmucosal sulcus. After material has set, remove impression copings. This will transfer to master model #3: (a) the tapered cuffs; and (b) the axial and rotational position of the implants.
16. Insert modified implant analogs onto the modified implant copings, and cast stone model #3. Threaded base 10s are screwed into mouth and a light activated periodontal wound dressing is syringed around them to hold tissue contours and promote healing (Barricaid).
17. This stone model which contains modified implant analogs and shows the actual tapered gingival cuffs as they appear in the mouth is master model #3. A second model is created from the same impression using a new set of modified implant analogs. However, this model is created with a G.I. mask. This model #4 is used to replicate the resiliency of the tissue in the mouth and is not lab altered.

18. Lab altering requires the tapered Gingivectomy Template to be expanded with a bur to the original black line which represents full anatomical contour.

19. Place the Tapered Gingivectomy Template after it has been so altered, on master model #3, and using gingival burs, carefully enlarge the taper on the model to the enlarged outline of the altered. gingival template. This causes the healing collars to be formed slightly larger than the taper in the mouth and creates firm, but not excessive, pressure against the tissue.

20. Place locking healing collars into the lab altered model #3 and:

(a) Add wax around the metal base and plastic sleeve up level to the gingival crest;

(b) Use hot wax casting techniques to create a cast locking healing collar with a fully customized anatomically contoured taper;

(c) Create a temporary crown on the locking healing collar;

(d) Return locking healing collar to mouth and secure after removal of wound dressing (Barricaid) and threaded bases (installed in step 16).

21. Before the final abutment is fabricated, the tissue is allowed to heal, which requires that the implant/bone interface is slowly and progressively bone loaded over a period of months. This is controlled by modifying the temporary crown.

22. Once the tissue has healed, master model #3 requires one further modification. The occlusal-gingival height of the stone model #3 is shaved down slightly to compensate for any tissue recession and to hide the margin of the crown. Master model #3 is now referred to as "Final Lab Altered Model #3."

23. Using final lab altered model #3, fabricate a UAS or MUAS. If the prosthesis is not removable, then all these abutments incorporate the customized anatomically correct tapered gingival cuff.

24. Once the abutment has been fabricated, model #4 is used to create proper margin position and contour for the overlying prosthesis, ie. crown.

Section V: The Milled Universal Abutment System (MUAS): Breaking New Ground With CAD/CAM.

Part 1: Introduction.

"Of all the new technologies available to dentists, none is more likely to drastically change the practice of dentistry in the 21st century than the Dental CAD/CAM."

Francis Duret, May/93 CDA Journal

At one end of the dental spectrum are dental implant companies using very elaborate CNC drilling machines and sophisticated CAD software to create very precisely machined prefabricated implant components. However, their biggest limitation is that these standardized prefabricated components are all exactly the same. These systems cannot produce individually customized components [e.g., conventional angled titanium abutments ("ATA's")].

At the opposite end of this spectrum is the dental CAD/CAM technology that digitizes information from the individual patient's mouth using optical scanning to create a customized restoration for the individual patient. Its limitations are (1) its accuracy 80–100 microns and (2) the fact that the dental CAD/CAM system is used only to create crowns, inlays, onlays, area veneers and in more select instances, bridges. The use of material is also basically limited to ceramics. P-R Lin, B. P. Isenberg and K. F. Leinfelder, *Evaluating CAD-CAM Generated Ceramic Veneers,* 124 J.A.D.A. 59–63 (April 1993); F. Duret, *The Practical Dental CAD/CAM in* 1993, 59 CDA J. 445–51 (No. 5, May, 1993); Siemens Medical Engineering Group Dental Sector, CEREC Computer Reconstruction, CEREC Pamphlet.

It is evident that each technology has limitations, which is perhaps why to date no one has applied this CAD/CAM more completely in the implant field. Perhaps the closest that any one company has come is the Procera system which can, using a combination of external surface milling and internal electroerosion, produce titanium crown and bridge frameworks (for ceramic coating). Unfortunately, this is the extent of its implant involvement.

In order to apply CAD/CAM technology more completely in the implant industry and fabricate customized implant abutments, a combination of technologies is required—a blend of CNC milling and customized CAD/CAM capabilities. The result is a breakthrough technology which the present invention accomplishes by allowing implant abutments to have all of their exacting threads and interlocks pre-machined into a titanium block using a CNC milling machine or similar device and then having that abutment's customized external contours milled into that titanium block using Dental CAD/CAM that has in the past been reserved for ceramics and creating custom fillings. The result is a very precise fitting, completely customized abutment, for use in the Millable Universal Abutment System, and which takes the place of the core and cast abutment in the UAS.

Part 2: Description of the MUAS.

This unique new combination of technologies creates an unparalleled potential for the entire implant industry because a totally customized implant abutment can be created not only by a wax added and casting technique (in the UAS) but now by means of a CAD/CAM system (the MUAS). Both methods have the same anti-screw loosening capability as well as many other solutions to common abutment problems.

The titanium blank 66, shown in FIGS. 12–16, which may be milled by the CAD/CAM System, is unique in that a CNC or comparable milling machine has been used to pre-machine a core thread 70, the core projection 32 and an anti-rotational mechanism 24 thread or similar anti-rotational means directly into the titanium blank 66. In other words, it looks almost identical to the UAS core 18. As disclosed further below, modifications can also be made to the titanium blank 66 in order to incorporate the design concept of the resilient core 44 into the MUAS.

It is important to remember that these premachined titanium blanks 66 fit precisely to the base 10 because these components have been CNC milled together in order to align the anti rotational mechanism 24 thread hole and notch 40 correctly. Whether the base 10 has an external or internal machined interlock 14 with the implant 16 also makes no difference to the fit of the base 10 and the titanium blank 66. In fact, the titanium blank 66 can be looked upon as a bulky oversized core 18 and the bulk of the titanium above the threaded section is for practical purposes a mass of metal that can be milled to any customized angle or shape using a dental CAD/CAM.

This procedure is achieved by using the Lab Altered Master Model #3, as described in Section IV. The Master Model #3, before it is altered, is an exact duplicate of the tapered gingivectomies and implant position in the mouth. The transmucosal cuff of this stone model surrounding the implant analogues may be altered using the gingivectomy lab burs. The rubber tips of these burs prevent damage to the implant analogs, but conventional or other burs may be used as well. The cuff is enlarged 1.0–1.5 mm so that the gingival tissue fits firmly around the crown and the abutment. The wax patterns that were originally used to make the Gingivectomy Template 50 can now be used to check and see if the transmucosal cuffs are at full anatomical contour. The gingival crests of these cuffs are also altered—in fact, they are ground down by about 1 mm to create subgingival margin placement for the crown. This can be verified later on Model #4, as was described in Section IV.

These lab altered steps are critical to the fit and shape of both the abutment 22 and the crown 26. When the abutment 22 is secured down to place in the mouth it will expand the surrounding gingiva just enough to provide a firm fitting gingival cuff. If too much tissue expansion is required, as is the case when a Tapered Gingivectomy is not performed, this can crush the tissue and deprive it of its blood supply, which can lead to gingival recession, gingival clefting and sloughing of the tissue.

This is why the lab altered Model #3 is preferably only altered by 1–1.5 mm and why a Tapered Gingivectomy is performed in the first place.

Figure 17:
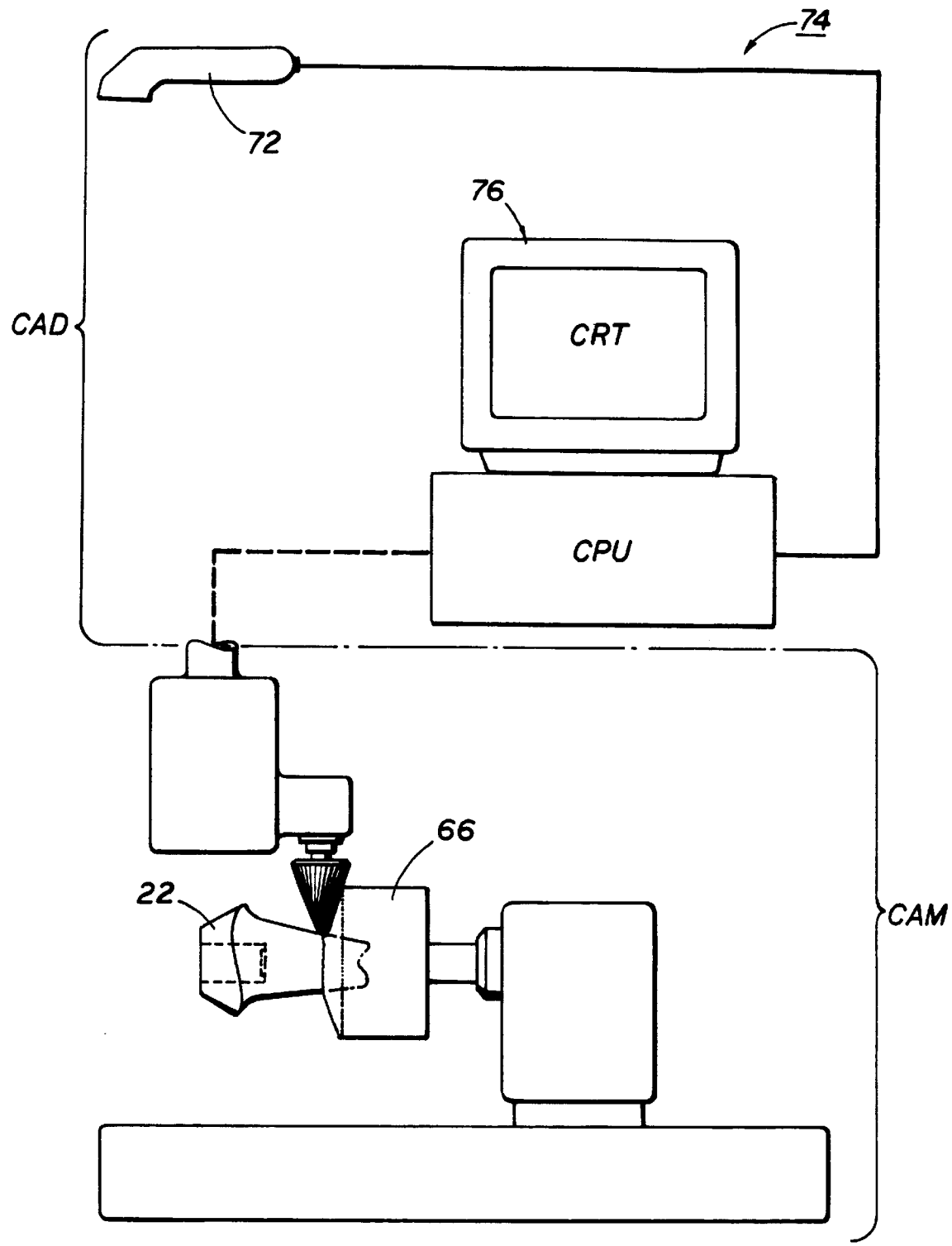
FIG. 17 is a schematic block diagram of a CAD/CAM system which may be employed to design and prepare a MUAS.

Next comes the optical impression of the lab altered Master Model #3. This optical impression generates a digitized image of the tapered cuff 54 as well as the implant 16's axial and rotational positions, using CCD-based sensor 72 or other appropriate (and conventional, if desired) imaging components as shown schematically in FIG. 17. In order to transfer the axial and rotational positions of the implants accurately, the optical impression may taken with the threaded base 10 and an elongated fixation screw 20 securely in position. The base 10 is placed in such a way that the ALS notch 40 is accessible for the dentist. The optical scanner senses the position and disposition of the notch 40 and fixation screw 20 (which may be in cartesian, spherical or other reference system as desired) and the processor and storage means of the CAD/CAM device 74 processes and stores this information and aligns the titanium blank 66 accordingly in conventional fashion for appropriate angulation of the abutment 22 with respect to the implant 16, both rotationally and laterally. This is especially critical when more than one abutment 22 is being constructed as in the case of a bridge.

Digital information corresponding to the optical impression is stored for processing by the CAD program conventionally. This program is adapted in conventional fashion to recognize that the base 10 is in position and to compensate for this in the design of the abutment 22. The CAD program may be modified to allow the operator to design on-screen (via pen-based, mouse or keyboard input/output means 76) a custom shaped abutment 22, using an image manager (as shown schematically in FIG. 16) that allows for surface reconstruction and modelling. This CAD program may also be modified to design a recess or cavity 68 that can be milled out for a precision attachment 28 component corresponding to a corresponding component in the overlying crown 26. Since one cannot cast or solder to titanium, standard laboratory procedures are of no use, one may use resin bonding techniques according to the present invention for securing such attachments.

The milling or machining of the abutment is carried out in conventional fashion by a computer aided machine tool based on data from the optical impression and the clinician using the image manager. The result is a completely customized titanium implant abutment 22 which has been made using CAD/CAM technology in a new way. This titanium implant abutment 22 features the following advantages, among others:

(1) Is biocompatible with the surrounding tissue;
(2) Has not been cast, soldered or laser welded;
(3) Because of its physical properties, is totally inert and will even promote a hemidesmosomal attachment in the peri implant sulcus;
(4) Is stronger than any other 2 or more piece system;
(5) Is identical to the UAS system (with all attendant advantages) except that its abutment contour is computer generated and not wax added; and
(6) Can incorporate resin bonding of precision attachments which allows for new and innovative prosthetic designs.

Once the MUAS has been machined (and this also applies for the UAS), it can no longer be rotated to position on Master Model #3 due to its intentionally customized asymmetrical taper. This is why Soft Tissue Model #4 has been created in order to allow the abutment to be fully seated and the contours and marginal placement of the overlying crown fully visually and physically checked.

The last modification that has to be made to the abutment 22 before the crown 26 can be fabricated and adjustment is the insertion and adjustment of the screw 38 or 45 length. Because the thread of screw 38 or 45 and taper is of a standard measure in every titanium blank, a standard screw 38 or 45 can simply be inserted into the completed MUAS and cut back flush to the abutment wall.

Figure 13:
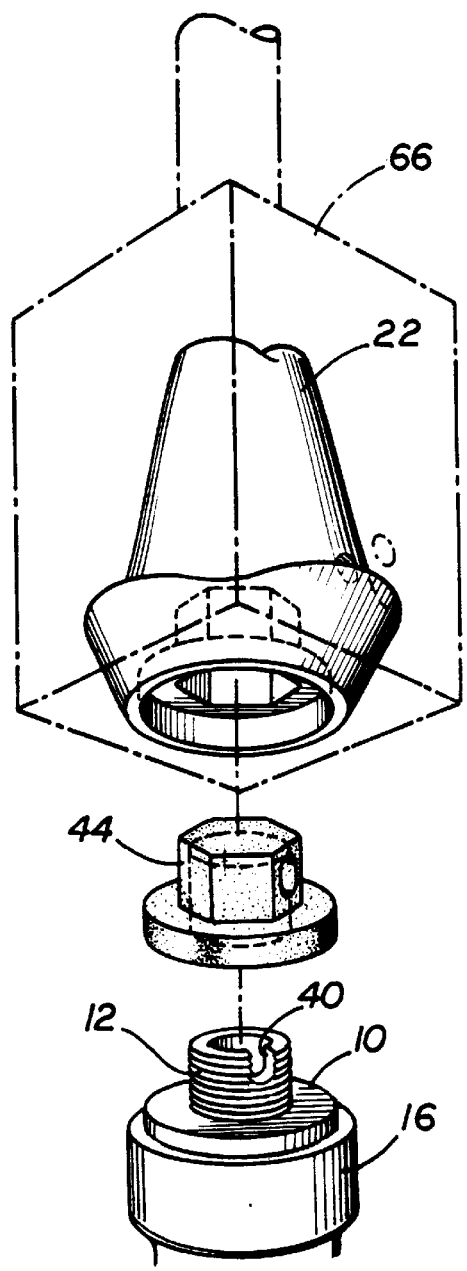
FIG. 13 is a perspective view of components of a MUAS which includes a resilient core.

With minor changes to the shape and design of the premachined titanium blank 66 this technology can be used to produce a MUAS, a modified MUAS using a resilient core 44 (as shown in FIG. 13), MUAS abutment 22 that will fit a variable height threaded base 10 and anti-rotational mechanisms 24.

As was described above, the MUAS variable height assembly portion of the base 10 may be made in different heights so that when the core 18 and anti-rotational mechanisms 24 are positioned they are located at the gingival crest. This can be accomplished by lengthening the base 10. These alterations also require construction of a modified titanium blank and a slightly longer fixation screw.

We know that the bases 10 can be milled or otherwise formed so that the threaded portion is adapted to different heights and widths. The blank 66 and the internal dimensions of the core 18 and its threaded portion also have to be altered accordingly. The outer diameter of the blank 66, however, does not have to be altered and neither does the milled base seat of the blank 66. This blank 66 can be milled down in the same manner as the regular blank 66; all that has to be done is to input the height of the specific variable height base into the CAD program and choose the appropriately machined blank 66. These same types of changes can also be made to accommodate a resilient core 44.

Now that it is possible to create a precise fitting totally customized implant abutment 22, it should be mentioned that the manufacture of corresponding crowns and bridgework/frameworks from titanium is possible using the Procera CAD/CAM unit or similar conventional devices and techniques. With the combination of these technologies it is now not only possible to manufacture precise fitting customized implant abutments 22 according to the present invention but also the crown 26 and bridgework to fit overtop.

Section VI: Universal Abutment Resin Bonding Systems.

This section addresses use of the Universal Abutment Resin Systems ("UARS") according to the present invention in conjunction with UAS/MUAS implant abutments 22 and intra abutment precision attachments 28.

The application of resin bonding technology in non implant related prosthodontic dentistry today is still very limited. Only a few companies such as Cendres and Metaux, Sui and a growing number of other companies are endorsing resin bonding, but even these applications are limited to joining attachments into fixed and removable portions of a denture (natural teeth). This is but a small portion of the potential new resin bonding marketplace.

The CM Spacer technique detailed by Cendres and Metaux has many advantages and can be used in conjunction with many different types of resin product but it has limited implant application.

The potential market for resin bonding implant application is huge by comparison and the UARS has a much broader application. The precision attachments' 28 component parts can now be resin bonded into either a MUAS or a UAS abutment using a series of new spacer techniques. It should be made very clear that, up until now there have been no existing implant abutment or resin systems created for intra abutment resin bonding of precision attachments in implant dentistry. The beauty of this technique is that crown and bridge prostheses can now be made patient removable, passive fitting, aesthetic, stable, hygienically accessible and if necessary can be ridge lapped without damaging the surrounding tissue and contributing to peri implantitis.

The UARS techniques can in fact be employed to join precision and semi precision attachment housings into both the abutment and the frame construction of the implant prosthesis because slide attachments require 2 components as shown in FIGS. 27–28: (1) a matrix component 78 which is usually housed within the contours of the abutment (intra abutment) 22 and (2) a patrix component 80 which is usually passively bonded to place on the internal aspect of the overlying prosthesis framework.

For purposes of comparison, at present one other resin bonding technique exists for implants, which is referred to as the Kulzer Abutment Luting Technique ("KAL"). R. C. Olarn, W. R. Lacefield, *The Passive Fitting Implant Prosthesis,* 4 The Implant Society 8–15 (No. 2, 1993). It is, however, used with conventional abutments that feature central bores, and it is used to join conventional UCLA type abutment cylinders to the main framework of the prosthesis in a non-patient removable fashion.

The KAL technique claims to achieve a more passive fitting prosthesis because a plastic cylinder (spacer) creates an enlarged hole in the frame which is taken up by the resin cement while everything is seated passively in the mouth. This system has obvious limitations and differences from the UARS technique, however:

(1) The KAL technique uses only a Kulzer Resin System—the UARS technique is compatible with all resin bonding systems.

(2) The KAL technique joins abutments and mainframes rigidly together with resin. The UARS technique allows the abutments and the mainframe to be separable (pulled apart via precision attachments).

(3) The KAL technique does not allow for patient removable prostheses—the UARS technique does.

(4) The UARS technique is employed to bond precision attachments within the normal contours of UAS or MUAS implant abutments. The KAL technique has no such applications.

(5) The KAL technique claims a passive fit between the prosthesis and the implant. However, once the prosthesis has been rigidly resin bonded to the abutment cylinders the fixation screws of these UCLA like abutments must be constantly torqued down over a period of a month in order to prevent the screws from backing out (which they can do anyway). A. Jaggers, A. M. Simons, S. E. Badr, *Abutment Selection For Anterior Single Tooth Replacement: A Clinical Report,* 69 J. Prosthetic Dentistry 133–35 (No. 2, Feb. 1993). "The main disadvantage of the UCLA System is the potential for loosening of the retaining screw." Furthermore, every time these fixation screws are tightened this creates pressure (preload) between the implant and the prosthesis. When this preload is superimposed by off axis occlusal loading forces the result can be a non-passive fit. In other words the KAL technique may start out as passive, but as soon as the resin sets and the fixation screws are retightened it has the potential to become non-passive. Of course the same concept works in reverse as the screws loosen and begin to back out—a non-passive fitting prosthesis.

With the UARS technique, because the abutment 22 is anti-screw loosening, the fixation screw 20 can be torqued down into place, retightened ten minutes later and then capped off and prevented from loosening by the core 18 and ALS 24. Now the abutment 22 is secure and the precision attachment 28 assembly can be passively bonded into position without being affected by the fixation screw 20. Therefore the precision attachment prosthesis starts out with a passive fit and remains passive.

As has already been pointed out, resin bonding is the only proven technique for the direct connection of precision attachments to titanium. Thus for the MUAS system there is no other option. However for the UAS system, the abutment can be cast to the ceramicor core in any alloy except titanium and therefore the attachment connection can be casted, soldered or even laser welded. Unfortunately all three of these options put the precision attachment under a great deal of temperature change which affects not only the physical properties of the attachment but also, with very thin female housings, creates potential for a potential strike-through of the wall by a hot melt. Furthermore, casting on can result in an incomplete metallic union between the frame and the attachment if the correct placement of the spaces and choice of the proper volume relations in the region of the attachment are not selected.

Although laser welding of attachments 28 shows great promise, resin bonding at the present time is still the preferred method. The UARS technique allows for the attachment component to be resin bonded to place without incorporating the problems associated with casting or soldering such as the stresses of temperature variation. There are other advantages to the UARS technique as well:

(1) It is more accurate in aligning the matrix and patrix components of the attachment in the mouth because it creates a truly passive fit rather than rigidly attaching the components in the lab. This option is available for resin bonding but not for casting, soldering or laser welding.

(2) If the matrix or patrix components must be changed, it is easier to remove the component out of resin than it is to break the casting or solder joint or laser weld. In fact, disconnection of the resin bonded interface may be achieved by blasting with 50μ Aluminum Oxide or similar material.

(3) The bond between the resin and the metal has been proven to be incredibly strong (6–8000 psi interfacial bond strength).

(4) The UARS technique helps eliminate many unnecessary dental lab and clinical procedures such as casting, soldering and investing.

A box or cavity preparation 68 for the attachment 22 can be created in the abutment in a number of ways, all of which are compatible with the resin bonded technique. If an MUAS or modified MUAS is being created then the cavity 68 can be milled at the same time as the abutment contours. If a UAS or modified UAS is being created then the box or cavity preparation 68 can be created in at least one of three ways.

(1) The cavity 68 can be milled in after the abutment 22 is cast.

(2) A cavity 68 can be created in the wax abutment 21 and then cast, utilizing an I.N.S. spacer that exactly duplicates a portion of the precision attachment. This creates a precisely cast cavity into which the other interlocking half of the precision attachment component will fit.

(3) An oversized I.N.S. spacer or similar ceramic spacer can be incorporated into the wax abutment 21, which like number (2) above can be removed after casting with a 50μ or similar particle sandblaster. As more and more precision attachments 28 are incorporated into implant abutments the spacer techniques will grow in popularity, and so will the market for these ceramic spacers. For further details on this spacer technique see Section VII Part 3.

Once the cavity 68 has been formed within the implant abutment a duplication model is usually created. When such a model is used, analogs of the patrix and matrix components are set into the model rather than the precision attachments themselves. These analogs can be partially oversized replicas of the precision attachments which help to create and maintain extra space in the abutment and the framework, or they can be exact duplicates of the precision attachments. These analogs also prevent wear and tear on the attachments. See FIG. 30B. As will be seen below, they can also be used to help align the precision attachment components and for this reason the mechanically interlocking surfaces of the analogs are exact duplicates of the attachments. Only the external surfaces vary in size in certain situations to maintain the extra space for the resin bonding material.

If a duplicate model is not going to be used then the external surfaces of the matrix component 78 can be coated with a silane coupler or other desirable agent and set within the abutment 22's cavity 68 which is filled with resin. The attachment component 78 is held rigidly in its proper position with a parallelometer and the resin sets up around it. The excess resin is removed and the matrix 78 is left rigidly connected to the abutment 22.

The patrix component 80 which is usually housed in the internal aspect of the crown 26 or prosthesis framework can also be resin bonded into place either in the lab or preferably in the mouth using the same spacer concept and silane coupler application. In order for this resin to set properly, dual cure cements are preferred and therefore a slot or hole is created in the crown framework to allow the back end of the attachment (the flag) to extend through the frame and have the surrounding resin light activated.

The UARS technique can be used extensively in implant dentistry in combination with these new UAS and MUAS abutment systems because the philosophy, approach and implementation of this new technology is passive fitting precision attachment patient removable prosthetics.

Because of increasing numbers of implant supported prostheses being fabricated, the importance of resin-metal bonding is also likely to increase. With the resin bonding technology of the present invention, the market is not only going to increase, but also undergo a major shift as more and more prostheses start to incorporate precision attachment patient removable designs.

Section VII: Prosthesis Design: Expanding The Options.

Part 1: Introduction.

Up until now prosthesis design has provided the clinician only limited options, with either fixed or removable appliances, i.e. Misch's classification. Recently an article entitled "The Use of Intra Coronal Attachments on Removable Prostheses" appeared in the International Journal of Oral Implantology, which described a ball and socket o-ring attachment for an overdenture. C. E. Misch, *The Use of Intra Coronal Attachments on Removable Prostheses,* Int'l J. of Oral Implantology. In the inventor's opinion, this is precisely why a new classification needs to be created to redefine the use of precision attachments and patient removable prostheses. The prosthetic designs according to the present invention not only reflect this new classification by providing intra abutment precision attachment patient removable crown and bridge appliances, but also new prosthetic designs for overdentures as well. The crown and bridge prostheses, for example, are just as stable, if not more stable, than the screw-retained protheses but also have the added advantages of being passive fitting and able to be ridge lapped due to the fact that they are patient removable. As discussed below, many of such new prosthetic designs, such as the new overdenture bars, are not possible with existing systems. Also detailed below is a new classification of prosthetic implant design based on these possibilities.

There are approximately 20 million people living in North America who are completely edentulous, and world wide percentages are probably even greater. A good percentage of these people have unsatisfactory lower dentures. A typical case would be where the upper teeth were removed along with the lower posterior teeth at an early age, leaving only the lower anterior teeth. These lowers were subsequently removed leaving an uneven edentulous ridge. In many instances this scenario leaves very little bone posteriorly (following Wolff's Law) but adequate bone between the mental foramina to support implants.

Implants have a high degree of predictability especially in the lower anterior region, which is the location that the inventor believes is admirably suited for this unique style of prosthesis.

Part 2: Existing Classification of Implant and Tissue Supported Overdentures.

A. Tissue Supported—Implant Retained Overdentures.

This classification usually involves only 2 implants which have a cap and ball like attachment screwed to the implants and which are predominantly located in the cuspid region. These attachments, which can also be magnetized, act to retain the denture—the majority of support and stability, however, comes from the tissue coverage of the denture base.

B. Tissue Bar Overdentures.

These types of dentures are both implant and tissue supported. They usually involve 4 implants and can be a combination of tissue bar and resilient ball and socket or o-ring attachments, which allow for added stressbreaking as the denture is displaced towards the ridge under occlusal loading forces. The Hader clips which are usually positioned on the anterior aspect of the tissue bar also rotate around the bar if it is oriented parallel to the axis of rotation. Even with 4 implants, distal cantilevering is not recommended without the incorporation of resilient attachments posteriorly into the tissue bar design.

These tissue bar overdentures allow for the denture to be removed by the patient which improves oral hygiene access, but cleaning around the bar does pose a hindrance for some patients and this can lead to plaque and calculus accumulation.

Because these dentures can be removed, a buccal and lingual flange can be placed for lip support, aesthetics and phonetic advantages. However, even with 4 implants these tissue bar overdentures are still not as stable as the fixed dentures, and the tissue bars still have problems with screw loosening, impassive fitting frameworks and lack of hygienic access.

C. Fixed/Detachable Denture Prostheses (The Hybrid Denture).

These appliances require a minimum of 5 or 6 implants if they are to be done as conventionally recommended, such as by Branemark. They provide for an extremely rigid prosthesis but because it is screw retained it is only detachable by the clinician. Furthermore, the use of an excessive vertical or horizontal cantilever with this type of a prosthesis can lead to screw loosening or fracture, bar fracture, implant fracture and/or de-integration. There is also the problem associated with framework distortion and non passive fit. This point becomes glaringly obvious upon examination of the results of Dr. Zarb and the University of Toronto's 1990 longitudinal implant study which were discussed in an article by Monteith:

> One noticeable feature among the problems and complications encountered during the Toronto study was the large number of gold screws that were reported to have fractured. Of 274 implants that were placed to support 49 prostheses, 53 fractures of the gold alloy screws were noted, 14 framework fractures and 9 abutment screw fractures. Similar observation emerged from a replication study conducted at the University of the Witwatersrand in which Shakelton et al. reached the conclusion that more than 50% of prosthetic problems are related to stress factors acting on the prostheses . . . To have screws fracturing as a normal event would not be conducive to sustained levels of patient confidence.

B. D. Monteith, *Minimizing Biomechanical Overload In Implant Prostheses: A Computerized Aid To Design*, 69 J. of Prosthetic Dentistry (No. 5, May, 1993). The ad modum Branemark fixtures are frequently cantilevered distally to engage an opposing molar occlusion, but English is quick to reveal that an excessive distal cantilever with inadequate anterior-posterior spread is a prelude to mechanical or osseous failure, or both.

The critical A-P Spread that English speaks of is fundamental to the design of existing implant/implant and tissue supported dentures. Unfortunately, surgical and anatomical restrictions often prevent a great deal of anterior-posterior separation between implant fixtures which decreases the A-P spread and limits the length of distal cantilever. English clearly points out that the A-P spread has a direct role on whether one is dealing with a class I or class II lever and that this is accentuated by the jaw relationship.

A patient who is a known clencher or bruxer imposes forces on the cantilever that are accentuated as one moves posteriorly, which varies considerably according to the maxillamandibular jaw relationship. These cantilever forces are extremely damaging to the implants, for as English again points out "when one places occlusal load on a cantilever segment the two most distal implants in the fulcrum are placed in compression in a vertical download, and the implants anterior to the fulcrum are placed in tension, i.e. a vertical pull out." C. E. English, *The Critical A-P Spread*, 1 The Implant Society 2–3 (No. 1 1990). Furthermore, Falk et al., have established "that fully 70% of the occlusal forces are borne by the cantilevered units and only 30% of the occlusal load is borne by the anterior segment." H. Falk, L. Laurell, D. Lundgren, *Occlusal Force Pattern in Dentitions with Mandibular Implant-Supported Fixed Cantilever Prostheses Occluded with Complete Dentures*, 4 Int'l J. Oral Maxillofacial Implants 55–62 (No. 1, 1989). This study concluded that the recently reported higher number of failures for this type of treatment was probably the result of poor distribution of occlusal forces during mastication. C. E. English, supra. "The only way to counteract these lever forces would be to have the lower teeth extended anterior to the most anterior implant to provide a counterbalancing force." But, "unfortunately the advantage is still to the distal segment with increased occlusal forces". Id. In a patient with a class II skeletal jaw relationship, this is possible because the denture teeth need to be extended anteriorly for lip support and improved aesthetics. Unfortunately for most other cases this can spell potential overload and implant failure.

Furthermore, because the ad modum denture is fixed into place, the abutment cylinders must be left exposed for oral hygiene access. In other words, no buccal or lingual flange can be created, which often creates aesthetic and phonetic problems as well as lack of lip support.

D. The Spark Erosion Implant Supported Denture.

This type of denture was created to: (1) solve the problem of the fixed denture that the patient could not remove; (2) provide a buccal flange for better aesthetics, phonetics and lip support and (3) solve the problem of passive fit. This type of denture is created to fit over a specially constructed tissue bar (using spark erosion technology) that has an external 2° taper to engage with a friction fit a milled bar that is buried in the underside of the denture. The spark erosion denture is as stable as the screw retained fixed denture but has the added benefit of being partially removable by the patient. However, these spark erosion dentures must still use a rigid cantilever design and the patient still has to clean around a fixed tissue bar. Furthermore, the abutments that the tissue bar is anchored to still suffer the same problems with component fracture and screw loosening.

Part 3: The Precision Attachment Stress Broken Denture: An Alternative to existing Fixed/ Detachable Dentures and Bar Overdentures using UAS/MUAS Assemblies. Abstract.

Stress Broken Precision Attachment Dentures of the present invention ("SPADs"), unlike the above appliances, can be removed as one piece by the patient exposing easy to clean individual abutments. The SPAD is as stable as the fixed screw retained implant supported denture but it does not have the problems of screw loosening, impassive fit, hygiene access, cantilevered forces and framework distortion due to rotational displacement that these other systems have. SPADs feature many unique features, one of which is the way their hinged precision attachments are incorporated into the fixture design so that the prosthesis functions to absorb excessive vertical- oblique- and lateral-occlusal loads.

The Precision Attachment Stress Broken Denture.

The SPAD is a combination of both implant supported and tissue borne denture systems. It offers the same rigidity and stability that the implant supported denture offers and is also precision attachment patient removable. Furthermore, it offers superior hygiene access to the peri implant sulcus, and it prevents the screw loosening that plagues all the other implant prostheses as well as solving the problem of passive fit and retrograde peri implantitis by incorporating stress broken precision attachments into the framework design.

Computer analysis has shown that the stress levels within supporting bone imposed by axial and lateral loads applied to dental implants may be as much as 2–2½ times greater than the stress levels created simply by axial loading. Thus it appears that dental implants are particularly sensitive to lateral loads and that lateral loading on implants as a result of non passive fitting frameworks may cause screw loosening, component failure and bone resorption around dental implants. Therefore lateral loading should be avoided when at all possible. Unfortunately this is not possible with the existing technology. However, it is possible to absorb some of these lateral forces with the SPAD.

Perhaps one of the most exciting features of the SPAD is that all of these problems can be corrected utilizing only four implants. This is once again possible because of the dentures' superior stressbreaking capabilities.

The following hypothetical case illustrates one way a SPAD may be utilized according to the present invention. UAS or MUAS assemblies are placed on the master model and, in the case of a UAS, the UAS core wax ups are paralleled. Cavities are then created in the wax patterns for three newly designed Vertex intra abutment slide attachments according to the present invention, which are discussed below. (Obviously, other types of precision attachments could be used.) These cavities may be created using one of two INS spacer techniques. Both methods require that the margins of the four UAS assemblies are located at the tissue level on the model leaving the ALS mechanisms 34 or 35 exposed on the walls of the abutments.

The first method allows for only one half of the Vertex attachment to be resin bonded to place, usually the patrix component. To accomplish this an INS ceramic spacer is placed into the wax abutment but its external and internal dimensions are exactly the same as a matrix component. After the abutment has been cast this INS matrix spacer is sandblasted out creating an exact cavity into which a patrix attachment can later be anchored. A duplicate model can then be created by inserting patrix analogs into the matrix cavities. From this step forward both methods are identical.

The second method allows both halves of the Vertex attachment to be resin bonded to place. To accomplish this a matrix INS ceramic spacer is also placed into the wax abutment but its external dimensions are oversized to compensate and make allowances for the silane coupler and resin bonding material. After this INS spacer has been sandblasted out, a similarly dimensioned matrix analog can be inserted into the cavity. This will later be replaced by an actual matrix component that will be smaller and can readily be bonded into a passive position. Similar to method one, a duplicate model can be created by inserting a patrix analog, except this time the patrix analog is inserted into a matrix analog and not a precisely cast cavity.

In both methods these patrix analogs have external oversized dimensions, but their internal mechanically interlocking surfaces are exact replicas of the actual attachments. This allows the matrix analog to fit precisely to a patrix attachment component. Analogs are used to prevent wear and tear on the components and do not have to be retrieved from the duplicate models. They are usually made of brass and are inexpensive and can be discarded.

On the duplicate model a wax framework is then created overtop of the four abutments and around the oversized patrix analogs. Before it is cast, cavities are also created using INS spacers in the outside distal aspects of the frame to house two more patrix analogs. These two analogs are replicas of the two UARS stressbreaking attachments. The wax frame is then cast in titanium. As mentioned earlier with method two, when the INS spacers are sandblasted out, enough space is left in the framework for the attachments, the silane coupler layers and the resin, and the matrix and patrix analogs can be inserted to take the place of the attachment components.

The titanium frame is created with a double die spacer technique and is tied in and adjusted until it slides effortlessly to seat. At this point one could turn the model upside down and the framework would drop off. Remember that it is the attachments that create the retention and the stability for the prosthesis rather than the framework. The framework's function is simply to transmit and redistribute occlusal loads according to the present invention.

Passive fitting frames play a very important part in the prosthetic reconstruction phase of treatment but because precision slide attachments can now be used within the framework and the abutments, the concept of "passive fit" must evolve to include UARS technology. If precision attachments are rigidly connected before the framework is seated in the patient's mouth and they are not perfectly aligned, they will not fully seat, which in turn creates a non passive connection even though the framework may be fitting passively. Therefore, it is important to remember that when seating a precision attachment framework intraorally, it should slide passively all the way into place and either the matrix or the patrix of each attachment should have some "play" between it and the surrounding metal so that attachment can be fixed into a totally passive position. This space or "play" is created creating one of the two INS ceramic spacer techniques.

Using method one, the matrix has already been cast as negative relief by the INS spacer so that "play" exists between the patrix and internal aspect of the framework. This extra space or play allows the vertex patrix to be resin bonded permanently to place. This is achieved in the mouth by first placing the UAS to place and inserting the vertex patrices into the matrix cavities. After all the components have been silane coupled, resin cement is applied to the internal aspect of the framework (one at a time) and the framework is fully seated into the patient's mouth. The holes in the top of the framework allow for the overflow of resin cement and in the case of the vertex attachment, also leave the occlusal spreader screw exposed so that retention can later be adjusted. The cement is allowed to harden around the patrix. This resin bonding technique is repeated for all the attachments. To prevent excess cement from sticking to the UAS, a separating solution such as a surgical grade lubricant is used. Using method one the precision attachment prosthesis is now patient removable and completely passive fitting.

Using method two, both matrix and patrix components are resin bonded. First this requires that the patrix attachments are paralleled and then permanently resin bonded to place. This can be done in the lab by placing the vertex patrices into the matrix analogs on the duplicate model. They are now paralleled and the framework can be slid down overtop of the abutments with resin on both the attachment and the framework. The holes in the top of the framework allow for the overflow of resin cement and also leave the occlusal spreader screw of the vertex attachment exposed so that its retention can be adjusted.

The framework can now be taken to the patient's mouth along with the UAS's where the matrices can then be inserted into the permanently bonded patrices, located on the internal aspect of the titanium framework.

The hollowed out cavity on the UAS created by the INS ceramic spacer and then held by the oversized matrix analog can now be silane coupled. The space or "play" now exists between the matrix housing and the UAS cavity. The resin cement is applied to each cavity separately and the framework is fully seated. Once again the separating solution comes in handy, preventing the framework from bonding to the abutment. Once the cement has set the female housings are permanently resin bonded into their passive position. This method allows for more control over the attachments' final position and allows for easier retrievability of the attachments in case of breakage. However, this method involves an extra step. This method like method one also makes for a precision attachment patient removable prosthesis.

Using either method, once the two halves of the precision attachment framework have been bonded together in the mouth, the framework and the abutments can be returned to the lab where the two patrix housings of the UARS stressbreaking attachments can be paralleled and permanently bonded to the back ends of the framework. The two matrix housings are then either cast using a ceramic spacer or resin bonded into the framework and two unilateral partial denture frameworks are then created around them. (Once again, duplicate models can be created but this requires matrix and patrix analogs.) It is not until the acrylic is built up on these frameworks that the two matrix housings can be rigidly anchored. The design of the two UARS stressbreaking attachments allows denture teeth to be set over top of them and totally cover the matrix housings. Because the UARS patrix components are usually inserted into the distal side wall of the framework and porcelain covers this framework, they are not obvious. In other words, by the time the SPAD is complete the UARS stressbreaking attachments cannot be seen, for they are totally encased. The prosthesis is in effect a one piece assembly that has two stressbreaking hinged attachments incorporated into its design. There is no lingual bar connecting the two saddle areas.

It is important to note that the only position of the titanium frame that is rigidly cantilevered is the guide rail of the UARS stressbreaking patrix component, which unlike the ad modum Branemark frameworks that are rigidly cantilevered up to 15 or 20 mm.

Section VIII discloses how the UARS stressbreaking attachment components are constructed to resist heavy occlusal forces. The vertical translation and rotational ability of these UARS stressbreaking attachments is what helps distribute the applied occlusal forces, especially the damaging lateral forces. Without the resilient UARS stressbreaking attachments, there is no way truly to control these occlusal forces. Dr. Y. M. Ismail, a noted specialist in the field of implant occlusion and biomechanics has stated that these occlusal forces and resultant stresses can be controlled:

before the selection and placement of implants, prosthodontic diagnosis and treatment planning must be completed in order to properly evaluate and accommodate the direction, magnitude and duration of applied occlusal forces. It is imperative that in the final prosthesis every attempt be made to minimize lateral occlusal forces and their transmitted stresses to the supporting osseous structures. This can be accomplished by reducing the buccolingual width of the occlusal table, reducing the cusp height and angle, eliminating centric and eccentric interferences and customizing these occlusal concepts to the individual case.

Interview with Dr. Y. M. Ismail on Implant Biomechanics, 4 Dental Implantology Update 6–8 (No. 1, Jan. 1993). Although it is important to "customize the occlusion," it is the inventor's opinion that this by itself is not enough. The full arch hybrid fixed/detachable prosthesis must be modified dramatically to incorporate stressbreaking mechanisms such as the UARS stressbreaking attachments effectively to address the off vertical torquing and bending moments and the mesial implant stress concentration that occur as the result of the rigid cantilevered design.

Admittedly, the A-P spread is a vertical design factor in determining the length of cantilever. However, it no longer has as much relevance since all rigid cantilevers in full arch situations beyond 5 mm should be replaced with stress broken attachment assemblies.

There is also one other way of dealing with occlusal loading forces, that Ismail does not mention, and that is by modifying the actual abutments. This can be done by inserting resilient cores 44. This gives the clinician added flexibility in the design of the prosthesis. Resilient cores can be used in conjunction with precision attachments in situations where there is heavy occlusal loading (i.e., bruxism, clenching etc.) or when the clinician wants to "bone load" the prosthesis more carefully.

Conclusion.

The development of the spark erosion denture was considered to be an important step towards creating the ideal implant supported denture prosthesis. It was machined with exacting tolerances and was patient removable. However, it did not adequately address the problem of cost, passive fit, screw loosening, hygiene access and excessive cantilever forces.

The SPAD has not only addressed these issues, but at the same time it has also provided superior esthetics, phonetics, and function.

In a very recent article of the International Journal of Prosthodontics the 3 dimensional analyses of one piece implant supported prostheses was analyzed. In this article, multiple references were made to frequent framework fracture and how changes in framework designs have "led to an increase in cross-sectional areas at the junction of the cantilevered regions." K. B. Tan, J. E. Rubenstein, J. I. Nicholls, R. A. Yuodelis, *Three Dimensional Analysis of the Casting Accuracy of One-Piece Osseointegrated Implant Retained Prostheses*, 6 Int'l J. of Prosthodontics 346–63 (No. 4, 1993). In fact this article stated that "All authors concur . . . that bulk is needed occlusogingivally in the section distal to the distal most abutment to provide the required strength for support of the cantilever sections".

It is the inventor's opinion that the fundamental design of the ad modum Branemark cantilevered frame is outdated. The Zarb study reinforces this point due to the large number of component failures it cites. B. D. Monteith, *Minimizing Biomechanical Overload In Implant Prostheses: A Computerized Aid To Design*, 69 J. of Prosthetic Dentistry (No. 5, May 1993). These framework designs need to be reworked because some of the most well respected implantologists such as Jemt, Worthington, Skalak, Carlsson, Jones, Sullivan, and Zarb, all agree that the "inherent distortions in the existing prosthesis are a possible cause of component failure". Id. The SPAD, on the other hand is not cantilevered. Furthermore, the fact that the framework is smaller and that it is not screw retained, means that there is less bulk and less stress in the system, which translates into less risk of framework distortion.

Tan et al. describe this phenomena by stating, "Potential distortion of implant frameworks may be complex and may be magnified by both the relatively large mass of alloy cast and the configuration of the prosthetic framework." K. B. Tan, et al., supra.

Another fundamental design flaw that these authors point out is the potential vertical gap and bending moment created between the framework and the abutment cylinders as the result of screw tightening. This rotational displacement creates pre stress in the system which makes the prosthesis more prone to failure especially by long term fatigue.

Other design limitations of these cantilevered frames include screw loosening, and screw fracture—problems that have already been mentioned.

The SPAD on the other hand does not have these design limitations.

The following is a brief review of what makes SPAD so unique:

1. It uses resin bonding technology and intra abutment precision slide attachments to solve the problem of passive fit and patient removability.

2. Due to the unique design of the UAS and MUAS abutments, the SPAD has an anti-screw loosening capability.

3. The stressbreaking attachments that are housed in the framework and the denture saddles provide for a more even distribution of occlusal forces and stressbreaking.

4. Because the framework is not held to the abutments by screws there is limited rotational displacement or pre stress tendency in the system.

5. The stress broken extensions, in a bilateral situation, have no lingual bar and are removed as a single component along with the rest of the prosthesis.

6. The entire prosthesis is patient removable which leaves only the individual abutments to clean around and no connecting tissue bar.

7. The retention of the prosthesis is adjustable.

8. Both the abutments and the framework can be made in Titanium and are therefore totally biocompatible.

9. It uses a minimum number of components and only 4 implants.

10. The abutments can be fabricated using CAD/CAM technology.

11. Modified resilient core assemblies can be used during progressive bone loading or to help cushion heavy occlusal forces in a bruxer or clencher.

Part 4: Patient Removable Intra Abutment Precision Attachment Crown and Bridge Assemblies for the Edentulous and Partially Edentulous Patient.

Abstract.

Intra abutment precision slide attachment crown and bridge assemblies have many advantages over the existing prosthetic appliances. In situations where only minimum cantilevers are required due to adequate implant placement, these new prostheses offer better aesthetics and more comfort and stability than the removable metal/acrylic denture systems. Perhaps the biggest advantage that these systems have over the screw or cementable crown and bridge appliances is daily patient removability, which creates better periodontal maintenance and more leeway to overcontour ridge laps and over-extend the porcelain and metal. This ability helps compensate for problems associated with ridge resorption, implant angulation and lack of interdental papillae, problems for which existing technology and prosthetic designs have limited solutions.

Even with all the advantages that these precision attachment assembly offer, without UAS or MUAS abutments of the present invention, the problems of passive fit and screw loosening cannot be solved, and the precision attachments cannot be mounted within normal abutment contours even with telescopic copings.

The solutions to these problems will also be detailed below during the discussion of patient removable intra abutment precision attachment prostheses using abutments of the present invention. An intra abutment precision attachment alternative using abutments of the present invention is also disclosed for a partially edentulous situation to help illustrate the flexibility of this prosthetic concept.

Introduction.

The following discloses a technique that almost completely eliminates the risk of peri implantitis (except that, perhaps, caused by occlusal overloading) in a patient who has undergone the complete restoration of the maxillary arch with six implants using standard abutments and a unique patient removable crown and bridge prosthesis. This prosthesis will later be compared to a model according to the present invention.

The screw retained implant bridge is considered by many to be the quintessence of full arch implant supported restorations. However, in the inventor's opinion, the screw retained fixed bridge has severe limitations because, among other things, it cannot be removed by the patient and therefore the peri implant tissues cannot be readily cleaned. U. Grunder, J. R. Strub, *Implant-Supported Suprastructure Design*, 10 Int'l J. of Periodontics and Restorative Dentistry 18–38 (No. 1, 1990); D. E. Tolman, W. R. Laney, *Tissue-Integrated Prosthesis Complications*, 7 Int'l J. of Oral and Maxillofacial Implants 477–84 (No. 4, 1992); R. B. Johns, et al., *A Multicenter Study of Overdentures Supported by Branemark Implants;* R. P. Desjardens, *Prosthesis Design for Osseointegrated Implants in the Edentulous Maxilla*, 7 Int'l J. of Oral and Maxillofacial Implants 311–20 (No. 3, 1992); B. Langer, D. Y. Sullivan, *Osseointegration: Its Impact on the Interrelationship of Periodontics and Restorative Dentistry: Part II;* 9 Int'l J. of Periodontics and Restorative Dentistry 165–83 (No. 3, 1989); G. J. Chiche, et al., *Adapting Fixed Prosthodontics Principles to Screw-Retained Restorations*, 2 Int'l J. of Prosthodontics 317–412 (No. 4, 1989); G. J. Chiche, A. Pinault, *Consideration for Fabrication of Implant Supported Posterior Restorations*, 4 Int'l J. of Prosthodontics 37–44 (No. 1, 1991); R. M. Watson, D. M. Davis, G. H. Forman, T. Coward, *Consideration in Design and Fabrication of Maxillary Implant Supported Prostheses*, 4 Int'l J. of Prosthodontics 232–39 (No. 3, 1991); K. B. Tan, J. E. Rubenstein, J. I. Nicholls, R. A. Yuodelis, *Three-Dimensional Analysis of the Casting Accuracy of One Piece, Osseointegrated Implant-Retained Prostheses*, 6 Int'l J. of Prosthodontics 346–63 (No. 4, 1993); M. Perel, *Retrievability and Screw-Hole Access*, 4 Dental Implantology Update 55 (FIG. 9), 60 (FIGS. 5–10) (No. 8, 1993); M. Perel, *Interview with Y. M. Ismail: Occlusion and Biomechanics in Implant Dentistry*, 4 Dental Implantology Update 6–8 (No. 1, 1993); G. J. Christensen, *Implant Prosthodontics Contribute to Restorative Dentistry*, 121 J.A.D.A. 340–50 (Sep. 1990); A. Fenton, *The Role of*

*Dental Implants in the Future,* 123 J.A.D.A. 37–42 (Jan. 1992); D. A. Gorber, *Implants—The Name of the Game Is Still Maintenance,* 12 Compendium Contin. Educ. Dent. 876–86 (No. 12); B. Langer, *Dental Implants Used For Periodontal Patients,* 121 J.A.D.A. 505–08 (Oct. 1990); B. D. Monteith, *Minimizing Biomechanical Overload in Implant Prosthesis: A Computerized Aid To Design,* 69 J. of Prosthetic Dentistry 495–502 (No. 5, 1993); I. Ericsson, U. Lekholm, P. I. Branemark, J. Lindhe, P. O. Glanty, S. Nyman, *A Clinical Evaluation of Fixed Bridge Restoration Supported by the Combination of Teeth and Osseointegrated Titanium Implants,* 13 J. Clin. Periodontal 307–12 (1986).

When gingival skirts and overextended porcelain are used to correct aesthetic shortcomings, the patient's ability to keep the peri implant sulcus clean is severely hindered. This leads to inadequate periodontal maintenance and is perhaps the leading cause of peri implantitis. Moreover, if these methods (gingival skirts and overextended porcelain) are not employed, the result is often enlarged embrasure spaces, gaps, improperly placed cervical margins and inadequate lip support. This often creates a less than adequate aesthetic look. Additionally, the screw retained prosthesis is subject to elastic deformation of the screws which permits openings to appear between the abutments and the framework. This creates a potential shift in leverage forces and a non passive fit which ultimately creates a stress on the implant-bone interface. B. D. Monteith, *Minimizing Biomechanical Overload In Implant Prostheses: A Computerized Aid To Design,* 69 J. of Prosthetic Dentistry (No. 5, May, 1993).

The solution to this involves a crown and bridge system which is neither anchored to the abutments by cement nor by screws but rather by a removable precision attachment assembly. This assembly not only makes it easier to clean than the cement or screw retained bridgework, but also more aesthetic and more versatile since it can be ridge lapped. Furthermore, it can be designed to be removable without any occlusal screws or access bores, which means that there is no risk of screw fracture with the precision attachment assembly.

Problems with the Edentulous Ridge (Maxillary).

Clinicians routinely see patients who wear a complete upper denture and have only their lower anterior teeth. This is a very common situation which often creates a Pseudo Class III occlusion. Clinically this in turn creates a need to angle the implants at a very steep incline to the occlusal plane, often out of alignment with other implants. This factor in conjunction with the buccal plate resorption pattern of the maxillary ridge creates some very challenging clinical situations. Bony defects and thin narrow ridges further complicate full arch implant treatment. Later on the inventor will detail how blade implants can be modified to accept MUAS and UAS (see Section X). Blade implants are used in situations where there are thin, narrow ridges and not enough surrounding bone for root form implants.

To compensate for facial ridge resorption in the edentulous jaw the clinician frequently must overcontour the prosthesis to maintain the correct lip and soft tissue profile. This overcontouring makes cleansing of the peri implant sulcus extremely difficult. Although this sort of situation is usually a very good indication for an overdenture with a flange, it is sometimes difficult to cleanse around the tissue bar. The tissue bar itself can also cause problems with a bulky palate if it is raised off the tissue, and always has the potential problem of screw loosening. The obvious solution to these problems is to design a patient removable prosthesis with individual abutments to give the patient maximum comfort and access. Given the choice between a crown and bridge prosthesis and a denture, most patients would prefer the natural feel of the crown and bridgework. In situations where finances are the limiting factor, fewer implants and an overdenture system is a viable option. However, the tissue bars must be redesigned to deal with the problems of screw loosening and passive fit (see this section Part 6 (Overdenture Applications)).

The Disadvantages of Screw Retained Implant Supported Bridgework.

Keeping the screw retained bridgework clean and plaque free is problematic. M. L. Perel, *Interview With H. I. Bader: How To Motivate. Inform Dental Implant Patients On Home Care,* 4 Dental Implantology Update 57–60 (No. 7, 1993). These appliances are designed either with (1) a ridge lap configuration, (2) open embrasures or less frequently as (3) a high water design. All these designs have limitations: The high water design, for example, where none of the appliance touches the tissue except the abutment sleeves, causes problems with speech articulation and phonetics (especially fricative and sibilant sounds) as air passes readily under the appliance. Aesthetically, this space is not very appealing. There is also the problem of patient comfort. For the patient, a space between the tissue and the appliance is annoying to the tongue. Even if the patient can endure all these problems, the fixed high water design still does not allow the patient to readily clean around the abutments. The UCLA style bridge with open embrasures shares similar problems. Even though the tapers for the crowns start just above the neck of the implants the tissue cannot be expanded to create normal soft tissue contours which leaves rather unaesthetic interproximal embrasures. Once again the UCLA abutments are not patient removable so the prosthesis is fixed in the patient's mouth and these open embrasures are required to provide periodontal access.

Frequently, nonparallel implant abutments create situations that leave the implant collars and sleeves exposed. The only non-surgical way of dealing with this problem is to overcontour and overextend the porcelain and metal. Since most patients expect an aesthetically pleasing result, overcontouring and ridgelapping the porcelain and metal to hide these necks has become more predominant. However, the overcontoured porcelain often smothers the peri implant sulcus making it virtually impossible to clean.

In order to provide the ideal embrasure spaces, the mesial distal width of the abutment teeth must be wider as they emerge from the tissue. For the screw retained bridge this once again means creating a "ledge" of porcelain to compensate for this discrepancy. The same situation occurs even more frequently in a buccal/lingual direction where on the labial aspect, the porcelain is often extended up onto the ridge beyond the peri implant sulcus to create the proper cervical margin placement, lip support and emergence profile.

From the lingual or palatal aspect improper emergence profiles often exist due mostly to the narrow cervical neck area of the implant abutment assembly. When the contours of the transmucosal collar are followed or even when direct abutments are contoured, large spaces are created which not only serve as a food trap but also feel foreign to the patient's tongue. There is no simple solution to this problem, because creating an overhang of metal or porcelain with a screw retained prosthesis to accurately reproduce the normal emergence profile of the natural teeth would make it almost impossible to clean.

As mentioned earlier, at least one supplier, 3I, has attempted to solve this problem by tapering the tissue using new tapered healing collars. As discussed immediately below, the screw retained prostheses which replace these tapered healing collars rattle loose. Therefore, it is not enough to simply taper the tissue, for frequently the prostheses have to be overcontoured. The solution is to eliminate the screws and make the prosthesis patient removable.

At an implant symposium (September 1993) in New York USA when the topic of discussion was confined to implant failures, Dr. Carl Misch was quoted as saying, "Screws rattle loose." (Indirect Verbal Communication.) This is true, but not only do they come loose, they also fracture. This fracturing, which has been reported repeatedly in the literature, is due to biomechanical overload which frequently causes the weakest link in the system to break. In the inventor's opinion, to have screws fracturing as a normal event is no way to maintain patient confidence or deal with the problem of biomechanical overload. As just mentioned, the solution is to simply design a retrievable system that does not have gold alloy screws and a system that has shorter stronger fixation screws. It must be remembered that once the fixation screw breaks the prothesis is no longer passive fitting.

One final problem with this type of prosthesis is the incorporation of screw-joint prestress which occurs when the screws are used to tighten down the framework. Tan et al. summed it up by saying, "Tightening the prosthesis onto the intraoral abutments may make the framework appear to fit, but may hide the existence of a prestress within the components and framework induced by this screw tightening. The superimposition of fractional stress (e.g., from mastication) upon this prestress will make the prosthesis more prone to failure, especially by long-term fatigue." K. B. Tan, J. E. Rubenstein, J. I. Nicholls, R. A. Yuodelis, *Three Dimensional Analysis of the Casting Accuracy of One-Piece Osseointegrated Implant-Retained Prostheses,* 6 Int'l J. of Prosthodontics 346–63 (No. 4, 1993).

The Precision Attachment Assembly Using Existing Technology.

This prosthesis illustrates the benefits of precision attachment removable assemblies, but also makes the point that limitations imposed on this case by conventional abutment systems can be corrected if UAS or MUAS technology is incorporated.

Assuming that the patient has an adequate number of implants to carry the load of an implant-supported prosthesis, most patients when given the choice, would prefer the crown and bridge prostheses to the overdentures. However, the periodontal maintenance that the patient removable systems offer is a very big plus. To have the feel of fixed crown and bridge that is able to be removed on a daily basis would be ideal.

The following case report details the use of such a system. Even though hardware according to the present invention was not used for reasons just discussed, the purpose of this clinical case was twofold: (1) to show the benefits of precision attachment assemblies and (2) to help clinicians realize the limitations imposed on this case by using existing technology. These problems and shortcomings will be disclosed as will an alternate solution using a working prototype model. Once again a clinical case can be organized for further demonstration purposes.

A 53 year old female wore a complete upper denture and complained that it had never fitted correctly. The patient also wore a cast partial lower denture but wanted really to rid herself of both dentures and was interested in implants. After consultation with an oral surgeon it was determined that she was a good candidate for implants.

The treatment plan called for the placement of a precision attachment removable crown and bridge prosthesis supported by at least 6 endosteal implants.

In March 1990, six Dentsply HA coated microvents were placed in the maxillary arch. They were of varying diameters but all were between 10–13 mm in length. There were at least three sites that proved to be unacceptable because the bone was either too soft or the maxillary plates were too knife edged and this led to perforation. Thus, only two implants were able to be placed in the upper left quadrant. In hindsight this may have proved to be an excellent site for a blade form implant. If the surgeon had the opportunity to retreat this case in 1993 either a blade form implant would have been placed or bone augmentation and a tissue guided regenerative procedure would have been undertaken to treat the upper left quadrant.

In September 1990, the six maxillary implants were uncovered using a full arch mucoperiosteal flap, and healing collars were placed. However, during the healing period on several occasions the collars came loose creating tissue ingrowth between them and a subsequent "foul odor." To correct this problem the collars were removed, the tissue tags were removed and the healing collars were screwed back to place with. Bioseal coated on the screw threads.

In early November 1990 a combination of conventional angled titanium abutments and hex lock abutment analogues were placed to assess the position and axial inclination of the implants. Because of anatomical and surgical limitations several of the implants were placed at rather severe angles. Even utilizing 15° and 30° angled titanium abutments, "draw" could not be achieved in a conventional manner, even after aggressively grinding down the abutments. As a result, gold telescopic copings had to be fabricated overtop of these abutments to align all six implants. Oval shaped openings were made in the facings of these copings that lined up with the screw holes in the HLAs and ATAs allowing for abutment retrievability. This unfortunately also created a problem with screw loosening. Before the copings were cemented into place (which also created some concern) the patient removable crown and bridge framework had to be fabricated.

Four KSG Audax precision slide attachments were used. The matrix components were cast as part of the gold telescopic copings on the distal aspect of abutments #15, 14, 23 & 25. This was an exceedingly difficult task for not only did "casting to" put the attachments under a great deal of temperature stress but, because of the abutments' central access bore design, the attachments had to be mounted well outside the central long axis of the implant. Trying to minimize the lateral stresses that this created by altering the abutments proved to be virtually impossible.

Once the copings were tried in and were fitting precisely, they were cemented permanently to the abutments. A palladium-gold crown and bridge framework was made then to extend from #16–#26. On the internal aspect of the crowns for teeth 15, 14, 23 & 25 the patrix components of the KSG attachments had been cast. The fitting of the framework and the casting of the attachments created a strong concern over passive fit. Without being able to utilize the technology of the present invention, confirming a passive fit was impossible. In fact the extra film thickness of the cement used to cement the copings was enough to disrupt the alignment of one attachment and then the entire case. Rather than trying to remove the coping from the abutment, the patrix component in the framework was carefully cut out and the framework was relieved. The patrix component was then fully seated back into the matrix and a pick up impression was taken with the framework in place. The lab used this impression to index the position of the patrix and then resolder it. This was a very complicated, time consuming endeavor but the prosthesis did finally fit. Four small threaded screw holes were used to check the internal fit of the framework and make sure that it was seating evenly on the copings and not being held up by a misaligned precision attachment.

The framework was extended outward covering the palatal tissue and was created to butt joint the palate in order carefully to duplicate the emergence profile and contour of the natural dentition.

Under normal circumstances, such as with a screw retained or cementable bridge, this could not have been done simply because the patient would have been unable to keep the area clean. Since the patient could remove and clean the precision attachment appliance daily, however, this overcontouring of the framework was possible. As the porcelain was applied to the framework it too was extended labially, palatally and interproximally out over the peri implant sulcus. These phonetic and aesthetic advantages cannot be achieved unless the clinician is prepared to ridge lap the tissue and overextend the porcelain. Without these contours proper lip support could also not have been achieved with a crown and bridge prosthesis.

Two bisque bake try ins were completed to finalize the occlusal scheme and the final contour of the prosthesis. However, due to the bulk of the HLAs and ATAs and the added bulk of the telescopic copings, by the time porcelain was added to the framework the incisal-lingual contours of the prosthesis were too bulky. This "bulkiness" interfered with the patient's speech. The finished appliance was then given to the patient who was instructed to wear it at all times but to remove it twice daily to clean around the copings and the underside of the prosthesis. The patient was instructed to clean with a combination of a Hydrofloss machine and a Rotadent toothbrush. As an adjunct, the patient has found that by looping superfloss around the copings and crisscrossing the floss she can maneuver it into the peri implant sulcus which needs careful cleaning, occasionally the patient develops an odor problem as bacteria get trapped in the occlusal access bore.

The patient has had absolutely no problem removing the prosthesis on a daily basis and has stated that "the appliance feels as if it were fixed into place." Implants associated with overdentures cannot claim this same stability. However, they can claim to be more accessible than their screw retained or cementable crown and bridge counterparts. By the same token, this patient removable precision attachment prosthesis allows for even better access to the implant abutments because there is no tissue bar. Complete and unrestricted 360° access allows for unbeatable periodontal cleansing. This is perhaps one of the most important aspects of this technique, one which is carried over to the design of the present invention.

Conclusion.

The unique design of this precision attachment system that allows it to be removed on a daily basis not only permits more predictable home care but also circumvents the need to use set screws to anchor the superstructure. For this reason there are no screws that perforate the external surface of the crown and bridge assembly.

As already pointed out when eccentric screw positions are created, destructive lateral forces and stresses on the prosthesis lead to "retrograde peri implantitis" which occurs due to microfracturing in the bone. With a precision attachment assembly such as this one the problems associated with eccentric screw position are eliminated.

A great deal of work has gone into circumventing the aesthetic problems associated with the partially or completely edentulous ridge. For example, when proper gingival labial contours cannot be achieved due to implant position or tissue defects, bone grafts or tissue guided regeneration procedures may be, used in partially edentulous cases. However for the completely edentulous maxillary ridge, where resorption is often moderate to severe and is more generalized, these alternatives are not completely successful due to resorption and slumping. Ridge augmentation in situations such as this usually involve significant autogenous bone grafts from either the iliac crest or symphysis area. For most people major reconstructive surgery such as this is not a practical solution.

Improper implant position creates other problems as well, including path of insertion problems, eccentric screw positions, and aesthetic and occlusal discrepancies. With the introduction of the pre angled abutments some of these problems were magnified. Many people believe that the forces of occlusion being placed on these angled abutments are not being directed along the vertical axis of the implant fixture. Furthermore, when telescopic copings are used to create a common path of insertion among multiple abutments, the margin of the coping often creates an aesthetic problem, for they have to be raised occlusally to allow for "draw" with the other abutments. This causes the metal collar of the telescopic coping to show from the labial aspect. This metal collar cannot be masked unless the PBG crown is overextended and overcontoured. Once again this makes cleaning both the tissue and the prosthesis difficult.

Studies have shown that the peri implant sulcus is lined with a sulcular epithelium and more apically with a junctional epithelium. It appears that the sulcus is very similar to that of a natural tooth, but without the periodontal ligament. Clinically this is very relevant to the restoration of the edentulous anterior maxillary jaw. Often the overlying tissue is thin and friable and because the body likes to maintain a "biologic width" between the crestal bone and the base of the peri implant sulcus, subgingival margin placement is not always possible. When inappropriate prosthetic contours are created to correct for such problems the periodontal maintenance of such an appliance is put in jeopardy.

One other problem that this thin friable mucosa often creates is a lack of interdental papillae. Even with shorter transmucosal collars that diverge more at their junction with the abutment, it is very difficult to get the proper emergence profile and create or simulate interdental papillae. The result is once again an aesthetic compromise. Even with more anatomically correct implant systems the resorption of the ridge combined with the thin mucosal coverage often makes it impossible to achieve proper aesthetics without overcontouring or over-extending the porcelain. Overcontouring and overextending truly creates a catch-22 situation: Either periodontal maintenance problems or aesthetic compromise.

Periodontal disease is still the leading cause of tooth loss in adults and now as more and more osseointegrated implants are being placed the condition known as peri implantitis is becoming more prevalent. It is therefore extremely important that full arch reconstruction allow for adequate cleansing of the peri implant sulcus. The precision attachment prosthesis is ideally suited for this because the appliance can be removed daily, with firm bilateral pressure. This allows the patient complete access to both the highly polished gold copings and the underside of the bridgework.

Note that the copings are either supra gingival or level with the gingiva. This prevents any possible encroachment on the biological width of the connective tissue between junctional epithelium and crestal bone. The collar of the abutment may show but the porcelain to metal suprastructure covers it completely, by virtue of its overextended porcelain margins. This ridge lapping of porcelain, overextending and filling up the interproximal gaps, only works if the appliance can be removed daily; otherwise peri implantitis and potential implant loss can occur.

Overlapping the peri implant sulcus with both the metal framework and the porcelain is not an acceptable situation on either a cement or screw retained prosthesis for it is imperative that this sulcus be cleaned. Furthermore, the lingual extension of this framework has an emergence profile that accurately reproduces that of the natural dentition, unlike the other prostheses where the lingual surface is usually scooped out.

There are features that cannot be achieved in the edentulous jaw and other crown and bridge systems without severely compromising the periodontal health of the tissue and patient comfort. For instance, a non parallel abutment requires a telescopic coping which creates a visible metal surface that cannot be covered, without creating an unfavorable overcontour and one which cannot be readily cleaned. The alternative is either to leave the metal exposed or utilize one of the new ceramic abutments. Both options allow for cleansibility but are rather unaesthetic.

One final point should be made about those patients who are edentulous and have lost their teeth to periodontal disease. Can a patient such as this be expected to go from a complete denture to a full arch prosthesis and develop all the necessary habits to keep the appliance clean? If the appliance is screwed or cemented into place this would make it exceedingly difficult, if proper aesthetics are to be maintained. We owe it to these patients to make everything as accessible as possible and this is why the removable denture systems are so popular. However their aesthetics and patient comfort are not the best. The solution is a precision attachment crown and bridge prosthesis which can be removed, to allow for cleaning on a daily basis. At the present time, the only other crown and bridge options are cementable or screw retained systems which cannot be removed by the patient.

Improving on the Precision Attachment Assembly Using UAS/MUAS Technology.

Using state of the art conventional abutments, this precision attachment assembly demonstrated some major limitations. Beside the fact that it had to use secondary telescopic copings, the most obvious limitation of the foregoing system was the use of abutments with central access bores. This creates screw loosening problems and an inability to place the precision attachment housings within the normal contours of the abutment. This in turn leads to non axial loading of the implant bone interface and can create destructive lateral forces that can lead to retrograde peri implantitis.

Had the UAS/MUAS system been used in this particular case, there would not have been a need to fabricate telescopic copings. Without the copings, there would have been no need to use cement to join them to the abutments and risk altering the attachments' position (which did in fact happen). In fact, fewer parts would have been necessary without the copings and there would not have been the problems associated with a central access bore.

The hours and hours that were spent aligning the hex and octagon position of these abutments, every time the abutments were tied in, were also wasted time. This could have been avoided if UAS or MUAS threaded base 10 assemblies were used. There are also clinicians who believe that one does not need anti-rotational abutments for bridgework; however this is simply not true, when the present invention is used. In order to align two or more precision attachments accurately, the exact rotational position of the abutments must be reproduced. The problem in assembling precision attachment prostheses with existing abutments that do have anti-rotational capabilities is that there are simply too many hex-octagon or other mechanical interlocking combinations. For many abutments, these multiple rotational positions are a key selling feature, which is fine if the clinician needs only to align one or two abutments. For five or six, however, the potential number of rotational positions for a commonly used ATA is $24^6$ or 191,000,000!

With the MUAS/UAS System one of these interlocks is eliminated and is replaced with a threaded component, which reduces the number of rotational positions for each abutment to 6 or 8 depending on the individual system. Needless to say, the potential number of rotational positions is greatly reduced.

For the patient mentioned above, although there were no secondary set screws to fracture or loosen, several of the main fixation screws did work themselves loose. This could have been avoided had a UAS/MUAS System been used. It is this author's opinion that screw loosening is a very good indication of a non passive fitting prosthesis; in this case it is highly likely that it was a non passive fitting framework that caused the fixation screws to loosen.

The "bulky" aesthetic problem with the prosthesis, which is due to the access bore holes and the extra thickness required for the copings, ceases to be a problem with the present invention. Neither the access bore holes or the copings are needed and therefore the abutments can be made slimmer and more compact. As a result, so can the crown contours. This also helps solve the problem of speech articulation discussed earlier.

Another major limitation with this conventional system has to do with passive fit. In the inventor's opinion, any system that has central access bores and screw loosening potential has a problem with passive fit because, as soon as the screws loosen, the abutments are not being loaded in the same manner. This is what frequently leads to screw breakage and likely why the Branemark system screws are designed to break. The present invention, by contrast, simply eliminates all occlusal screws and thus eliminates risk of loosening or breakage.

The problem of passive fit also has to do with the fact that precision attachments for this conventional prosthesis are cast to place in the lab which creates a potential source of distortion. The conventional abutments are not designed to allow for intra abutment resin bonding of attachments— without which a passive fit cannot be achieved.

Upon examination of the prototype models of this specific case, it becomes very apparent that use of UAS or MUAS abutments would reduce or eliminate all of the problems associated with this precision attachment assembly.

It should also be noted that the framework is made of titanium which is approximately one quarter the weight of the original prosthesis. Individual crowns or sections of crowns can also be telescoped on the framework and lingually set screwed to position. Telescoping crowns in this manner serve two purposes: (1) so that damage to one section of the crown or crowns does not require refiring of the entire bridge or any of the attachments; and (2) if vertex attachments according to the present invention are used the clinician needs to be able to access the occlusal spreader screws to adjust the tension on the attachments.

Fabricating Precision Attachment Assemblies with Resilient Cores using Modified UAS/MUAS Technology.

Careful attention must still be paid to prevent overloading the implant bone interface especially in patients with heavy occlusal function (i.e., bruxism and clenching). Normally this is done by narrowing the occlusal table, removing damaging lateral forces of occlusion and premature contacts. However in many instances this is not enough, especially during the first year the appliance is being worn when the implant-bone interface is still maturing. The IMZ suppliers recommend that an intramobile element (IME) made of polyoxymethylene be used as a shock absorber. This is an excellent idea as stress distribution, shock absorption and proprioception are all said to be facilitated by the use of an IME.

Unfortunately the utility of the IME of the IMZ system is limited because of potential screw loosening problems, access bore location, a high percentage of IME breakage and the fact that the overlying prosthesis cannot be made precision attachment patient removable. M. L. Perel, *Interview With Dr. H. J. Gulbransen: Combining Implants and Natural Teeth Within the Same Arch,* 4 Dental Implantology Update 74–76; (No. 9, 1993); R. C. Hertel, W. Kalk, *Influence of the Dimension of Implant Superstructure on Peri-Implant Bone Loss,* 6 Int'l J. of Prosthodontics (No. 1, 1993); E. A. McGlumphy, W. V. Campagni, L. J. Peterson, *A Comparison of the Stress Transfer Characteristics of a Dental Implant with a Rigid or a Resilient Internal Element,* 62 J. of Prosthetic Dentistry 586–93 (No. 5, 1989); D. C. Holmes, W. R. Grigsby, V. K. Goel, J. C. Keller, *Comparison of Stress Transmission in the IMZ Implant System with Polyoxymethylene or Titanium Intramobile Element: A Finite Element Stress Analysis,* 7 Int'l J. Oral Maxillofacial Implants 450–58 (No. 4, 1992); R. K. K. Ow, K. H. Ho, *Retrieval of the Resilient Element in an Osseointegrated Implant System,* 68 J. Prosthetic Dentistry 93–95 (July 1992). As an example of this, IME's could not be used in conjunction with the previously discussed prosthesis because the conventional abutments could not be made compatible with the IME.

Therefore it is obvious that a system such as the UAS/MUAS whose resilient core does not cause all of these problems and is universally compatible would be perfectly suited for this purpose. Not only can such Modified UAS/MUAS Assemblies be used to help absorb excessive occlusal loading, but they can also be used to help progressively bone load the prosthesis. One of the biggest differences between the IME and the resilient core is that the resilient cores can easily be removed and replaced without disturbing the threaded base 10-implant connection or fixation screw. This is not possible with the IMZ system; additionally, the exact rotational position of the abutment of that system cannot be accurately duplicated either.

Furthermore, because of the IME's central access bore and fixation screw, there are some critics who believe that it is the bending moment exerted on the elongated fixation screw that accounts for this system's resiliency. Unfortunately, this puts a great deal of stress and strain on the screw itself and is considered to be the reason why the screws loosen and fracture.

With the resilient core system of the present invention, there is no central access bore or elongated fixation screw. Accordingly, in addition to solving these problems, this feature also allows cavities to be created within the abutment for precision attachment placement. The resilient core system can also be readily replaced with a titanium analog which duplicates its size and shape exactly. The titanium analog simply eliminates the "flex" in the system when the clinician feels that a more rigid prosthesis is desirable.

One additional very important advantage that the resilient core enjoys, because it fits solidly onto the threaded base 10 portion of the Modified UAS/MUAS System, is that it is adapted to function with any implant system including blade form implants. The IMZ system does not have this sort of "flexibility."

An Alternative Solution for the Partially Edentulous Situation.

A recently featured article in the "Journal of Oral and Maxillofacial Implants" by Svensson et al. described how the position of four misaligned Branemark implants was corrected by a segmental osteotomy procedure. B. Svensson, R. Adell, B. Swarte, *Correction of Implant Malalignment by Segmental Osteotomy: A Case Report,* 8 Int'l J. of Oral and Maxillofacial Implants 459–63 (No. 4, 1993). This procedure was used because the initial palatal placement of the fixtures resulted in phonetic and hygiene problems for the patient. In fact, "the patient could not tolerate the prosthesis because of phonetic problems (lisping) and inadequate tongue space." She also "spent a disproportionately long time every day trying to gain access to and clean her implant abutments." Id. The article further states that it was the Buccal extension of the prosthesis that resulted in the hygiene access problem. If a precision attachment patient removable prosthesis according to the present invention had been initially fabricated, the inventor believes that significantly less time would have been required for optimum oral hygiene and superior aesthetics and phonetics. The only concern left with the original prosthesis would then have been to create the proper dentoalveolar relationships with a rigidly cantilevered prosthesis. For this reason, the inventor concurs with Svensson et al. that the segmental osteotomy was the correct treatment, although not with the choice of the final prosthesis.

After the osteotomy procedure was performed a similar prosthesis was fabricated. However this time it "did not intrude on palatal space" or have such an "extensive Buccal Flange." It did, however, remain screw retained, the access bore holes were still covered over with a temporary cement and the necks of the implants were still left exposed.

The final prosthesis could just as easily have been made precision attachment patient removable which would have allowed more ridge lapping and far better hygiene access to the individual abutments. The ridge lapping would have allowed for better aesthetics and would have reduced the passage of air above the prothesis.

The use of precision attachment assemblies in similar situations where the prosthesis is either screwed or cemented to place can be readily shown to improve on both form and function.

Part 5: Dealing with the Problems of Combined Implant-Tooth Restorations.

There is a great deal of controversy regarding prosthesis design and the combined implant-tooth restoration.

However, most people will agree that implants are most frequently joined to natural teeth to lend extra support and redistribute the occlusal load in situations where the natural dentition is diminished or shows signs of increased mobility.

Many clinicians endorse the use of Boos type attachments (semi precision tube and lock) to connect the tooth—and fixture-supported segments of combined implant-tooth bridgework. I. Ericsson, U. Lekholm, P. Branemark, J. Lindhe, P. Glantz, S. Nyman, *A Clinical Evaluation of Fixed Bridge Restorations Supported by the Combination of Teeth and Osseointegrated Titanium Implants,* 13 J. Clin. Periodontal 307–12 (No. 4, 1986). Unfortunately the tooth segment adjacent to this attachment frequently becomes intruded leaving the paternal part of the attachment protruding. Furthermore, pronounced bone loss can often be seen around the implant abutments when this type of interconnection is used. It is the inventor's opinion that when semiprecision attachments and other non rigid connectors are used they do not provide adequate splinting for mobile teeth. Furthermore, any amount of freedom in the attachments actually increases the "cantilever effect" to the implant abutment (essentially the intruded teeth become cantilevers). This can undoubtedly lead to an overload of the implant bone interface and result in bone loss. In the Ericsson article this is exactly what they found clinically, "pronounced bone loss around the fixture abutments." Id.

There are other clinicians who feel that implant supported teeth should be isolated from natural teeth in the partially edentulous patient; however, when the implants are isolated, a greater number of complications often arise. These include: (a) component fracture; (b) a higher incidence of loose screws; (c) difficulty in equilibrating the occlusion; and (d) implant failure.

On the other hand, there are those who feel that one can cautiously connect teeth to implants in a fixed/fixed manner and others that feel this should be done with intra-coronal semi-precision attachments as Ericsson and others have detailed. Still others feel that rigid screw retention of the components is the solution but this has proven to lead to idiopathic bone loss around the implant. Perhaps the most plausible approach to date has been offered by Dr. Howard Kay as follows. Let us take, for example, the almost completely edentulous arch, save 3 or 4 natural teeth. Kay's recent article points out that when the clinician is joining implant and natural teeth together, the use of intra mobile elements seems to enjoy "the highest level and largest number of overall long-term reported implant success." H. B. Kay, *Free Standing Versus Implant-Tooth Interconnected Restoration: Understanding the Prosthodontic Perspective,* 13 Int'l J. of Periodontics and Restorative Dentistry (No. 1, 1993). It seems that, as Kay points out, the semi-precision attachments, i.e. tube locks, "are inherently unstable and display the potential for migration of natural tooth segments". Id. Furthermore, Kay adds that the use of rigid tooth-implant connections can lead to "unexplained bone loss around implants." Id. These conclusions were reached based on the results of over 5,000 tooth implant cases using IMZ implants.

The basic concept behind the IME is that it is made of polyoxymethylene which can absorb and distribute occlusal stress to the implant bone interface more evenly than metal to metal components. In effect the IME simulates the periodontal ligament for the osseointegrated implant and effectively reduces or eliminates any discrepancy in mobility patterns between natural tooth and implant abutments.

Many studies, however, have questioned the IME's ability to reduce the transmission of occlusal forces. One clinician found that these stresses were not reduced when the IME was used and that maximum stress concentrations were located in the fastening screw. Others have postulated that the resin element could protect the screw from fatigue at the top of the implant, but that movement of the screw within the IME may also explain the reported, but undocumented, tendency of the screw to "back out" on an occlusal direction.

It is evident from the literature that there are conflicting reports as to the efficacy of the IME. Although the inventor questions the use of IME's because they can break and for other design reasons, he shares the philosophy of incorporating resilient connections into implants. One solution: Design a system that (1) does not have the same stress placed on its elongated central fixation screw; (2) can be removed and replaced without disturbing the rotational stability of the prosthesis; and (3) has no occlusal access or tendency for the screw to back out.

By making these three changes to the resilient component, one arrives at the Resilient Core UAS or MUAS abutment. There is also one other very important distinction to be made, and that has to do with the way certain clinicians choose to restore these combined implant-tooth cases. By incorporating IMEs they limit the prosthetic design. They endorse the use of dentist retrievable screw fixtures such as the T Block and CSR attachment. T Block structures are used to help reconstruct the maxillary arch in segmented screw retained sections. The remaining natural teeth are splinted and cemented. CSR Attachments are used to splint natural teeth and implants together in the lower arch, but feature numerous screw holes. The final result is often a full arch appliance that has ridge lapped prosthetic abutments which cannot be removed other than by a dentist. As consequence of these designs, the patients must carefully floss anteriorally where the crowns and pontics frequently make contact with the tissue but are "scooped out" lingually for hygienic access. Posteriorly, increased spaces must be created to allow for better toothbrush access.

When IMEs are used anteriorly this creates further aesthetic problems. IMEs are placed so that they are exposed above the gum line; their constricted diameter renders it almost impossible to create normal anatomical contour without ridge lapping the tissue. In the inventor's opinion these sorts of nonpatient removable reconstructions make it exceedingly difficult for the patients to clean their mouths efficiently, to say nothing of the potential phonetic, aesthetic and screw loosening problems.

When clinicians use the IMZ system, occlusal access bores are difficult to eliminate. In single tooth implant applications, if there are even minor angulation discrepancies, then telescopic copings must be used to prevent the large access bore holes from opening onto the labial surface of the teeth. Other problems include, as Kay himself has stated, "with freestanding ceramometal restorations . . . I have experienced an unquestionably higher incidence of problems associated with loosening and breakage of fastening screws, breakage of abutment screws and intra mobile element failure of implants and in one case breakage of implants." Id.

Figure 35:
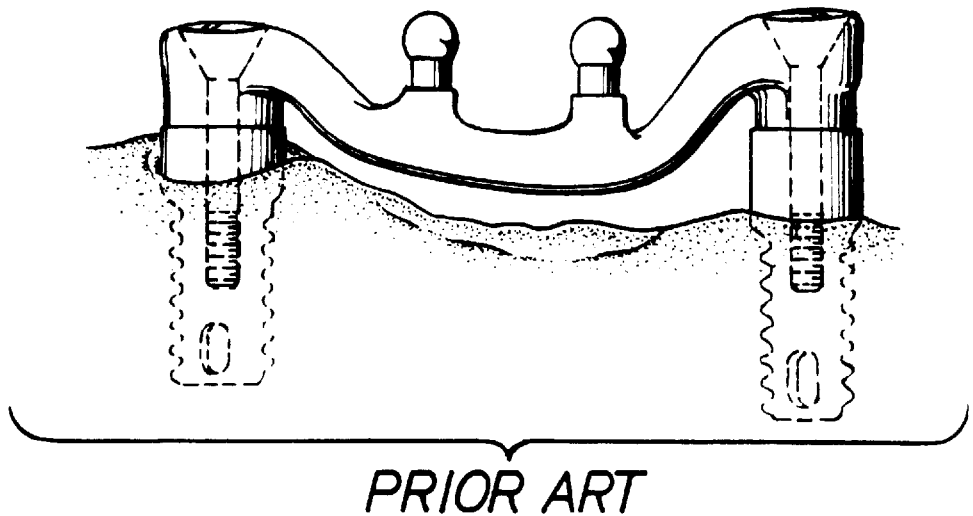
FIG. 35 is a cross sectional view of an overdenture which employs conventional precision attachments and implant abutment systems.
Figure 36:
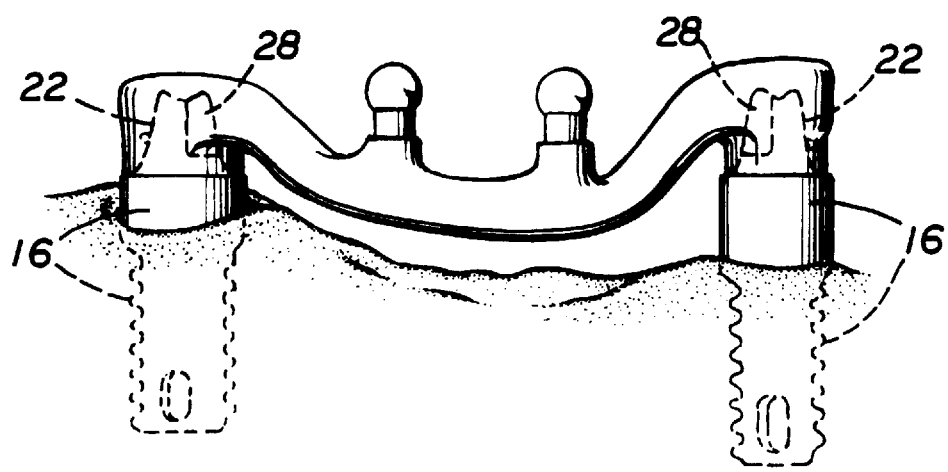
FIG. 36, by comparison, is a cross sectional view of an overdenture similar to that of FIG. 35, but which employs precision attachments and an implant abutment according to the present invention.

The present invention offers a unique range of prosthetic options. FIG. 35 and 36 compare, for example, a bridge 82 fashioned according to the present invention with a conventional bridge. This bridge is secured conventionally to a prepared natural tooth and a conventional IMZ implant and abutment which features an occlusal bore. Bridge 82 of the present invention, by contrast, is removably attached to the natural tooth via a precision attachment 28 located on the natural tooth coping and to a Modified UAS featuring a resilient core 44 to replicate the ligimentation and mobility of the natural tooth. Note that the Modified UAS has no occlusal bore hole.

The following case is another example of such a Precision Attachment Patient Removable Prosthesis according to the present invention supported by a combination of Modified UASs (which feature resilient cores) and natural tooth telescopic copings. This prosthesis can either be made as a segmented bridge or a one piece full arch splint. In either situation ridge lapping can be used effectively to "hide" the resilient cores simply because the prosthesis is patient removable.

Consider the following working prototype model fashioned after an actual clinical case. This patient had gold copings placed on all of her remaining natural teeth and their margins were finished ever so slightly below the gingival crest. In this particular situation elective root canal therapy was performed on five of the remaining natural teeth in order to create proper resistance form and because prior to this treatment the teeth had been poorly prepared. Exacting attention to detail began with dense, accurate endodontic fills and precisely fitting cast posts and cores. The gold telescopic copings that were placed overtop of the cast posts and natural teeth were all machine paralleled with 2–4 degrees axial taper.

From the Passelipse X-ray it was evident that four implants were placed into the patient's maxillary jaw, two of which were placed (#15 & 26) in conjunction with bilateral sinus augmentations. Also of interest is that in the anterior implant sites the #12 had inadequate bone around it, requiring that allografted bone and a lamellar strip of bone be used to regenerate the deficient areas. Because this involved replacing both labial and palatal bone, primary tissue closure could not be achieved. However, the tissue granulated in nicely over the exposed lamellar strip providing a good thick band of attached gingival tissue because the Lamellar strip was resorbable. (See Section II.)

This is how the patient was left—in a temporary occlusion, and all subsequent steps have been completed on the prototype working model.

On the prototype working model, the four implant supported teeth are all reconstructed using Modified UAS assemblies. All four abutments have intra abutment slide precision attachments secured to place using the resin bonding technology of the present invention. The attachments are paralleled to the adjacent telescopic copings using a parallelometer. Other abutment systems cannot position the attachments in this manner because they all have central access bores and the attachments can therefore only be placed extracoronally. Occasionally, there is insufficient space between the implant and the natural tooth to accommodate even an extra coronal cantilevered attachment. With the UAS System this is not even a concern because all attachments can be placed within the abutment, which allows the forces of occlusion to be directed in a more axial direction. This is one of the most outstanding features of the UAS/MUAS Systems.

In situations where increased retention is required, the telescopic copings can be fabricated with either machined grooves, slots or even dimples. The dimples can be engaged by adjustable I.C. plunger attachments which can be resin bonded into the overlying framework.

As discussed earlier, this prosthesis can be segmented or fabricated as one piece. The choice of designs will depend on the individual patient but a sensible guideline would be to keep the minimum segment size to no less than three units. Basically, the only reason one would want to segment the prosthesis is to appease the patient's psychological need not to be without all of their teeth.

The copings on the cuspids also have one added feature, which is precisely machined dimples that are engaged by adjustable I.C. plunger attachments. The I.C. attachments are housed in resin in the overlying precision attachment framework, and are incorporated into the prosthetic design to enhance retention. This prosthesis can in fact be made in as many as four sections. Section #1 is the cementable PBG crown fabricated for tooth #24 to maintain the vertical dimension. If the rest of the segments can be fabricated so that at least one implant and one natural tooth are splinted, it is not necessary to splint the entire arch together. For example, Section #2 of the segmented framework may be the six unit anterior bridge that splints four natural teeth and two implants together. In order to hide the Modified UAS's the porcelain and metal of the framework can be ridge-lapped. This also helps create full anatomical contour. Section #2 could be the upper left four unit bridge and Section #3 could be the upper right three unit bridge. Alternatively, Sections #1 and #3 could be combined as one so that the bridge has only three sections. As long as natural teeth and implants are splinted it is not necessary to rigidly screw retain the entire arch together as so may clinicians and manufacturers suggest. If the entire prosthesis is to be fabricated in a one piece horseshoe splint at the very least it should be patient removable. Once again it too can also be ridgelapped to create full anatomical contour and eliminate unsightly spaces.

When resilient cores according to the present invention are used as a part of UAS or MUAS Assemblies, the implant abutments are able to replicate the periodontal membrane of the natural teeth. This allows for a much more even distribution of occlusal forces and allows the implant abutments to function similarly to the natural teeth.

In the past, rigid fixation of implant and tooth segments lead to the development of the "Vital Pontic Theory" whereby plaque and fluid could accumulate between a telescopic coping and the overlying framework that was rigidly attached to the implant abutment. Since the implant abutment could not move, a constant hydrostatic pressure buildup between the coping and the framework lead to a separation and intrusion of the natural tooth. This would leave that portion of the framework overtop of the natural tooth unsupported and so the term "Vital Pontic" was coined. Vital pontics cause concern because as the tooth intrudes, the balance of occlusal forces are taken up by the implant and a cantilevering effect is created.

The inventor believes that because the implant abutments no longer need be rigidly attached to the frameworks, they can function just as natural teeth do. Therefore, for the same reason that patient retrievable precision attachment bridges work perfectly on natural teeth with no risk of hydrostatic pressure buildup and tooth intrusion, these new prosthetic designs will also work in combination tooth-implant situations.

Part 6: Overdenture Applications.

For many people, fixed-detachable and now patient removable precision attachment crown and bridge prostheses are not a viable option due to financial limitation. For those people, three or four implants, a cast bar design and an overdenture is frequently the better solution. Unfortunately with existing abutment systems there are no cast bar designs that do not have exposed fixation screws. Therefore, with these designs there are still the potential problems associated with screwing down the bar, passive fit problems and hygienic access to name only a few. M. Perel, *An Interview with Charles E. English: The Mandibular Overdenture*, 4 Dental Implantology Update 9–14 (No. 2, 1993); R. B. Johns, et al., *A Multicenter Study of Overdentures Supported by Branemark Implants.* However, by incorporating UAS/MUAS technology these problems cease to be of concern because these new abutments allow for certain design modifications. As an example, when two implants are placed in the symphysis of the lower jaw and UAS/MUAS abutments are secured to position two intra abutment precision slide attachments can be resin bonded to place. A new bar design as part of the present invention can then be fabricated, but with at least three significant differences:

(1) The new design as shown in FIG. 36 incorporates two internally mounted precision attachment patrix components rather than simply holes; (2) because of the slide attachments, the newly developed bar of this present invention is now patient removable and (3) because the attachments are resin bonded to position, the cast bar design is passive fitting. With UAS/MUAS technology, there no longer exists the need to create bar designs with external screw holes. The actual milled suprastructure of the cast bar can be as it was before; of almost any design and can incorporate any number of retentive devices for cooperation with the inside of the denture. These cast bar modifications can be incorporated into any overdenture design, using any type of implant system using when the UAS/MUAS assemblies are employed.

Such an overdenture system according to the present invention is shown compared to a conventional bar in FIGS. 35 and 36.

Part 7: A New Classification of Implant Prosthetics.

Introduction.

The present invention makes it apparent that a new prosthetic classification for implant dentistry is required. The following classification system reflects changes in both abutment and prosthetic designs by incorporating a new order of precision attachment patient removable prosthetics.

The ADT Classification.

There are four basic intraoral categories;

(1) Fixed prosthetics;

(2) Patient removable overdentures;

(3) Fixed/retrievable prosthetics; and (4) Intra Abutment Precision Attachment Patient Removable Prosthetics.

Before we examine these categories individually, clarification must be given to the following terms as there is much confusion over what qualifies as "Fixed," "Removable," "Fixed/Retrievable" and now "Precision Attachment Patient Removable". Furthermore, it is important to clearly distinguish between "Removable" and "Retrievable."

Is all that is Retrievable, Removable? The inventor does not believe so; instead, he believes that a prosthesis should be referred to as a Patient Removable or Dentist Retrievable device, and that the term should not be interchangeable.

(1) A Fixed Prosthesis—should refer to a crown and bridge appliance that is rigidly attached to the implant abutment(s) by a permanent cement. It is therefore neither removable nor retrievable.

(2) A Patient Removable Overdenture—should refer to acrylic overdenture systems that anchor to the implant abutments with, or without the use of a tissue bar. In both situations, these denture systems can be removed by the patient. Acrylic overdenture systems that utilize a tissue bar can incorporate a wide variety of semi precision or precision attachments to stabilize and aid in the removal of the overdenture. These tissue bars however, are held rigidly to the abutments by fixation screws and are dentist retrievable only.

(3) Fixed/Retrievable—should refer to an acrylic overdenture or crown and bridge prosthesis that is rigidly attached to the implant abutment(s) and or a combination of implant abutments and natural teeth. These prostheses can be anchored by primary fixation screws, secondary set screws and or temporary cement (which usually involves the use of telescopic copings). Fixed/Retrievable prostheses can utilize any number or variety of screw attachments. These attachments are usually mounted or incorporated into a secondary telescopic structure. These prostheses are not designed to allow for patient removability. As a consequence of this design limitation, these prostheses are usually not ridge lapped and are of a high water design. Frequently, these prostheses are also rigidly cantilevered.

(4) Intra Abutment Precision Attachment Patient Removable Prosthetics—This is the new classification category, and it can refer to:

(a) Acrylic Overdenture Systems—this category basically refers to a new design of tissue bars that have no external access screw holes and are anchored to the individual abutments by a wide variety of semi precision or precision. attachments. This makes the tissue bar patient removable. This is not to be confused with the patient removable overdenture category where the tissue bars are anchored rigidly to the abutments by fixation screws.

(b) Implant Supported Crown and Bridge Systems—refers to appliances that are rigidly anchored to implant abutments or a combination of abutments and natural teeth in a patient removable fashion. This involves the intra abutment positioning of separable precision slide attachments. This allows the patient to remove the overlying prosthesis and does not require a tissue bar. (c) Combination Crown and Bridge/Acrylic Denture Systems—this category refers specifically to stress broken denture situations where a crown and bridge system requires a hingeable denture saddle to lend tissue borne support in an non-implant bearing area of the mouth.

(d) Combined Implant/Natural Tooth Systems—this category refers to implant and natural tooth segments that are splinted together with resilient cores and precision slide attachments.

This new category has obvious advantages over the three previous categories because the prostheses are designed to circumvent the problems of screw loosening, screw breakage, patient cleansability, passive fit, esthetics, phonetics and axial loading.

The sub-classification of these four categories are as follows:

1. Fixed Prosthetics.

(a) Single tooth implant—cementable (it makes no difference whether the underlying abutment is retrievable because the overlying crown is permanently cemented).

(b) Multiple unit implant supported crown and bridge—cementable.

(c) Combined implant/natural teeth crown and bridge—cementable.

2. Patient Removable Overdentures.

(a) simple overdentures;

(b) tissue bar overdenture—with or without a cantilevered bar;

(c) spark erosion overdenture;

(d) HA-TI solder base overdenture;

3. Fixed Retrievable.

(a) ad modem Branemark denture—utilizes rigid cantilever and is screw retained;

(b) implant supported crown and bridge—single tooth crown:

held by primary fixation screw held by secondary set screw temporarily cemented multiple unit crown and bridge held by primary fixation screws held by secondary set screws held by telescopic copings and temporary cement (c) combined implant/natural tooth crown and bridge retrievable implant crown segments are joined to fixed natural tooth segments. The prostheses may or may not incorporate resilient components.

4. Intra Abutment Precision Attachment Patient Removable Prosthetics:

(a) acrylic overdentures—new bar designs according to the present invention fall into this category and (b) implant supported crown and bridge prostheses—these systems have no external access screw holes, the precision slide attachments are mounted within the contour of the abutment and the prostheses is patient removable and has no tissue bar.

(c) combined crown and bridge/acrylic denture systems—stress broken denture (d) combined implant/natural tooth prostheses Resilient Cores.

Note that 4 a,b,c can also be fitted with Resilient Cores no matter what type of implant system is used as long as UAS/MUAS Assemblies are utilized.

Conclusion.

With the technology of the present invention there is no longer any need to place single implant restorations with large access bore holes for the primary fixation screw. All single crown restorations can now be anchored using a lingually positioned tube and screw rather than manually tapping a thread into the wall of the abutment. Because of the UAS/MUAS design there is also less risk of screw loosening and screw breakage. Furthermore, fully contoured anatomically correct crowns can now be created without flapping the periosteum or ridge lapping the tissue.

As far as multiple crown and bridge assemblies are concerned, there are now alternative anti screw loosening abutments without central access bores which give rise to an entirely new generation of intra abutment precision attachment patient removable prostheses.

With regard to combined implant/tooth restorations, these new abutments allow implants and natural teeth to be rigidly splinted together by incorporating resilient core components. The further incorporation of precision slide attachments allows this new generation of prostheses to be made patient removable.

This very same abutment system can also be used to radically alter overdenture designs as well. The technology of the present invention also eliminates problems associated with passive fitting tissue bars and screw loosening.

Section VIII: Evaluating Precision Attachment Designs for Implant Abutments.

With the very recent advances in implant abutment designs and resin bonding techniques, there is a very real need to re-evaluate precision attachment designs and applications in implant dentistry. Up until now, precision attachments have played a very minor role in the construction of an implant fixture. Screw blocks, T Blocks, set screws and simple dovetail and tube and lock slide attachments have been utilized, but with a very limited application. In fact the vast majority of these precision attachments have simply been used to help screw down, secure or tie together single or multiple crown and bridge frameworks so that they are held rigidly in place and can only be removed by the clinician. U. Grunder, J. R. Strub, *Implant-Supported Suprastructure Design*, 10 Int'l J. of Periodontics and Restorative Dentistry 18–38 (No. 1, 1990); D. E. Tolman, W. R. Laney, *Tissue-Integrated Prosthesis Complications*, 7 Int'l J. of Oral and Maxillofacial Implants 477–84 (No. 4, 1992); R. B. Johns, et al., *A Multicenter Study of Overdentures Supported by Branemark Implants;* R. P. Desjardens, *Prosthesis Design for Osseointegrated Implants in the Edentulous Maxilla*, 7 Int'l J. of Oral and Maxillofacial Implants 311–20 (No. 3, 1992); B. Langer, D. Y. Sullivan, *Osseointegration: Its Impact on the Interrelationship of Periodontics and Restorative Dentistry: Part II;* 9 Int'l J. of Periodontics and Restorative Dentistry 165–83 (No. 3, 1989); G. J. Chiche, et al., *Adapting Fixed Prosthodontics Principles to Screw-Retained Restorations*, 2 Int'l J. of Prosthodontics 317–412 (No. 4, 1989); G. J. Chiche, A. Pinault, *Consideration for Fabrication of Implant Supported Posterior Restorations*, 4 Int'l J. of Prosthodontics 37–44 (No. 1, 1991); R. M. Watson, D. M. Davis, G. H. Forman, T. Coward, *Consideration in Design and Fabrication of Maxillary Implant Supported Prostheses*, 4 Int'l J. of Prosthodontics 232–39 (No. 3, 1991); K. B. Tan, J. E. Rubenstein, J. I. Nicholls, R. A. Yuodelis, *Three-Dimensional Analysis of the Casting Accuracy of One Piece. Osseointegrated Implant-Retained Prostheses*, 6 Int'l J. of Prosthodontics 346–63 (No. 4, 1993); M. Perel, *Retrievability and Screw-Role Access*, 4 Dental Implantology Update 55 (FIG. 9), 60 (FIGS. 5–10) (No. 8, 1993); M. Perel, *Interview with Y. M. Ismail: Occlusion and Biomechanics in Implant Dentistry*, 4 Dental Implantology Update 6–8 (No. 1, 1993); G. J. Christensen, *Implant Prosthodontics Contribute to Restorative Dentistry*, 121 J.A.D.A. 340–50 (Sep. 1990); A. Fenton, *The Role of Dental Implants in the Future*, 123 J.A.D.A. 37–42 (Jan. 1992); D. A. Gorber, *Implants—The Name of the Game Is Still Maintenance*, 12 Compendium Contin. Educ. Dent. 876–86 (No. 12); B. Langer, *Dental Implants Used For Periodontal Patients*, 121 J.A.D.A. 505–08 (Oct. 1990); B. D. Monteith, *Minimizing Biomechanical Overload in Implant Prosthesis: A Computerized Aid To Design*, 69 J. of Prosthetic Dentistry 495–502 (No. 5, 1993); I. Ericsson, U. Lekholm, P. I. Branemark, J. Lindhe, P. O. Glanty, S. Nyman, *A Clinical Evaluation of Fixed Bridge Restoration Supported by the Combination of Teeth and Osseointegrated Titanium Implants*, 13 J. Clin. Periodontal 307–12 (1986).

However, with the UAS and MUAS designs, which eliminate the central access bores in the abutments, cavities for intra abutment precision slide attachments which can be resin bonded to place can now be created. This allows a new generation of crown and bridge frameworks to be made detachable and patient removable. These designs permit an entirely new set of design parameters and attachments to be created in order to develop stress broken prostheses, eliminate problems of passive fit and render the patient removable appliances user friendly.

Most precision attachments are made of metals and designed to be cast to or soldered rather than resin bonded. However Cendres & Metaux is breaking new ground in this respect but their resin bonding applications are limited to intracoronal frameworks for natural teeth and denture acrylic. With the UAS and MUAS designs of the present invention, the majority of precision attachments used in implant dentistry can now be made so that they can be resin bonded. Not only does resin bonding of attachments to another metal surface provide for very high interfacial bond strength (8–10,000 psi) but it also eliminates may of the steps involved in casting and soldering as well as the associated problems of temperature stresses which can affect the physical properties of the attachments.

In order to resin bond the patrix components into detachable framework, they must be designed either with tails that project from the back end of the attachment or the walls of the patrix must be slotted and knurled to provide for an adequately retentive surface. The same design concept must also be incorporated into the matrix housing in order to bond it into the abutment cavity. Furthermore, for those attachments that can be used in conjunction with the UAS system, an entire series of oversized ceramic spacers must be created to make adequate room for the silane coupling agent if necessary and the resin. Furthermore, because duplicating and/or refractoring models are required for this type of work, precision attachment matrix and patrix analogs must also be created. These analogs help to align, repair, fabricate and prevent wear and tear on the precision attachment components. The analogs are usually made of brass and can therefore be disposed of far more inexpensively. As was discussed in Section VI, only the outer surface of these analogs which is resin bonded is oversized—the inner mechanically interlocking surface is an exact likeness of the matrix and patrix components.

The following attachments have been designed with those features in mind.

The Stress Broken Attachment.

Figure 30:
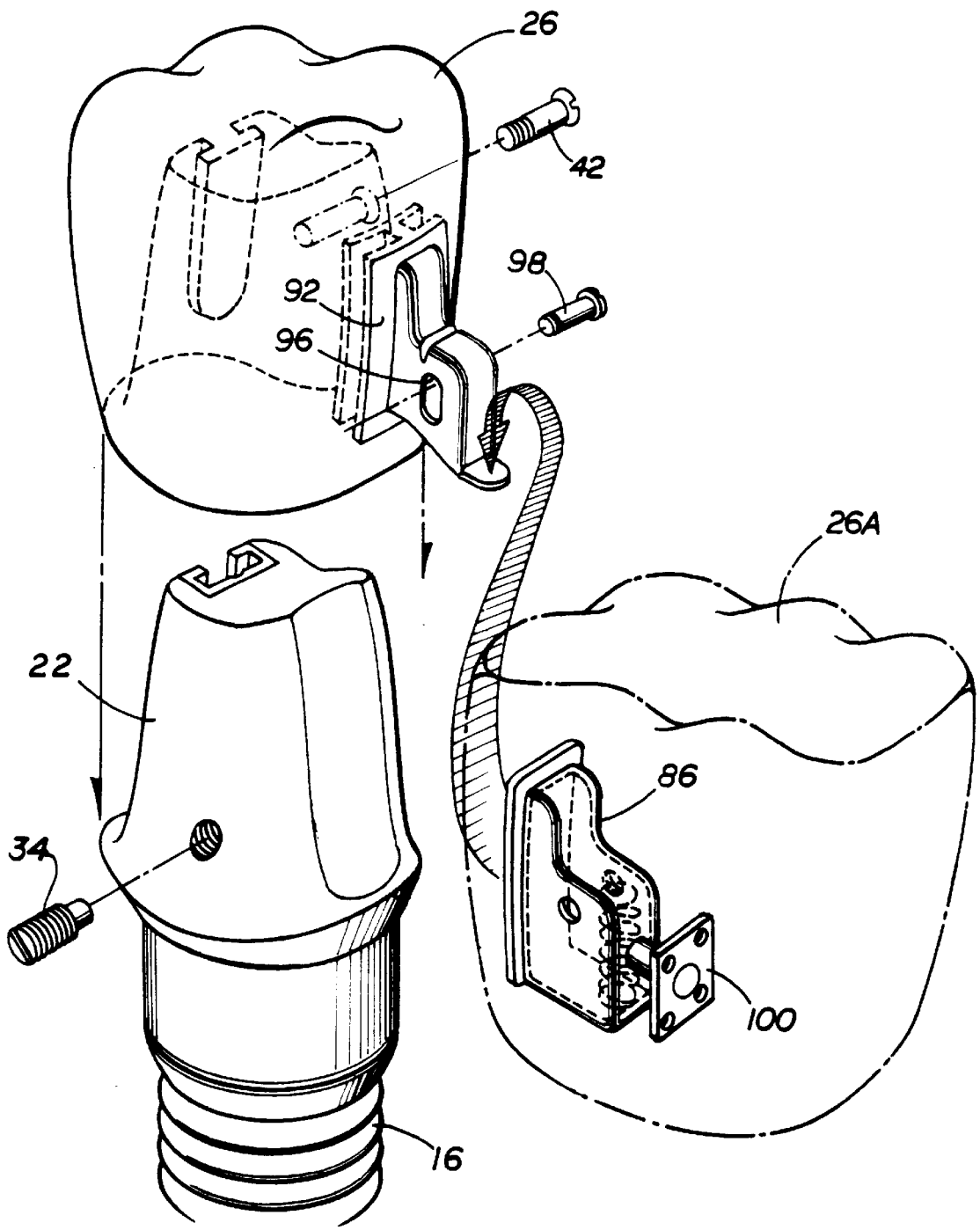
FIG. 30 is an exploded perspective view of a UAS according to the present invention that includes a precision attachment for use in a stress broken denture according to the present invention.
Figure 30A:
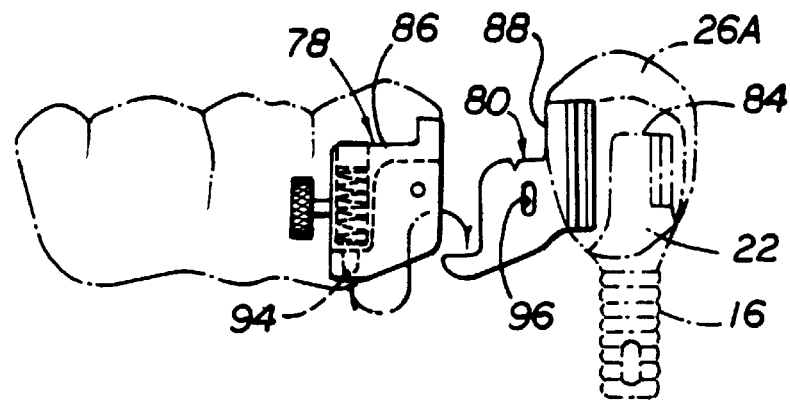
FIG. 30A is an exploded perspective view of a precision attachment according to the present invention for use in a stress broken denture according to the present invention.
Figure 30B:
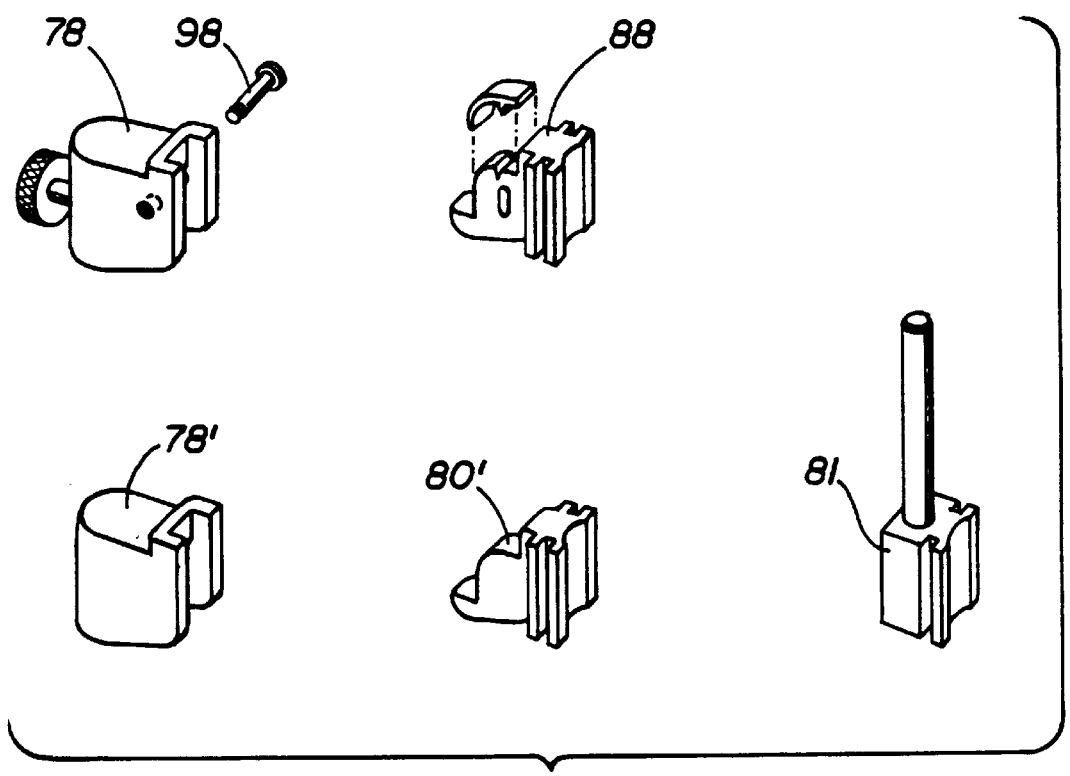
FIG. 30B is a cross sectional view of a matrix analog, patrix analog, matrix, patrix and INS spacer according to the present invention.

The UARS stress broken attachment 84, as shown in FIG. 30A, can be incorporated into the precision attachment stress broken denture. Its patrix component 88 is designed to be resin bonded into the framework and the matrix 86 is designed so that it can be bonded into the acrylic free end saddle. The following design features give this attachment a unique and specific function—that of stressbreaking.

(a) The patrix component 88 is slotted on both sides of its housing so it can grab onto the resin on the abutment cavity to which it is bonded. The patrix is mounted so that its male extension (guide rail) 90 is the only portion of the patrix that sticks out beyond the contour of the abutment 22 and the overlying crown 26.

(b) A ceramic spacer comes with the attachment so that the patrix component 88 has a preformed cavity 68 to fit into after the UAS Abutment 22 has been cast.

(c) Matrix and patrix analogs are also provided so that when a duplicating model is used the actual precision attachment components do not have to be placed until the prosthesis is taken to the patient's mouth.

(d) The guide rail 90 protrudes essentially vertically from the backplate 92 of patrix component 88. Incorporated into the guide rail design is a generally vertically oriented spring 94 for exerting upward force on the interior of the matrix component 86, a spacer and an elongated hole 96 for a threaded latch pin 98. The guide rail 90 slopes gently towards the gingiva and its corner is rounded off which allows the spring 94 interface to rotate anterior-posteriorally. The guide rail's roundness also allows the attachment 84 to hinge internally and away from the occlusal surface which further allows the matrix 86 component of the attachment 84 to be covered over with resin. The elongated hole 96 for the threaded latch pin 94 allows the matrix component 86 to move during vertical translation. The guide rail 90 is also designed so that it is sufficiently long occluso-gingivally to provide adequate lateral stability; it can even be tapered occluso-gingivally to allow for some rotational movement. This helps dramatically reduce the lateral forces of occlusion that are so damaging with normally designed attachments.

The spacer which fits overtop of the rounded portion of the guide rail 90 is used during the assembly and insertion of the attachment 84 to provide stability and prevent vertical translation. This allows for accurate occlusal adjustment and equilibration. The spacer features two small notches to help stabilize it and hold it in position.

(e) The matrix component 86 has a knurled tail 100 that projects backwards from the housing to help provide retention and stability in the acrylic of the free end saddle.

(f) The matrix component 86 is also designed with an internally recessed and rounded area to receive the spring 94 and the guide rail 90, which provides a good footing for the spring-loaded pin 94 and lends stability. The matrix component 86 fits overtop of the patrix 88 and is held in place by the threaded lingual latch pin 98.

The Vertex Attachment.

The Vertex attachment 102 according to the present invention, which is shown in FIGS. 31 and 32, features a male component 104 that includes (1) a protrusion 106 that may be generally H-shaped in cross section and that is adapted to be received in a prosthesis and (2) a generally cylindrical patrix component 108 aligned with the protrusion 106 whose lower portions 110 are generally cone shaped and comprise at least two leaflets 112 which may be spread apart by insertion of a spreader screw 114 into the bore 116 of the component 108. The patrix component 108 is received by a corresponding matrix component 118 which is adapted to be cast or otherwise formed into an abutment 22 according to the present invention and which features a cavity 120 corresponding in shape to the exterior of the patrix component 108 so that spreading of the leaflets 112 of the patrix component 108 allows it to be retained in the matrix component 118.

This attachment includes at least 3 functions:
1. A rigidly locking precision attachment;
2. A separable slide attachment (non locking); and
3. A frictional slide attachment with an occlusal adjustment screw to adjust the retention.

The Vertex attachment functions as a rigidly locking attachment when its occlusal spreader screw 114 is fully engaged to separate the two leaflets 112. This firmly engages a dimple 122 in the matrix 118 and locks the matrix 118 and patrix 108 components together. Such an attachment could be used to anchor a telescoped or sectional bridge together.

If the posterior most anchor (abutment) of the bridge fails and a partial denture needs to be constructed, the same attachment could be used—all that would be required is a modification to the occlusal spreader screw 114. By cutting its smooth tip portion off, the function changes. The Vertex attachment can now be placed and removed without ever locking together. This would allow the attachment to function in a removable partial denture. It would still have adjustable retention but manual manipulation of the leaflets 112 without a spreader screw 114 in place puts them at risk of loosening too quickly and even breaking.

Instead of cutting off the smooth tip of the occlusal spreader screw 114, plastic or metal washers can be simply inserted to bottom out against the screw 114. This means that the more washers that are placed the less the screw tip can engage and spread the leaflets, which results in less fractional retention between the matrix 118 and patrix 108. By removing a washer, the screw 114 can be tightened further into the chamber and thus the screw tip can engage and spread the leaflets 112 further. This results in increased retention. This ability to adjust the retention of the Vertex comes from an occlusal direction and is a much more accurate screw adjustment than manual adjustment of the leaflets.

This improved fractional adjustment modification is what gives this attachment its third function, and in this capacity it is designed to be used in a full/partial arch patient removable crown and bridge prosthesis which may or may not be implant supported. In either situation the matrix 118 is resin bonded into the abutment 22 and the patrix 108 resin bonded in the metal framework so that the occlusal spreader screw 114 is exposed. The telescopic crowns 26 or sections of crowns that fit over top of this framework are screw retrievable so as to allow access to the attachment for micro fine adjustments in retention of the patient removable prosthesis.

The taper of the leaflets 112 is also important to note and can be modified in any number of ways. It simply allows for easier positioning and insertion of the attachments and overlying prosthesis.

Section IX: Peri Implantitis Prosthetic Design and surgical Technique: Reevaluating The Causative Factors In Implant Loss And Examining A New Model Of Osseointegration Failure.

Over the last few years, many opinions have been formed regarding which causative factors influence dental implant loss. Although it seems glaringly obvious to some that it is more of a multivalent problem, certain schools of thought still maintain a contrary viewpoint. For example, Zarb and Albrechtsson have adopted the "No Periodontal Ligament/ No Periodontal Disease" mindset and they believe that "Iatrogenically induced soft tissue problems are not causes of implant failure . . . they are just a nuisance—no more, no less." G. Zarb, et al., *Osseointegration: A Requiem for the Periodontal Ligament?*, 11 Int'l J. of Periodontics and Restorative Dentistry 88–91 (No. 2, 1991). Zarb and Albrechtsson also believe that a soft tissue seal around the implant is not important and "that applying traditional prosthodontic-periodontic criteria as contributing factors to the process of implant loss is not particularly enlightened thinking." Id. In fact, they believe that conventional periodontal parameters are not applicable to the implant peri mucosal environment and should therefore be regarded as "inconsequential." For this reason, Zarb and Albrechtsson state that "there is no need for a measure of mucosal health" in studying implant success rates, even though they admit that "the immunohistologic profiles of peri implant lesions associated with osseointegration failure still need to be determined and that the mechanisms of implant failure . . . are inadequately understood." Id.

In a recent Oral Care Report by D. Braden Stauts, he referred to the criteria used by Zarb in the placement of single tooth implants. One of these criteria was the absence of any significant endodontic or periodontal problems generally and particularly in the teeth adjacent to the implant site. Zarb also has been quoted as saying "no periodontal ligament, no periodontal disease." If this last statement is true, why then would he be concerned about adjacent perio problems, especially when according to him periodontal inflammation is inconsequential? Zarb and Albrechtsson contend that the role of micro- and macrotrauma or occlusal stress appears to be the major candidate in the loss of osseointegration.

At the other extreme is a large group of clinicians and researchers who believe perio implant disease is consequential, even though according to Zarb they cannot identify the nature of osseointegration failure, which provides all the more reason not to adopt such a narrowed field of focus.

Clinicians such as Meffert believe that: (1) without a peri mucosal seal, an apical migration of epithelium into the implant bone interface takes place, as well as a fibrous encapsulation of the implant; and (2) occlusal stress or "retrograde peri implantitis" is also a causative factor in implant loss. R. M. Meffert, What is Peri-Implantitis and How Do We Prevent and Treat It?, 4 J. Michigan Dental Assoc. 32–33, 36–39 (No. 4, 1992).

Still, there are other factors that are not addressed by any of these clinicians, and until irrefutable scientific data has been compiled to prove otherwise, it would be unwise to adopt any of their positions. This is precisely why the following model of implant failure is offered and we should be constantly reminding ourselves that implant loss is a multivalent problem. In other words, if one does not completely understand what causes the problem, how can one selectively eliminate any of the pieces of the puzzle?

We must also remember that even though the implant-bone interface is a distinctly different environment than that of a natural tooth-periodontal ligament, the body still has the same immunohistological components (mast cells, lymphotoxins, macrophages, etc.) and the same host defense mechanisms. Therefore, the end result may be different with an implant as opposed to a tooth, but the body's response in the same area (the mouth) will always be the same.

Consider more closely what sort of effect flapping the periosteum at stage II uncovery causes on implant failure, and, furthermore, what effect premature bone loading has on osseointegration.

It is fact that the exposure of bone to our oxygenated surroundings causes bone necrosis, no matter how insignificant some people may have us believe it is. Furthermore, the jaw bone derives 30% of its arterial blood supply and 100% of its venous blood supply from the periosteum. Unless the periosteum has completely healed before the implant-bone interface is loaded, a stress on the system may be the result. This stress usually shows up as bone loss. It is the opinion of the inventor that the cupping around so many of the implants is due to premature loading as the bone around the implant still does not have adequate blood supply, simply because the periosteum has not completely reattached. Therefore, as stresses are applied to the implant-bone interface, instead of absorbing these stresses the bone begins to undergo cortical cratering and avascular necrosis, resulting in bone loss.

Furthermore, limitations in prosthetic design can also be directly tied to implant loss because excessive cantilevering forces can create occlusal overloading, which can lead to intrusion and extrusion of the implants and their ultimate failure. Impassive fitting frameworks can also have the same effect, as damaging lateral stresses can lead to retrograde peri implantitis. Perhaps the most obvious example of how limitations in prosthetic design can lead to implant loss is the overcontoured ridge lapped prosthesis, which invariably creates limited hygienic access. The inability to maintain the surrounding soft tissue properly leads to inflammation and the eventual breakdown of the hemidesmosomal attachment, which allows for an even deeper penetration of the inflammatory process. The end result is bone destruction and eventual implant loss.

It therefore behooves us not only to redesign the implant prostheses by making them more patient-removable, but also to help eliminate problems of occlusal overload and damaging lateral stresses by developing stress-breaking techniques. Creating non-invasive techniques such as the tapered gingivectomy procedure will also help prevent cupping and loss of peri implant bone. Incorporating split frame techniques and new means of progressive bone loading will also give the implant-bone interface more adequate time to mature.

It is, therefore, not enough to identify all of the causative factors in implant loss; we must also employ workable solutions such as those of the present invention.

Section X: Marking Blade Implants compatible with UAB and MUAS

There are still many instances where the use of a Modern 2 stage Blade Implant could be considered the treatment of choice when restoring an edentulous space. Even though it is always preferable to join a blade implant to either a root form implant or a natural tooth, blade implants can be indispensable in a situation when a short ridge is characterized by insufficient ridge width. In such a situation, a root form endosseous implant would potentially require onlay grafting. The blade implant on the other hand can alleviate the necessity for grafting or augmentation in one simple and low cost procedure.

The posterior mandible and the chronically edentulous maxilla are both areas where blade implants can frequently be used. Even though less than 10% of all endosseous implants placed are blade form, this still amounts to some fairly substantial numbers (50–60,000 units in North America alone).

Figures 37, 38:
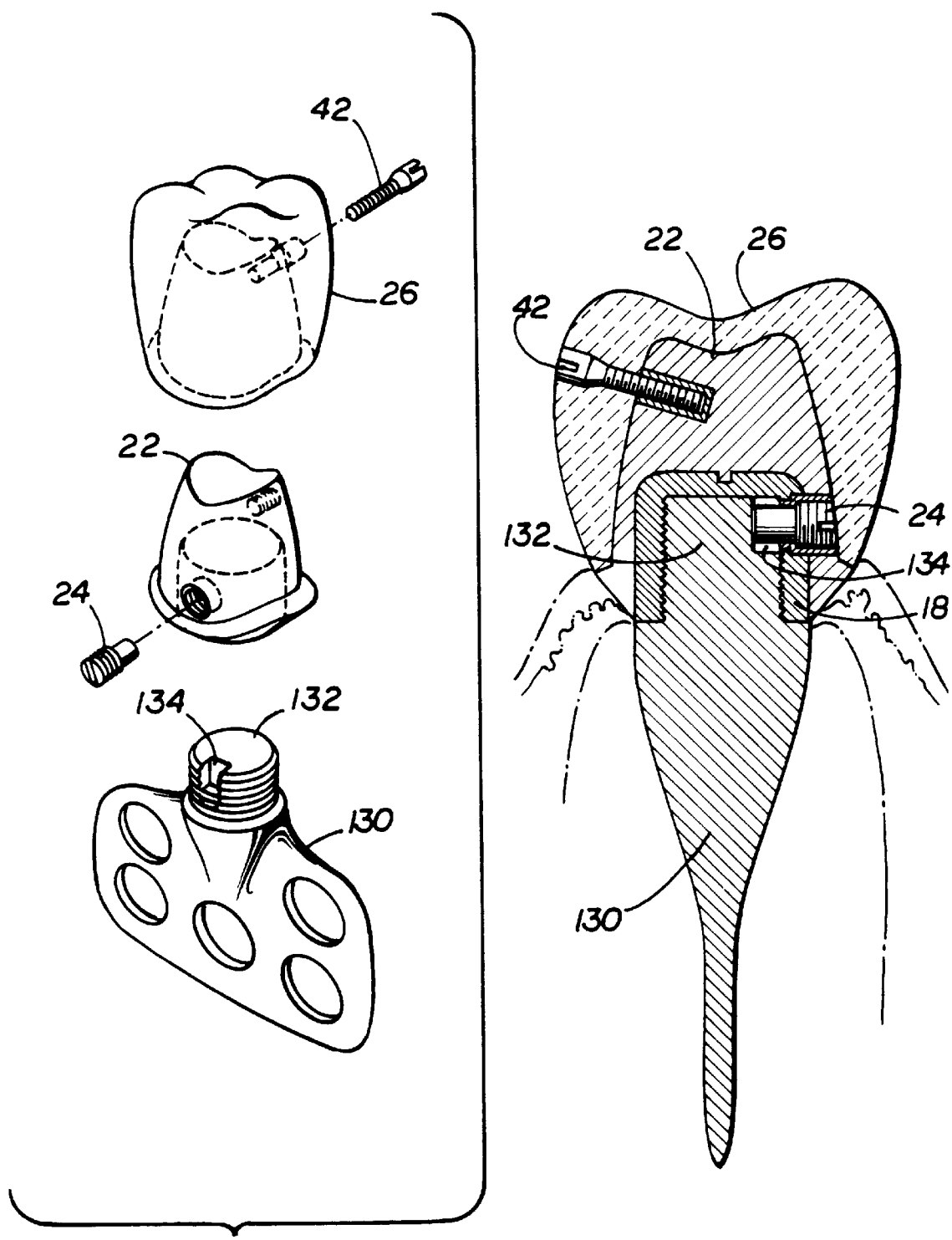
FIG. 37 is a perspective view of a conventional blade implant that has been modified to accommodate components of the present invention.
FIG. 38 is a cross sectional view of the implant of FIG. 37 supporting abutment components of the present invention.

For this simple reason the inventor believes that all blade implants should be modified slightly to allow them to be compatible with the UAS and MUAS, as shown, for example, in FIGS. 37 and 38. The modifications of the 2nd stage of the blade implant 130 are so minor and yet so significant. For example, by modifying the threaded heads 132 of the blade and placing a notch 134 into the buccal and lingual aspect of the head, you do not alter the fit of their standard screw down abutment. However, if you wish to screw down a UAS Core 18 component and lock in its rotational position, you need one or the other of these notches for the ALS mechanism to engage. Therefore, without the notches, the blades are not compatible. With these notches they are.

The notches are placed buccal and lingually because the second stage component of the blade is not adjustable and cannot be rotated. Therefore, the notches must be positioned so they do not interfere with the formation of customized abutment cavities etc. Once the UAS Core has been customized, there is no need to use telescopic copings or cement the overlying bridgework. Unlike the standard crown and bridge posts which cannot maintain an exact rotation position or be modified to incorporate intra abutment precision attachments, the components of the existing technology can.

A recent article by Dr. B. Nicolucci states that "the crown and bridge posts were placed on the threaded heads of the blades . . . they can be cut down to receive copings for draw." B. Nicolucci, *Dental Implants: The Blade Implant,* 83 Oral Health 55–60 (No. 9, 1993). The article further states that "the neck of the mesial head of the blade can be seen which allows for easy cleaning and maintenance." Id. Not only does the blade have to be left exposed to ensure cleansibility but it is this inventor's opinion that unless the prosthesis can be made patient removable, it is unlikely that it can be readily cleaned, particularly it if is fully contoured.

These significant differences and modifications offered by the technology of the present invention allow for patient removability, passive fit, better aesthetics and in situations where the blade implant is tied to natural teeth, they allow for the incorporation of resilient core components into the blade implant. This is something that has never been accomplished up until now, but with UAS and MUAS technology, these are fairly simple modifications.

Section XI: Modifying the Ankylos Implant System

In order to modify the Ankylos Implant System so that it is compatible with the technology of the present invention, modifications must be made to the Ankylos Implant, the entire abutment system and the threaded base component of the UAS and MUAS. By modifying these components, the implant itself not only gains a reproducible rotational lock but the 20 different prefabricated Ankylos abutments can be replaced with a simple four piece abutment which can be completely customized to any shape or angulation. This can be done using standard investment casting techniques or newly developed CAD/CAM procedures. The modifications to the base allow it to adapt to the mechanical interlock of the implant so that once the core component has been securely fastened, you have a system with no central access bore. These modifications also allow for incorporation of resilient components as well as offer all the other benefits of the UAS and MUAS.

The Ankylos Implant System has a conically tapered recess and relies upon a temperature gradient to cause expansion and subsequent frictional retention between two dissimilar metal surfaces. It does not utilize a mechanical interlock for rotational stability. This is achieved by fabricating an overlying telescopic framework.

The limitations of this approach are as follows:

(1) If the abutment ever has to be removed or comes loose, exact rotational repositioning is extremely difficult if not impossible.

(2) These Ankylos abutments are still screw retained and have central access bores.

(3) One and two together preclude the use of intra abutment precision attachment patient removable prostheses and also bring to mind concerns over screw loosening and passive fit etc.

(4) The extra steps involved in fabricating telescopic copings required to establish rotational stability is time consuming, costly and creates extra bulk.

(5) There is no means of developing an individual anatomically contoured gingival cuff using the prefabricated "sulkusformers."

(6) The system is limited to using prefabricated angulated abutments which cannot incorporate resilient components.

(7) If the metal expansion of the abutment relies on memory metal content (nickel, vanadium, etc.) FDA approval in U.S. will be exceedingly difficult to achieve due to a concern over allergic reaction, corrosion and biocompatibility.

(8) Finally, the components are specific to the Ankylos system. The are not interchangeable or compatible with any other implant system which definitely limits this product's market.

Basically, the Ankylos system has the same old problems as all the other conventional systems and until something is done to correct this, the Ankylos system will be competing on a level playing field with all the rest of its competitors.

By making the following modifications all of these problems can be eliminated:

(1) Create concentric slots or ribs in the tapered portion of the implant and a machined threaded UAS base to mate with it so that the UAS threaded base can be held in a multiple number of mechanically interlocking exact rotational positions.

(2) This same type of multiple rotational positioning can be achieved by machining a UAS threaded base with radial ribs to engage the four preexisting notches on the superior edge of the implant. Either of these methods will allow the UAS threaded base to be positioned in a variety of exact rotational position without using a memory metal or temperature expansion. This also means that when the UAS core is screwed down, it too will have reproducible rotational positions and therefore, so will the customized abutment (including a customized transmucosal cuff) and the intra abutment precision attachments. This can all be achieved without telescopic copings.

These small but distinct modifications mean that the Ankylos System can be easily made compatible with the UAS and MUAS. This allows for more system flexibility, such as incorporation of Resilient Cores and new prosthetic designs.

What is claimed is:

1. A dental implant abutment assembly, comprising:
    a. an implant for embedding in the osseous structure of a patient;
    b. a transition structure connected to said implant, said transition structure including a distal portion located distally of said transition structure relative to a central axis of said transition structure, and a proximal portion located proximally of said transition structure relative to a central axis of said transition structure, said distal portion containing a surface discontinuity for cooperating with a distal end of a fastener;
    c. a core structure connected to said transition structure, said core structure including an interior element generally forming a proximal portion cast to an exterior element generally forming a distal portion, and an interior surface and an exterior surface, said interior surface generally forming a concavity in said proximal portion of said core structure, said interior surface adapted in shape to receive said distal portion of said transition structure, said core structure defining a bore oriented in a direction different than said central axis of said transition structure;
    d. a fastener threadably received in said bore, said fastener bearing against said transition structure without passing into said transition structure to secure said core structure to said transition structure;
    e. a surfacing structure connected to said core structure;
    f. wherein said surfacing structure and said core structure contain no central bore oriented substantially parallel to said central axis of said transition structure, and said core structure is connected to said transition structure nonrotatably.

2. A dental implant abutment assembly according to claim 1, wherein said implant includes an interior threaded bore and said transition structure includes a threaded surface adapted to be threadably received in said implant threaded bore for connection of said transition structure to said implant.

3. A dental implant abutment assembly according to claim 1 wherein said fastener in said core structure impinges on a surface of said discontinuity in said transition structure, said fastener precluding said core structure from inadvertent separation distally from said transition structure.

4. A dental implant abutment assembly according to claim 1 wherein said bore in said core structure is threaded and said fastener comprises a screw threadably received in said threaded bore.

5. A dental implant abutment assembly according to claim 1 wherein said bore penetrates said interior element and said exterior element of said core structure.

6. A dental implant abutment assembly according to claim 1 wherein a screw mounted substantially transverse to said central axis of said transition structure connects said surface structure to said core structure.

7. A dental implant abutment assembly according to claim 1 wherein said implant is a non-blade implant.

8. A dental implant abutment assembly according to claim 1 wherein said implant is a root form implant.

9. A dental implant abutment assembly according to claim 1 wherein said implant is a sub-periosteal implant.

10. A dental implant abutment assembly according to claim 1 wherein said implant is a blade implant.

11. A dental implant abutment assembly according to claim 1 wherein said surface structure is a porcelain layer.

12. A dental implant abutment assembly according to claim 1 wherein said surface structure is a crown.

13. A dental implant abutment assembly according to claim 1 wherein said surface structure forms part of a denture.

14. A dental implant abutment assembly according to claim 1 wherein said surface structure forms part of a prosthesis.

15. A dental implant abutment assembly, comprising:
    a. an implant for embedding in the osseous structure of a patient:
    b. a transition structure connected to said implant, said transition structure including a distal portion located distally of said transition structure relative to a central axis of said transition structure, and a proximal portion located proximally of said transition structure relative to a central axis of said transition structure, said distal portion containing a surface discontinuity for cooperating with a distal end of a fastener;
    c. a core structure connected to said transition structure, said core structure including a distal portion and a proximal portion and an interior surface and an exterior surface, said interior surface generally forming a concavity in said proximal portion of said core structure, said interior surface adapted in shape to receive said distal portion of said transition structure, said core structure containing a bore oriented in a different direction than said central axis of said transition structure;
    d. a fastener threadably received in said bore, said fastener securing said core structure to said transition structure;
    e. a surfacing structure connected to said core structure;

f. wherein said surfacing structure and said core structure contain no central bore oriented substantially parallel to said central axis of said transition structure, and said core structure is connected to said transition structure nonrotatably, and wherein said exterior surface of said transition structure includes a threaded surface, said interior surface of said core structure includes a threaded surface, and said threaded surface of said core structure is secured to said threaded surface of said transition structure, said threaded surfaces precluding said core structure from inadvertent separation distally from said transition structure.

16. A dental implant abutment assembly, comprising:
a. an implant for embedding in the osseous structure of a patient;
b. a transition structure connected to said implant, said transition structure including a distal portion located distally of said transition structure relative to a central axis of said transition structure, and a proximal portion located proximally of said transition structure relative to a central axis of said transition structure, said distal portion containing a surface discontinuity for engaging a distal end of a fastener;
c. a core structure connected to said transition structure, said core structure including a distal portion and a proximal portion and an interior surface and an exterior surface, said interior surface generally forming a concavity in said proximal portion of said core structure, said interior surface adapted in shape to receive said distal portion of said transition structure, said core structure containing a bore oriented at an angle with respect to said central axis of said transition structure;
d. a fastener threadably received in said bore, said fastener securing said core structure to said transition structure:
e. a surfacing structure connected to said core structure;
f. wherein said surfacing structure and said core structure contain no central bore oriented substantially parallel to said central axis of said transition structure, said core structure is connected to said transition structure nonrotatably, and said core structure is formed of a single metallic element, an exterior surface of said single metallic element machined generally to form said distal portion and said exterior surface of said core structure, said distal portion and said exterior surface of said core formed of a shape generally to receive said surface structure, said surface structure in combination with said core structure generally forming a human tooth in shape.

17. A dental implant abutment assembly comprising:
a. an implant adapted to be embedded in the osseous structure of a patient, said implant containing a central axis oriented substantially longitudinally of said implant, said implant including a threaded bore formed in a distal portion of said implant;
b. a fixation element including a proximal portion which includes a threaded surface, said threaded surface threadably received in said threaded bore of said implant whereby said fixation element is coupled to said implant, said fixation element including a distal portion adapted in shape to couple to and retain a base element;
c. a base element comprising at least one surface adapted to couple to and be retained by said distal portion of said fixation element whereby said base element is precluded from inadvertent separation from said implant, said base element including an exterior surface containing a surface discontinuity for cooperating with a fastener;
d. a core structure connected to said base element, said core structure comprising an interior element generally forming a proximal portion and an interior surface of said core structure, and an exterior element cast to said interior element, said exterior element generally forming a distal portion and an exterior surface of said core structure, said interior surface generally forming a concavity in said proximal portion of said core structure and adapted in shape to receive a portion of said base element, said core structure including a bore oriented in a direction different than said central axis of said implant;
e. a fastener threadably received in said bore, said fastener bearing against said base element without passing into said base element to secure said core structure to said base element;
f. a surface structure connected to said core structure, said surface structure formed generally in the shape of a tooth;
g. wherein said surface structure and said core structure contain no central bore oriented substantially parallel to said central axis of said implant.

18. A dental implant abutment assembly according to claim 17 wherein said fastener in said core structure impinges on a surface of said discontinuity in said base element, said fastener precluding said core structure from inadvertent separation distally from said base element.

19. A dental implant abutment assembly according to claim 17 wherein said fixation element and said base element are coupled to form a unit and said core structure is coupled nonrotatably to said unit.

20. A dental implant abutment assembly according to claim 17 wherein said bore in said core structure is threaded and said fastener comprises a screw threadably received in said threaded bore.

21. A dental implant abutment assembly according to claim 17 wherein said bore penetrates said interior element and said exterior element of said core structure.

22. A dental implant abutment assembly according to claim 17 wherein a screw mounted substantially transverse to said central axis of said implant connects said surface structure to said core structure.

23. A dental implant abutment assembly according to claim 17 wherein said implant is a non-blade implant.

24. A dental implant abutment assembly according to claim 17 wherein said implant is a root form implant.

25. A dental implant abutment assembly according to claim 17 wherein said implant is a subperiosteal implant.

26. A dental implant abutment assembly according to claim 17 wherein said implant is a blade implant.

27. A dental implant abutment assembly according to claim 17 wherein said surface structure is a porcelain layer.

28. A dental implant abutment assembly according to claim 17 wherein said surface structure is a crown.

29. A dental implant abutment assembly according to claim 17 wherein said surface structure forms part of a denture.

30. A dental implant abutment assembly according to claim 17 wherein said surface structure forms part of a prosthesis.

31. A dental implant abutment assembly comprising:
a. an implant adapted to be embedded in the osseous structure of a patient, said implant containing a central axis oriented substantially longitudinally of said implant, said implant including a threaded bore formed in a distal portion of said implant;
b. a fixation element including a proximal portion which includes a threaded surface, said threaded surface threadably received in said threaded bore of said implant whereby said fixation element is coupled to said implant, said fixation element including a distal portion adapted in shape to couple to and retain a base element;

c. a base element comprising at least one surface adapted to couple to and be retained by said distal portion of said fixation element whereby said base element is precluded from inadvertent separation from said implant, said base element including an exterior surface containing a surface discontinuity for cooperating with a fastener:

d. a core structure connected to said base element, said core structure including a distal portion and a proximal portion and an interior surface and an exterior surface, said interior surface generally forming a concavity in said proximal portion of said core structure, said interior surface adapted in shape to receive a portion of said base element, said core structure containing a bore oriented in a direction different than said central axis of said implant;

e. a fastener threadably received in said bore, said fastener securing said core structure to said base element:

f. a surface structure connected to said core structure, said surface structure formed generally in the shape of a tooth;

wherein said surface structure and said core structure contain no central bore oriented substantially parallel to said central axis of said implant, and wherein said exterior surface of said base element includes a threaded surface, said interior surface of said core structure includes a threaded surface, and said threaded surface of said core structure is secured to said threaded surface of said base element, said threaded surfaces precluding said core structure from inadvertent separation distally from said base element.

32. A dental implant abutment assembly comprising:

a. an implant adapted to be embedded in the osseous structure of a patient, said implant containing a central axis oriented substantially longitudinally of said implant, said implant including a threaded bore formed in a distal portion of said implant;

b. a fixation element including a proximal portion which includes a threaded surface, said threaded surface threadably received in said threaded bore of said implant whereby said fixation element is coupled to said implant, said fixation element including a distal portion adapted in shape to couple to and retain a base element;

c. a base element comprising at least one surface adapted to couple to and be retained by said distal portion of said fixation element whereby said base element is precluded from inadvertent separation from said fixation element, said base element including an exterior surface containing a surface discontinuity for engaging a fastener:

d. a core structure connected to said base element, said core structure including a distal portion and a proximal portion and an interior surface and an exterior surface, said interior surface generally forming a concavity in said proximal portion of said core structure, said interior surface adapted in shape to receive a portion of said base element, said core structure containing a bore oriented at an angle with respect to said central axis of said implant, said core structure being formed of a single metallic element, an exterior surface of said single metallic element machined generally to form said distal portion and said exterior surface of said core structure;

e. a fastener threadably received in said bore, said fastener securing said core structure to said base element;

f. a surface structure connected to said core structure, said distal portion and said exterior surface of said core structure formed of a shape generally to receive said surface structure, said surface structure including a porcelain layer generally forming a human tooth in shape;

g. wherein said surface structure and said core structure contain no central bore oriented substantially parallel to said central axis of said implant.

33. A process for forming a dental implant abutment assembly, comprising:

a. embedding an implant in the osseous structure of a patient, said implant including a central axis longitudinally to said implant;

b. providing an abutment structure and connecting said abutment structure to said implant;

C. providing a core, said core including an interior surface adapted to receive at least a portion of said abutment structure, said core including a substantially transverse bore adapted to receive a fastener;

d. casting a metal element to said core, said metal portion approximating more closely at least some contours of a human tooth more closely than said core;

e. connecting said core and metal element to said abutment structure using no fastener which penetrates said core substantially parallel to said central axis of said implant;

f. installing said fastener to preclude said core and said abutment structure from rotating relative to each other, and to preclude said core from inadvertent separation from said abutment structure; and g. providing a surface structure on said metal element cast to said core, to form a shape substantially conforming to a human tooth.

34. A process for forming a dental implant abutment assembly, comprising:

a. embedding an implant in the osseous structure of a patient, said implant including a central axis longitudinally to said implant;

b. providing an abutment structure and connecting said abutment structure to said implant;

c. providing a blank core, said blank core including an interior surface adapted to receive at least a portion of said abutment structure, said blank core including a substantially transverse bore adapted to receive a fastener; said blank core adapted to be machined into a desired shape;

d. machining said blank core to create a core which conforms in shape to a predetermined shape generally corresponding to contours of a human tooth;

e. connecting said core to said abutment structure;

f. installing said fastener to preclude said core and said abutment structure from rotating relative to each other, and to preclude said core from inadvertent separation from said abutment structure; and g. providing a surface structure on said core, to form a shape substantially conforming to a human tooth.

* * * * *